United States Patent [19]

Koya et al.

[11] Patent Number: 4,916,047
[45] Date of Patent: Apr. 10, 1990

[54] SILVER HALIDE LIGHT-SENSITIVE MATERIAL

[75] Inventors: Keizo Koya; Junichi Yamanouchi; Masaharu Toriuchi; Yoshisada Nakamura, all of Kanagawa, Japan

[73] Assignee: Fuji Photo Film Co., Ltd., Kanagawa, Japan

[21] Appl. No.: 188,782

[22] Filed: Apr. 29, 1988

[30] Foreign Application Priority Data

Apr. 30, 1987 [JP] Japan .................................. 62-106881
Dec. 23, 1987 [JP] Japan .................................. 62-325956

[51] Int. Cl.$^4$ ......................... G03C 1/06; G03C 1/34; G03C 7/26; G03C 5/54
[52] U.S. Cl. .................................... 430/353; 430/203; 430/223; 430/444; 430/446; 430/542; 430/544; 430/543; 430/551; 430/559; 430/598; 430/562; 430/564; 430/566; 430/606; 430/609; 430/613; 430/617; 430/623; 430/627; 430/629; 430/630; 430/631; 430/955; 430/956; 430/957; 430/958; 430/959
[58] Field of Search ............... 430/564, 505, 544, 955, 430/956, 957, 958, 627, 598, 593, 613, 559, 955, 956, 957, 958, 959, 609, 627, 629, 630, 606, 613, 617, 623, 631, 203, 223, 353, 444, 446, 542, 544, 543, 551, 559, 598, 562, 564, 566

[56] References Cited

U.S. PATENT DOCUMENTS

| 4,450,223 | 5/1984 | Van Poucke et al. | 430/223 |
| 4,551,423 | 11/1985 | Koyama et al. | 430/559 |
| 4,639,408 | 1/1987 | Kitaguchi et al. | 430/351 |
| 4,678,739 | 7/1987 | Kitaguchi et al. | 430/353 |
| 4,695,525 | 9/1987 | Tsukase et al. | 430/955 |
| 4,770,990 | 9/1988 | Nakamura et al. | 430/223 |
| 4,783,396 | 11/1988 | Nakamura et al. | 430/353 |

FOREIGN PATENT DOCUMENTS

| 0187343 | 7/1986 | European Pat. Off. |
| 0220746 | 5/1987 | European Pat. Off. |
| 2062352 | 3/1987 | Japan |

Primary Examiner—Paul R. Michl
Assistant Examiner—Lee C. Wright
Attorney, Agent, or Firm—Sughrue, Mion, Zinn, Macpeak & Seas

[57] ABSTRACT

A silver halide light-sensitive material comprising a support having thereon at least one silver halide emulsion layer, and containing a compound containing a repeating unit, said compound containing a repeating unit being connected at the repeating unit to a compound represented by formula (I) at the position of the PWR or Time moiety:

PWR (—Time)$_t$ PUG          (I)

wherein PWR represents a moiety capable of releasing (Time) PUG upon reduction, and PUG represents a group which can fulfil a photographically useful function after the release; Time represents a moiety capable of releasing PUG through a reaction subsequent to the release from PWR in the form of (—Time) PUG; and t represents 0 or 1.

19 Claims, No Drawings

SILVER HALIDE LIGHT-SENSITIVE MATERIAL

FIELD OF THE INVENTION

The present invention relates to a silver halide photographic material, and particularly to a silver halide photograhic material containing a novel high molecular compound which can release a photographically useful group by taking advantage of the redox reaction with a reducing agent as a trigger.

BACKGROUND OF THE INVENTION

Compounds which can reverse-imagewise release a photographically useful group, or positive-working compounds, have been energetically studied, because they can serve various functions, which have never been performed by conventional precursors in a silver halide photographic material.

As for the positive-working compounds, immobile compounds disclosed in U.S. Pat. Nos. 4,199,354 and 3,980,479 have been proposed.

Those compounds can release photographic reagents in the reduced condition by undergoing an intramolecular nucleophilic reaction in the presence of an alkali, whereas when oxidized through a redox reaction in the light-sensitive material they have a decreased release rate of the photographic reagent. By utilization of this property, imagewise release of photographically useful groups from such compounds is feasible. However, they have certain disadvantages, e.g., generation of fog and deterioration of discrimination, which result from a timing lag upon competition between the oxidation and the alkaline hydrolysis, insufficient stability of the compounds themselves, and so on.

For the purpose of solving the problems of the above-described photographic reagent-releasing compounds of positive-working type, a great number of positive-working compounds have been developed on the basis of the idea that positive-working compounds themselves are converted to the oxidized form, from which photographically useful groups are released through the redox reaction with reducing agents.

Further, positive-working compounds which can release photographic reagents by an intramolecular nucleophilic substitution reaction after they are reduced, include those disclosed in U.S. Pat. Nos. 4,139,389, 4,139,379 and 4,564,577, and Japanese Patent Application (OPI) Nos. 185333/84 and 84453/82 (the term "OPI" as used herein means an "unexamined published Japanese patent application"); and positive-working compounds which can split off photographic reagents by an intramolecular electron transfer reaction after they are reduced, include those disclosed in U.S Pat. No. 4,232,107, Japanese Patent Application (OPI) No. 101649/84, *Research Disclosure* IV, No. 24025 (1984), and Japanese Patent Application (OPI) No. 88257/86.

Furthermore, positive-working compounds which can release photographic reagents by bond cleavage by reduction have been studied.

Examples include compounds which utilize the reductive cleavage of an N—S bond, as disclosed in West German Patent No. 3,008,588; and compounds which utilize N—N bond cleavage, disclosed in U.S. Patent No. 4,619,884. In addition, examples include α-nitro compounds which can release photographic reagents through acceptance of an electron and the subsequent cleavage of the single bond between a carbon atom and a hereto atom, as disclosed in West German Pat. No. 8,207,583; compounds which utilize the reductive cleavage of a single bond between a carbon atom and a hereto atom, for example, gemminate dinitro compounds which undergo β-elimination of photographic reagents after the reductive cleavage of a bond between a carbon atom and a nitrogen atom (nitro group), which are disclosed in U.S. Pat. No. 4,609,610; and nitrobenzyl compounds disclosed in U.S. Pat. No. 4,343,893, which utilize the reductive cleavage of a single bond between a carbon atom and a hereto atom.

In recent years, European Pat. No. 220,746 A2 and Kokai Giho No. 87-6199 (May 20, 1987) have developed positive-working compounds satisfying two contradictory requirements of excellent stability, and higher activity upon processing, to permit more freedom of design and latitude in making photographic elements and operating processes.

Each of the compounds having functions as described above has many advantages. However, they are crystalline low-lomecular compounds, so emulsions containing them are unstable and precipitate crystals, and they can easily migrate among layers to exert undesirable effects upon other layers through diffusion.

Further, when a high-boiling organic solvent is used at the time of emulsification for incorporation of such compounds into a silver halide light-sensitive material, it frequently causes the softening of the layer in which it was contained to decrease the film strength and deteriorate adhesiveness between layers.

SUMMARY OF THE INVENTION

A first object of the present invention is to provide a silver halide light-sensitive material which contains a novel high molecular compound capable of releasing a photographically useful group by taking a redox reaction with a reducing agent as a trigger.

A second object of the present invention is to provide a silver halide light-sensitive material containing a novel high molecular compound which can release a photographically useful group, and has reduced diffusion into other layers because of its small mobility.

A third object of the present invention is to provide a silver halide light-sensitive material containing a novel high molecular compound which can release a photographically useful group, and can be stably emulsified without separation as precipitates.

A fourth object of the present invention is to provide a silver halide photographic material containing a novel high molecular compound which can release a photographically useful group, without significant lowering of film strength or deterioration of adhesiveness between adjacent layers in combined use with a high-boiling organic solvent.

it has now been discovered that these and other objects of the present invention are attained by a silver halide light-sensitive material comprising a support having thereon at least one silver halide emulsion layer, and containing a compound containing a repeating unit, said compound containing a repeating unit being connected at the repeating unit to—; a compound represented by formula (I) at the position of the PWR or Time moiety:

$$\text{PWR}-(\text{Time})_i-\text{PUG} \qquad (I)$$

wherein PWR represents a moiety capable of releasing (Time—$_t$PUG upon reduction, and PUG represents a group which can fulfill a photographically useful function after the release; Time represents a moiety capable of releasing PUG through a reaction subsequent to the release from PWR in the form of —Time—$_t$PUG; and t represents 0 or 1.

DETAILED DESCRIPTION OF THE INVENTION

The group represented by PWR may be any of the groups containing an electron accepting center and an intramolecular nucleophilic substitution center in a compound capable of releasing a photographic reagent through reduction followed by intramolecular nucleophilic substitution as disclosed in U.S. Pat. Nos. 4,139,389, 4,139,379 and 4,564,577 and Japanese Patent Application (OPI) Nos. 185333/84 and 84453/82; the group containing an electron accepting quinoid center and a carbon atom connecting the quinoid center to a photographic reagent in a compound capable of releasing a photographic reagent through reduction followed by intramolecular electron transfer as disclosed in U.S. Pat. No. 4,232,107, Japanese Patent Application (OPI) No. 101649/84, Research Disclosure, No. 24025, IV (1984), and Japanese Patent Application (OPI) No. 88257/86; the group containing an aryl group substituted with an electron attractive group and an atom (a sulfur, carbon or nitrogen atom) connecting the substituted aryl group to a photographic reagent in a compound capable of releasing a photographic reagent through reduction followed by cleavage of its single bond as disclosed in West German Patent Application (OLS) No. 3,008,588, Japanese Patent Application (OPI) No. 142530/81, and U.S. Pat. Nos. 4,343,893 and 4,619,884; the group containing a nitro group and a carbon atom connecting the nitro group to a photographic reagent in a nitro compound capable of releasing a photographic reagent after electron acceptance as disclosed in U.S. Patent No. 4,450,223; and the group containing a gem-dinitro group and a carbon atom connecting the dinitro group to a photographic reagent in a dinitro compound capable of $\beta$-releasing a photographic reagent after electron acceptance as disclosed in U.S. Pat. No. 4,609,610.

In addition, compounds containing both $SO_2$—X (wherein X represents an oxygen, sulfur or nitrogen atom) and an electron withdrawing group in a molecule, as described in Japanese Patent Application No. 106885/87; and compounds containing both C—X' bond (wherein X' represents the same atom as X, or —$SO_2$—) and an electron withdrawing group, as described in Japanese Patent Application No. 106887/87 can be given as examples.

Preferred compounds represented by formula (I) are represented by formula (II):

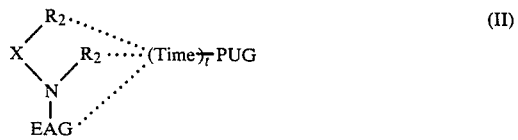

(II)

wherein EAG represents an electron accepting group; N represents a nitrogen atom, and X represents an oxygen atom (—O—), a sulfur atom (—S—), or a nitrogen-containing group (—N(R$_3$)—); R$_1$, R$_2$, and R$_3$ each represents a mere bonding hand, or a group other than a hydrogen atom; R$_1$, R$_2$, R$_3$ and EAG may combine with one another to form a ring; and Time represents a group to release PUB through a reaction which succeeds taking advantage of the N—X bond cleavage as a trigger, t represents 0 or 1, and when t is 0, Time represents a mere bonding hand; and wherein each of the full lines indicates a bond, and the dashed lines indicate that at least one of them is a bond; and PUG is as defined in formula (I).

In formula (II),

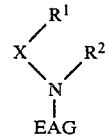

corresponds to PWR of formula (I). (Time$\rightarrow_t$PUG is bonded to at least one of R$_1$ R$_2$, and EAG.

The group other than a hydrogen atom represented by R$_1$, R$_2$, and R$_3$ includes a substituted or unsubstituted alkyl or aralkyl group (e.g., methyl, trifluoromethyl, benzyl, chloromethyl, dimethylaminomethyl, ethoxycarbonylmethyl, aminomethyl, acetylaminomethyl, ethyl, 2-(4-dodecanoylaminophenyl)ethyl, carboxyethyl, allyl, 3,3,3-trichloropropyl, n-propyl, isopropyl, n-butyl, iso-butyl, sec-butyl, t-butyl, n-pentyl, sec-pentyl, t-pentyl, cyclopentyl, n-hexyl, sec-hexyl, t-hexyl, cyclohexyl, n-octyl, sec-octyl, t-octyl, n-decyl, n-undecyl, n-dodecyl, n-tetradecyl, n-pentadecyl, n-hexadecyl, sec-hexadecyl, t-hexadecyl, n-octadecyl, and t-octadecyl groups), a substituted or unsubstituted alkenyl group (e.g., vinyl, 2-chlorovinyl, 1-methylvinyl, 2-cyanovinyl, and cyclohexen-1-yl groups), a substituted and unsubstituted alkynyl group (e.g., ethynyl, 1-propynyl, and 2-ethoxycarbonylethynyl groups), a substituted or unsubstituted aryl group (e.g., phenyl, naphthyl, 3-hydroxyphenyl, 3-chlorophenyl, 4-actylaminophenyl, 4-hexadecanesulfonylaminophenyl, 2-methanesulfonyl-4-nitrophenyl, 3-nitrophenyl, 4-methoxyphenyl, 4-acetylaminophenyl, 4-methanesulfonylphenyl, 2,4-dimethylphenyl, and 4-tetradecyloxyphenyl groups), a substituted or unsubstituted heterocyclic group (e.g., 1-imidazolyl, 2-furyl, 2-pyridyl, 5-nitro-2-pyridyl, 3-pyridyl, 3,5-dicyano-2-pyridyl, 5-tetrazolyl, 5-phenyl-1-tetrazolyl, 2-benzothiazolyl, 2-benzimidazolyl, 2-benzoxazolyl, 2-oxazolin-2-yl, and morpholino groups), a substituted or unsubstituted acyl group (e.g., acetyl, propionyl, butyroyl, iso-butyroyl, 2,2-dimethylpropionyl, benzoyl, 3,4-dichlorobenzoyl, 2-acetylamino-4-methoxybenzoyl, 4-methylbenzoyl, and 4-methoxy-3-sulfobenzoyl groups), a substituted or unsubstituted sulfonyl group (e.g., methanesulfonyl, ethanesulfonyl, chloromethanesulfonyl, propanesulfonyl, butanesulfonyl, n-octanesulfonyl, n-dodecanesulfonyl, n-hexadecanesulfonyl, benzenesulfonyl, 4-toluenesulfonyl, and 4-n-dodecyloxybenzenesulfonyl groups), a substituted or unsubstituted carbamoyl group (e.g., carbamoyl, methylcarbamoyl, dimethylcarbamoyl, bis-(2-methoxyethyl)carbamoyl, diethylcarbamoyl, cyclohexylcarbamoyl, di-n-octylcarbamoyl, 3-dodecyloxypropyl-carbamoyl, hexadecylcarbamoyl, 3-(2,4-di-t-pentylphenoxy)-propylcarbamoyl, 3-octanesulfonylaminophenycarbamoyl, and di-n-octadecylcarbamoyl groups), a substituted or unsubstituted sulfamoyl group (e.g., sulfamoyl, methylsulfamoyl, dimethylsulfamoyl, diethylsulfamoyl, bis(2-methoxyethyl)sulfamoyl, di-n- butylsulfamoyl, methyl-n-octylsulfamoyl, n-hexadecyl-methysulfamoyl, 3-ethoxypropylmethyl sulfamoyl, N-phenyl-N-methylsulfamoyl, 4-decyloxyphenylsulfamoyl, and methyloctadecylsulfamoyl group), and the like.

$R_1$ and $R_3$ each preferably represents a substituted or unsubstituted alkyl, alkenyl, alkynyl, aryl, heterocyclic, acyl or sulfonyl group, etc. $R_1$ and $R_3$ each preferably contains 1 to 40 carbon atoms.

$R_2$ preferably represents a substituted or unsubstituted acyl or sulfonyl group and preferably contains 1 to 40 carbon atoms.

X preferably represents an oxygen atom.

More preferred among the compounds represented by formula (II) are those represented by formula (III):

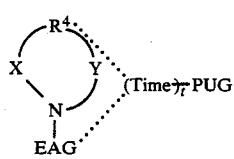  (III)

wherein Y represents a divalent linking group; and is preferably

or —SO$_2$—; $R_4$ represents atoms which are bonded to X and Y and complete a 5- to 8-membered heterocyclic ring together with the nitrogen atom; and N, X, EAG, Time, t and PUG are each as defined in formula (II).

In formula (III),

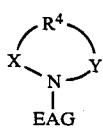

corresponds to PWR in formula (I), and (Time)$_t$PUG is bonded to at least one of $R_4$ EAG.

Specific and preffered examples of the heterocyclic ring formed by X, Y, $R_4$, and N are shown below.

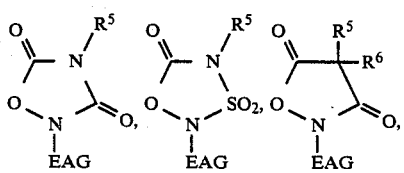

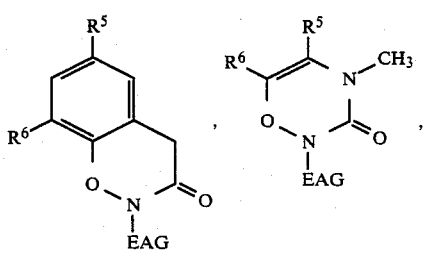

-continued

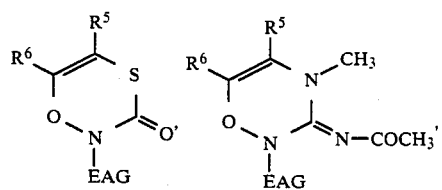

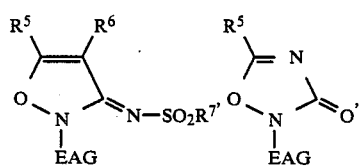

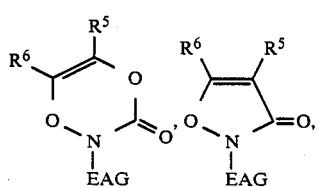

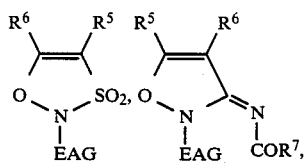

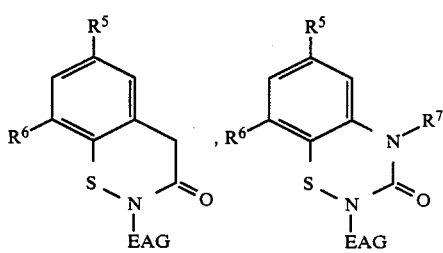

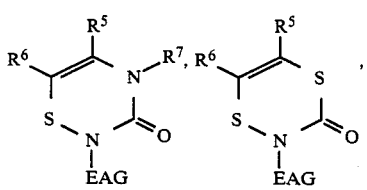

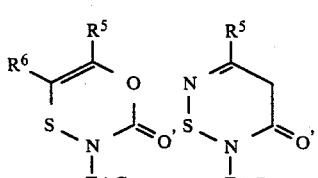

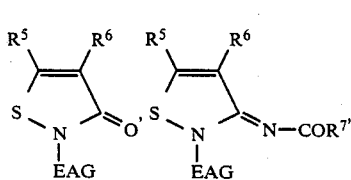

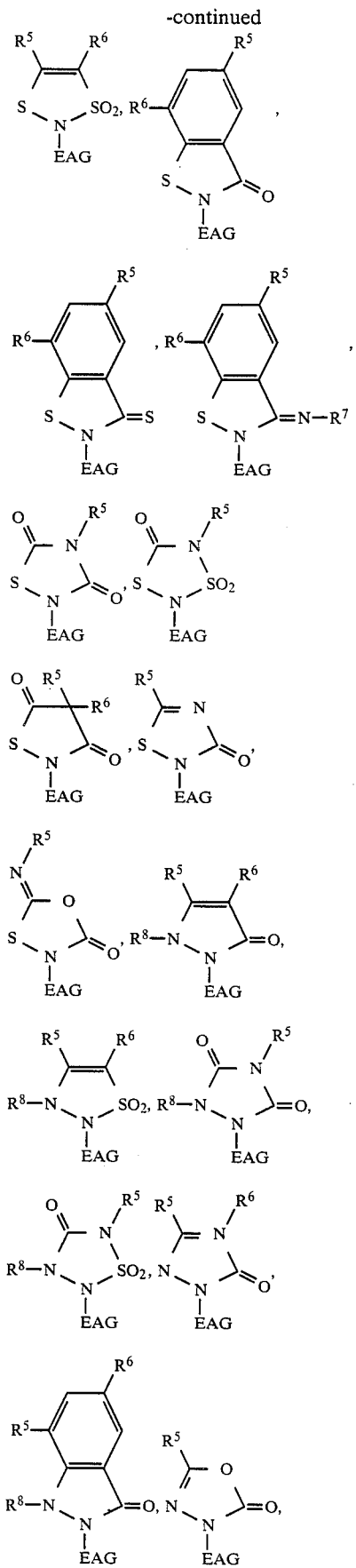
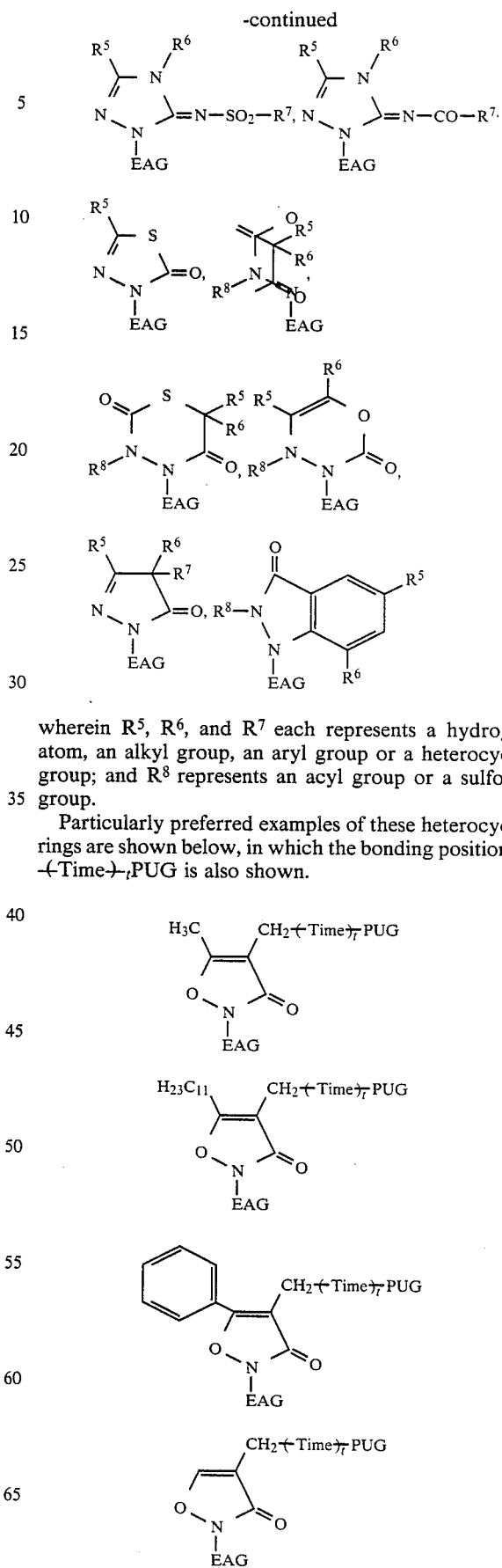
wherein $R^5$, $R^6$, and $R^7$ each represents a hydrogen atom, an alkyl group, an aryl group or a heterocyclic group; and $R^8$ represents an acyl group or a sulfonyl group.
Particularly preferred examples of these heterocyclic rings are shown below, in which the bonding position of $-(\text{Time})_t$-PUG is also shown.

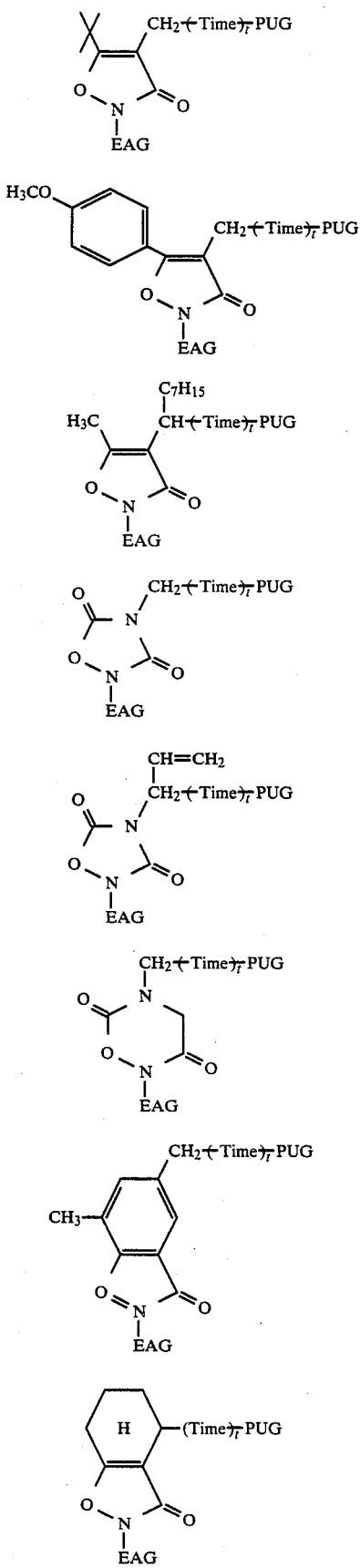
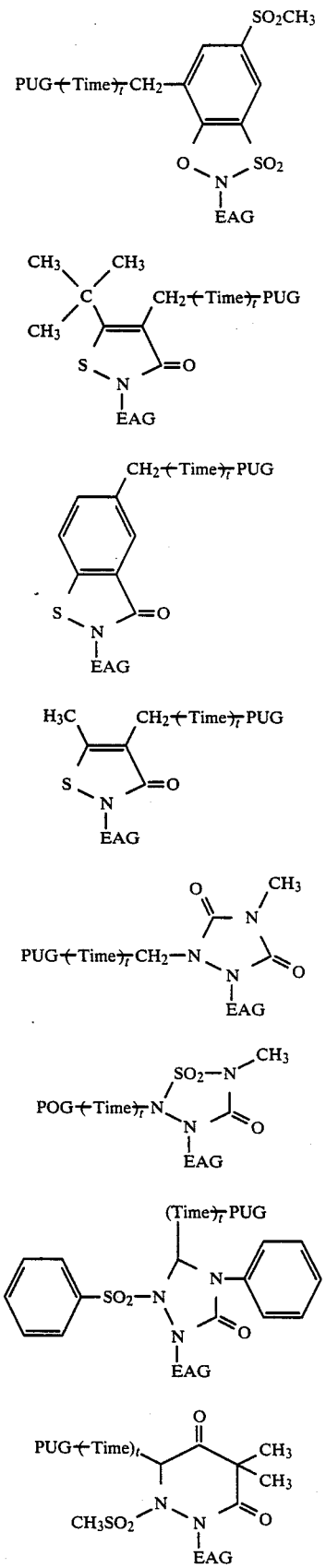

-continued

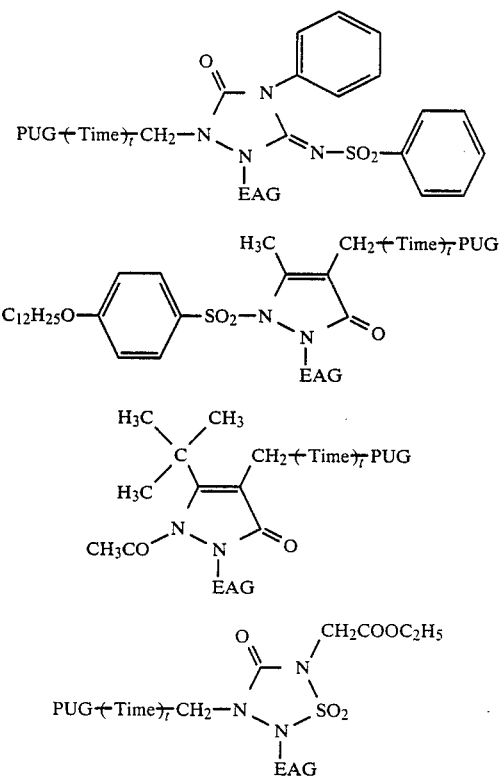

Throughout the specification, the symbols

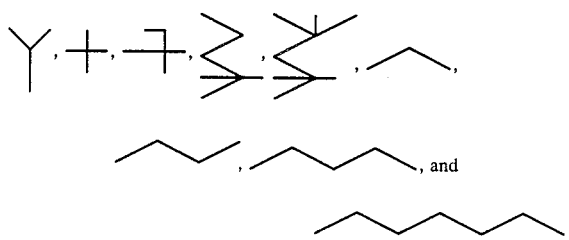, and

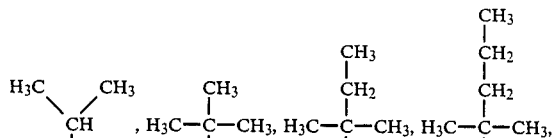

in the formulae represent

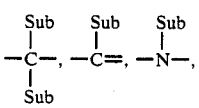

—CH$_2$—, —CH$_2$—CH$_2$—, —CH$_2$—CH$_2$—CH$_2$—, and —CH$_2$—CH$_2$—CH$_2$—CH$_2$—CH$_2$—, respectively.

In formula (II), EAG represents an aromatic group capable of accepting an electron from a reducing substance and is bonded to the nitrogen atom. EAG preferably includes a group represented by formula (A):

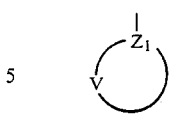 (A)

wherein $Z_1$ represents

or a nitrogen atom; and V represents an atomic group necessary for forming a 3-membered to 8-membered aromatic ring containing members selected from $$-\underset{\underset{\text{Sub}}{|}}{\overset{\text{Sub}}{\underset{|}{C}}}-, \quad -\overset{\text{Sub}}{\underset{|}{C}}=, \quad -\overset{\text{Sub}}{\underset{|}{N}}-,$$

—N=, —O—, —S— and —SO$_2$—; wherein Sub, represents a hydrogen atom or a substituent hereinafter described and plural Sub groups may be the same or different, and at least two Sub groups may be linked to form a 3-membered to 8-membered saturated or unsaturated carbon ring or heterocyclic ring; provided that the sum of the Hammett's sigma constants and Hammett's para constants of the Sub groups is at least +0.50, preferably at least +0.70, and more preferably at least +0.85.

EAG preferably represents an aryl or heterocyclic group substituted with at least one electron attractive group. The substituent on the aryl or heterocyclic group can be used for controlling physical properties of the compound as a whole, such as electron acceptance, water solubility, oil solubility, diffusibility, sublimating properties, melting point, dispersibility in a binder (e.g., gelatin), reactivity to a nucleophilic group, reactivity to an electrophilic group, and the like.

Specific examples of the aryl group substituted with at least one electron attractive group are 4-nitrophenyl, 2-nitrophenyl, 2-nitro-4-N-methyl-N-n-butylsulfamoylphenyl, 2-nitro-4-N-methyl-N-n-octylsulfamoylphenyl, 2-nitro-4-N-methyl-N-n-dodecylsulfamoylphenyl, 2-nitro-4-N-methyl-N-n-hexadecylsulfamoylphenyl, 2-nitro-4-N-methyl-N-n-octadecylsulfamoylphenyl, 2-nitro-4-N-methyl-N-(3-carboxypropyl)sulfamoylphenyl, 2-nitro-4-N-ethyl-N-(2-sulfoethyl)sulfamoylphenyl, 2-nitro-4-N-n-hexadecyl-N-(3-sulfopropyl)sulfamoylphenyl, 2-nitro-4-N-(2-cyanoethyl)-N-[(2-hydroxyethoxy)ethyl]sulfamoylphenyl, 2-nitro-4-diethylsulfamoylphenyl, 2-nitro-4-di-n-butylsulfamoylphenyl, 2-nitro-4-di-n-octylsulfamoylphenyl, 2-nitro-4-di-n-octadecylsulfamoylphenyl, 2-nitro-4-methylsulfamoylphenyl, 2-nitro-4-n-hexadecylsulfamoylphenyl, 2-nitro-4-N-methyl-N-(4-dodecylsulfonylphenyl)sulfamoylphenyl, 2-nitro-4-(3-methylsulfamoylphenyl)sulfamoylphenyl, 4-nitro-2-N-methyl-N-n-butylsulfamoylphenyl, 4-nitro-2-N-methyl-N-n-octylsulfamoylphenyl, 4-nitro-2-N-methyl-N-n-dodecylsulfamoylphenyl, 4-nitro-2-N-methyl-N-n-hexadecylsulfamoylphenyl, 4-nitro-2-N-methyl-N-n-octadecylsulfamoylphenyl, 4-nitro-2-N-methyl-N-(3-carboxypropyl)sulfamoylphenyl, 4-nitro-2-N-ethyl-N-(2-sulfoethyl)sulfamoylphenyl, 4-nitro-2-

N-n-hexadecyl-N-(3-sulfopropyl)sulfamoylphenyl, 4-nitro-2-N-(2-cyanoethyl)-N-[(2-hydroxyethoxy)ethyl]sulfamoylphenyl, 4-nitro-2-diethylsulfamoylphenyl, 4-nitro-2-di-n-butylsulfamoylphenyl, 4-nitro-2-di-n-octylsulfamoylphenyl, 4-nitro-2-di-n-octadecylsulfamoylphenyl, 4-nitro-2-methylsulfamoylphenyl, 4-nitro-2-n-hexadexylsulfamoylphenyl, 4-nitro-2-N-methyl-N-(4-dodecylsulfonylphenyl)sulfamoylphenyl, 4-nitro-2-(3-methylsulfamoylphenyl)sulfamoylphenyl, 4-nitro-2-chlorophenyl, 2-nitro-4-chlorophenyl, 2-nitro-4-N-methyl-N-n-butylcarbamoylphenyl, 2-nitro-4-N-methyl-N-n-octylcarbamoylphenyl, 2-nitro-4-N-methyl-N-n-dodecylcarbamoylphenyl, 2-nitro-4-N-methyl-N-n-hexadecylcarbamoylphenyl, 2-nitro-4-N-methyl-N-n-octadecylcarbamoylphenyl, 2-nitro-4-N-methyl-N-(3-carboxypropyl)carbamoylphenyl, 2-nitro-4-N-ethyl-N-(2-sulfoethyl)carbamoylphenyl, 2-nitro-4-N-n-hexadecyl-N-(3-sulfopropyl)carbamoylphenyl, 2-nitro-4-N-(2-cyanoethyl)-N-[(2-hydroxyethoxy)ethyl]carbamoylphenyl, 2-nitro-4-diethylcarbamoylphenyl, 2-nitro-4-di-n-butylcarbamoylphenyl, 2-nitro-4-di-n-octylcarbamoylphenyl, 2-nitro-4-di-n-octadecylcarbamoylphenyl, 2-nitro-4-methylcarbamoylphenyl, 2-nitro-4-n-hexadecylcarbamoylphenyl, 2-nitro-4-N-methyl-N-(4-dodecylsulfonylphenyl)carbamoylphenyl, 2-nitro-4-(3-methylsulfamoylphenyl)carbamoylphenyl, 4-nitro-2-N-methyl-N-n-butylcarbamoylphenyl, 4-nitro-2-N-methyl-N-n-octylcarbamoylphenyl, 4-nitro-2-N-methyl-N-n-dodecylcarbamoylphenyl, 4-nitro-2-N-methyl-N-n-hexadecylcarbamoylphenyl, 4-nitro-2-N-methyl-N-n-octadecylcarbamoylphenyl, 4-nitro-2-N-methyl-N-(3-carboxypropyl)carbamoylphenyl, 4-nitro-2-N-ethyl-N-(2-sulfoethyl)carbamoylphenyl, 4-nitro-2-N-n-hexadecyl-N-(3-sulfopropyl)carbamoylphenyl, 4-nitro-2-N-(2-cyanoethyl)-N-[(2-hydroxyethoxy)ethyl]carbamoylphenyl, 4-nitro-2-diethylcarbamoylphenyl, 4-nitro-2-di-n-butylcarbamoylphenyl, 4-nitro-2-di-n-octylcarbamoylphenyl, 4-nitro-2-di-n-octadecylcarbamoylphenyl, 4-nitro-2-methylcarbamoylphenyl, 4-nitro-2-n-hexadecylcarbamoylphenyl, 4-nitro-2-N-methyl-N-(4-dodecylsulfonylphenyl)carbamoylphenyl, 4-nitro-2-(3-methylsulfamoylphenyl)carbamoylphenyl, 2,4-dimethanesulfonylphenyl, 2-methanesulfonyl-4-benzenesulfonylphenyl, 2-n-octanesulfonyl-4-methanesulfonylphenyl, 2-n-tetradecanesulfonyl-4-methanesulfonylphenyl, 2-n-hexadecanesulfonyl-4-methanesulfonylphenyl, 2,4-di-n-dodecanesulfonylphenyl, 2,4didodecanesulfonyl-5-trifluoromethylphenyl, 2-n-decanesulfonyl-4-cyano-5-trifluoromethylphenyl, 2-cyano-4-methanesulfonylphenyl, 2,4,6-tricyanophenyl, 2,4-dicyanophenyl, 2-nitro-4-methanesulfonylphenyl, 2-nitro-4-n-dodecanesulfonylphenyl, 2-nitro-4-(2-sulfoethylsulfonyl)phenyl, 2-nitro-4-carboxymethylsulfonylphenyl, 2-nitro-4-carboxyphenyl, 2-nitro-4-ethoxycarbonyl-5-butoxyphenyl, 2-nitro-4-ethoxycarbonyl-5-n-hexadecyloxyphenyl, 2-nitro-4-diethylcarbamoyl-5-n-hexadecyloxyphenyl, 2-nitro-4-cyano-5-dodecylphenyl, 2,4-dinitrophenyl, 2-nitro-4-n-decylthiophenyl, 3,5-dinitrophenyl, 2-nitro-3,5-dimethyl-4-hexadecanesulfonylphenyl, 4-methanesulfonyl-2-benzene-sulfonylphenyl, 4-n-octanesulfonyl-2-methanesulfonylphenyl, 4-tetradecanesulfonyl-2-methanesulfonylphenyl, 4-n-hexadecanesulfonyl-2-methanesulfonylphenyl, 2,5-didodecanesulfonyl-4-trifluoromethylphenyl, 4-n-decanesulfonyl-2-cyano-5-trifluoromethylphenyl, 4-cyano-2-methanesulonylphenyl, 4-nitro-2-methanesulfonylophenyl, 4-nitro-2-n-dodecanesulfonylphenyl, 4-nitro-2-(2-sufoethylsulfonyl)phenyl, 4-nitro-2-carboxymethylsulfonylphenyl, 4-nitro-2-carboxyphenyl, 4-nitro-2-ethoxycarbonyl-5-n-butoxyphenyl, 4-nitro-2-ethoxycarbonyl-5-n-hexadecyloxyphenyl, 4-nitro-2-diethylcarbamoyl-5n-hexadecyloxyphenyl, 4-nitro-2-cyano-5-n-dodecylphenyl, 4-nitro-2-n-decylthiophenyl, 4-nitro-3,5-dimethyl-2-n-hexadecanesulfonylphenyl, 4-nitronaphthyl, 2,4-dinitronaphthyl, 4-nitro-2-n-octadecylcarbamoylnaphthyl, 4-nitro-2-dioctylcarbamoyl-5-(3-sufobenzenesulfonylamino)naphthyl, 2,3,4,5,6-pentafluorophenyl, 2-nitro-4-benzoylphenyl, 2,4-diacetylphenyl, 2-nitro-4-trifluoromethylphenyl, 4-nitro-2-trifluoromethylphenyl, 4-nitro-3-trifluoromethylphenyl, 2,4,5-tricyanophenyl, 3,4-dicyanophenyl, 2-chloro-4,5-dicyanophenyl, 2-bromo-4,5-dicyanophenyl, 4-methanesulfonylphenyl, 4-n-hexadecanesulfonylphenyl, 2-decanesulfonyl-5-trifluoromethylphenyl, 2-nitro-5-methylphenyl, 2-nitro-5-n-octadecyloxyphenyl, 2-nitro-4-N-(vinylsulfonylethyl)-N-methylsulfamoylphenyl, and 2-methyl-6-nitrobenzoxazol-5-yl groups.

Specific examples of the heterocyclic group are 2-pryridyl, 3-pyridyl, 4-pyridyl, 5-nitro-2-pyridyl, 5-nitro-N-hexadecylcarbamoyl-2-pyridyl, 3,5-dicyano-2-pyridyl, 5-dodecanesulfonyl-2-pyridyl, 5-cyano-2-pyrazyl, 4-nitrothiophen-2-yl, 5-nitro-1,2-dimethylimidazol-4-yl, 3,5-diacetyl-2-pyridyl, 2-dodecyl-5-carbamoylpyridinium-2-yl, 5-nitro-2-furyl, and 5-nitrobenzothiazol-2-yl groups.

The group represented by ─(Time)$_t$─PUG is now described in greater detail.

Time represents a group capable of releasing PUG through a subsequent reaction to after cleavage of a nitrogen-oxygen bond, a nitrogen-nitrogen bond or a nitrogen-sulfur bond as a trigger.

Varius known groups, e.g., those described in Japanese Patent Application (OPI) Nos. 147244/86 (pp. 5–6) and 236549/86 (pp. 8–14), and European Pat. No. 220,746 A2 (pp. 11–22) can be applied to Time.

Specific examples of moieties preferred as Time are illustrated below. Herein, the mark (*) indicates the site at which the moiety is attached to PWR in general formula (I), or at which it is attached to any of the groups as indicated by dashed lines in general formula (II) or (III), and the mark (*)(*) indicates the site at which the moiety is attached to PUG.

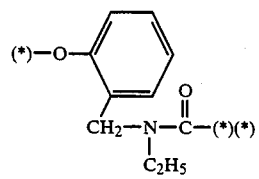

(1)

-continued
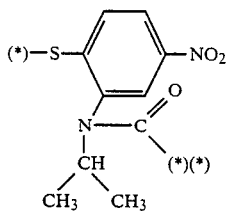
(2)
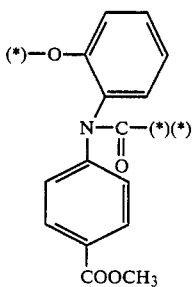
(3)
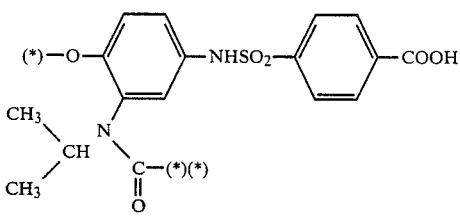
(4)
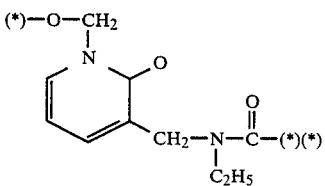
(5)
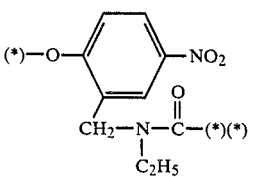
(6)
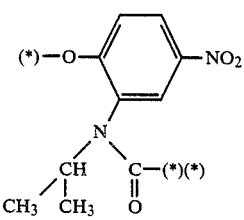
(7)
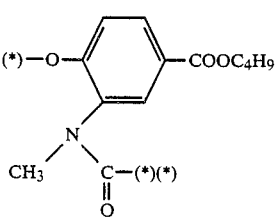
(8)

-continued
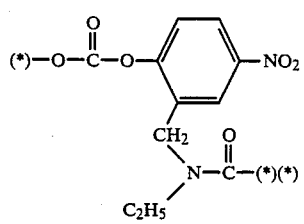
(9)
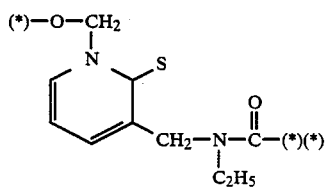
(10)
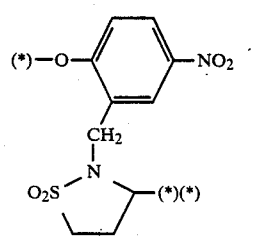
(11)
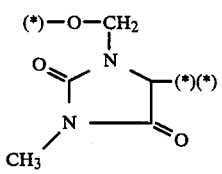
(12)
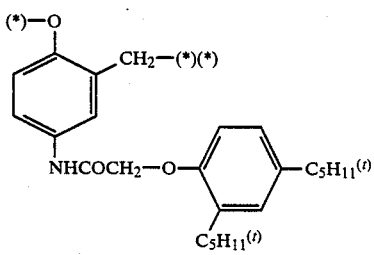
(13)
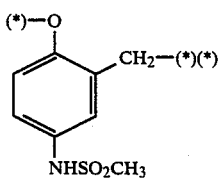
(14)
(15)

-continued
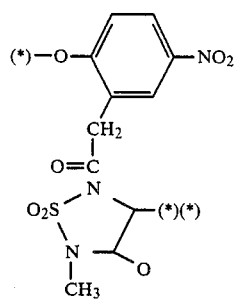
(16)
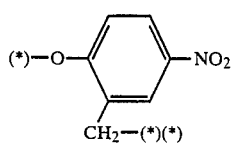
(17)
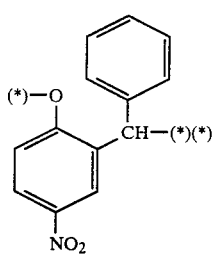
(18)
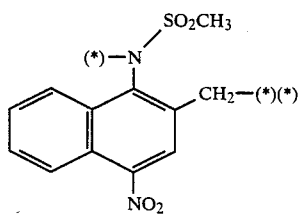
(19)
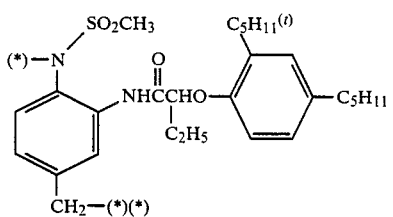
(20)
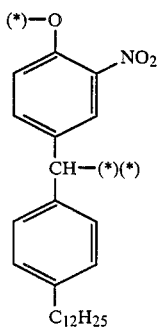
(21)

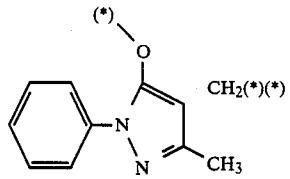
(22)
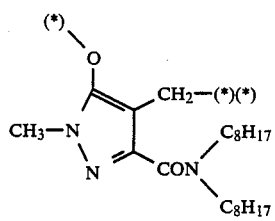
(23)
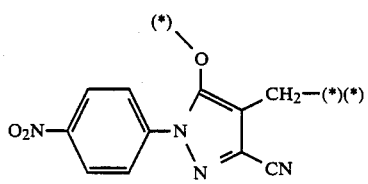
(24)
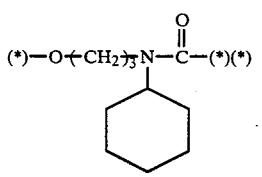
(25)
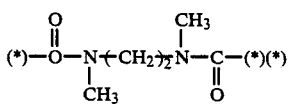
(26)
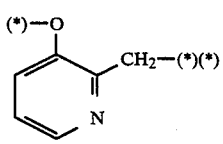
(27)
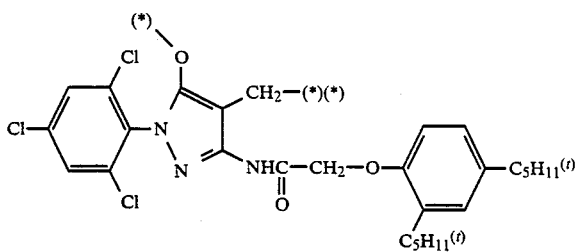
(28)
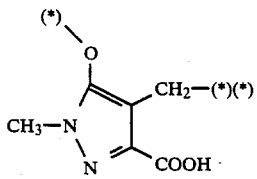
(29)
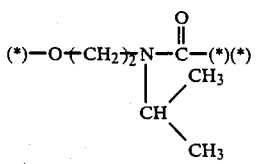
(30)

-continued
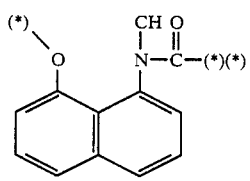 (31)
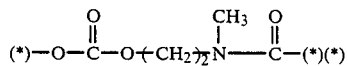 (32)
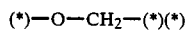 (33)
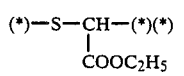 (34)
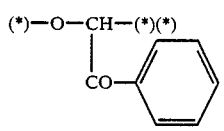 (35)
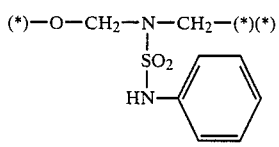 (36)
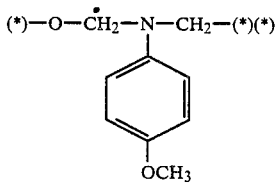 (37)
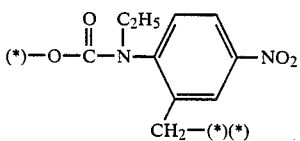 (38)
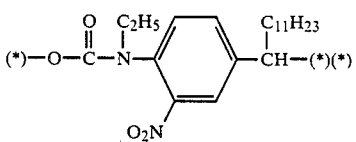 (39)
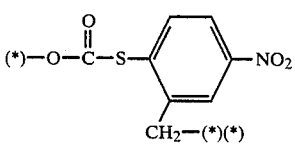 (40)
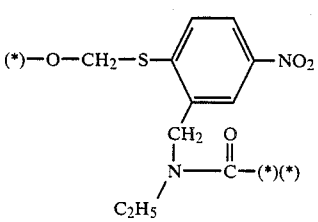 (41)

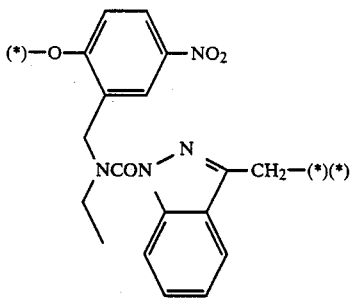
(42)

PUG functions as a photographically useful group in the form of Time-PUG or PUG.

Specific examples of photographically useful groups include development inhibitors, development accelerators, nucleating agents, couplers, diffusible or nondiffusible dyes, desilvering accelerators, desilvering inhibitors, halides, silver halide solvents, redox competitive compounds, developers, auxiliary developers, fixation accelerators, fixation inhibitors, silver image stabilizers, toning agents, processing dependence improvers half-tone improvers, dye image stabilizers, dyes for photographic use, surface active agents, hardeners, desensitizers, high contrast imparting agents, chelating agents, brightening agents, ultraviolet absorbents, nucleation accelerators, and precursors of these agents.

The group represented by PUG has a molecular weight lower than about 1,500.

Specific examples of PUG are described in European Pat. No. 220,746 A2 Japanese Patent Application (OPI) No. 32839/86, and so on.

The representatives of the groups denoted as PUG or ⁻(Time)ₜPUG are illustrated below. Herein, the mark (*) designates the site at which the group is attached to PWR.

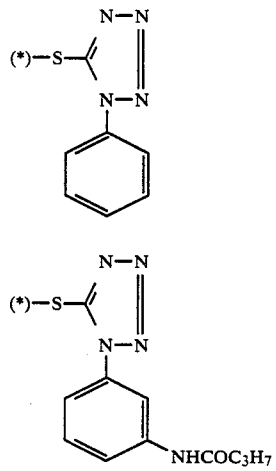

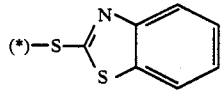

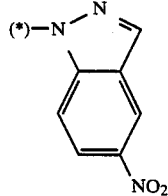

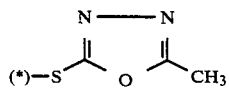

-continued
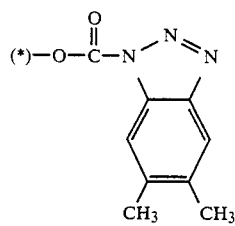
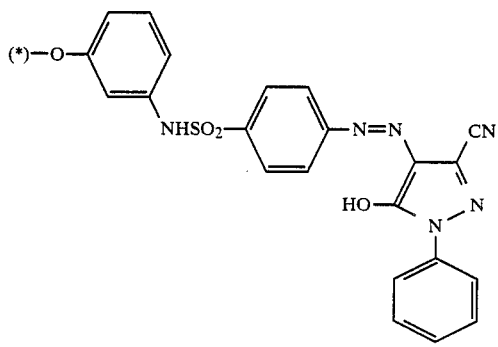
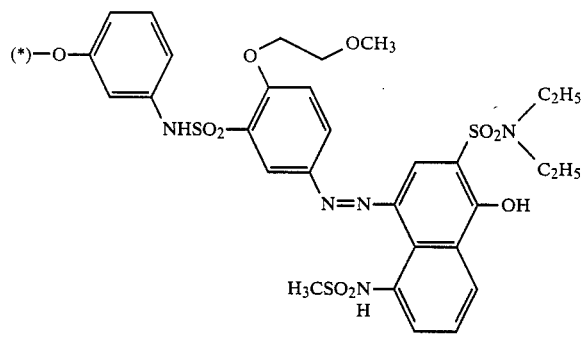
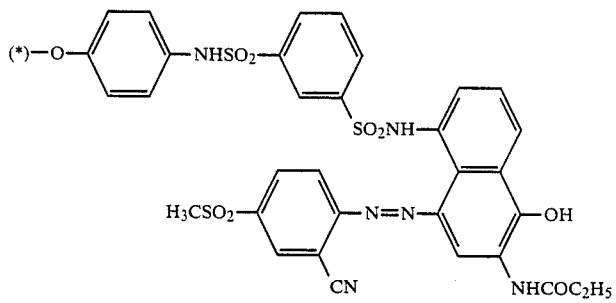
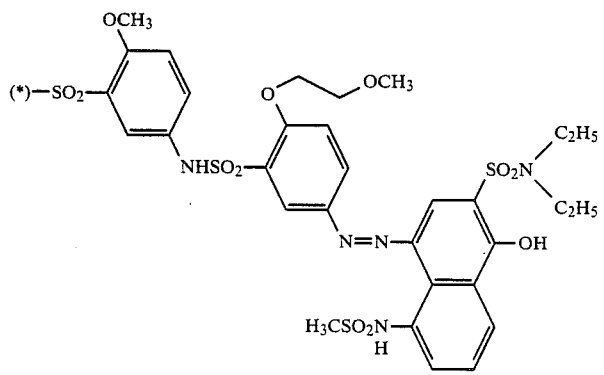

-continued
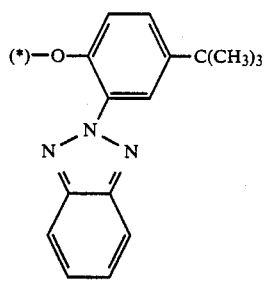
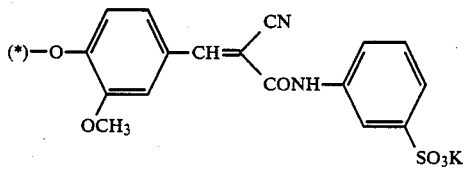
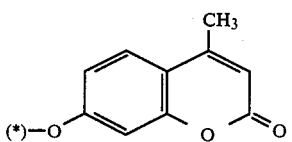
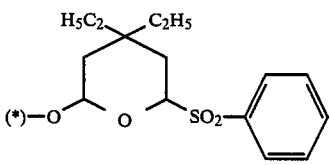
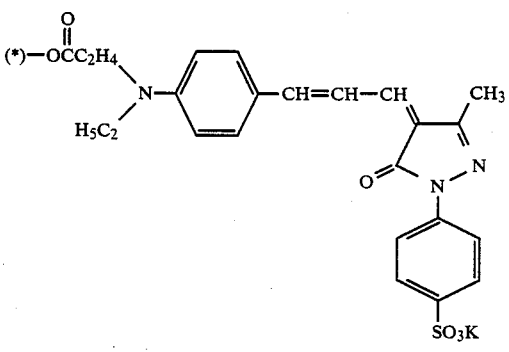
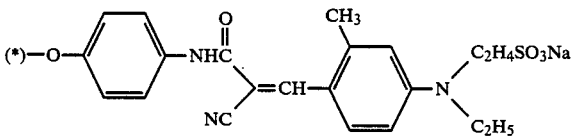
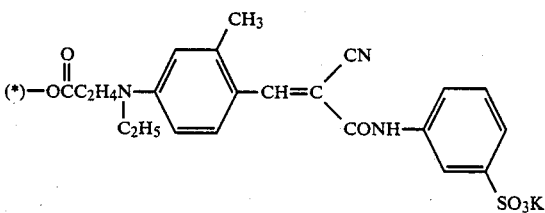

-continued

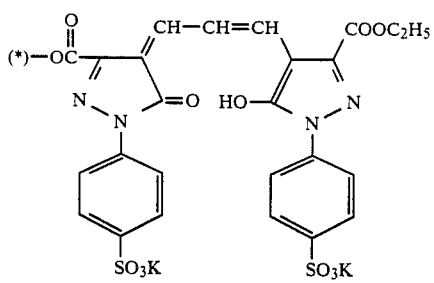

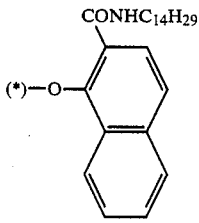

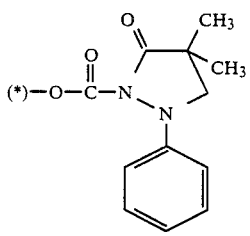

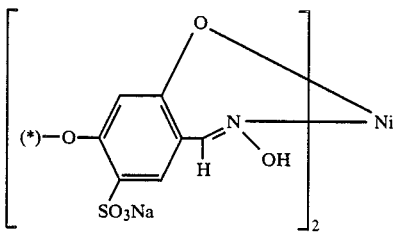

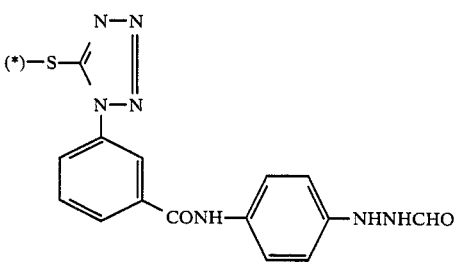

The polymers of the present invention (referred to as "high molecular compounds" below) are now described in greater detail.

The polymers of the present invention are synthetic and preferred polymers in the present invention are represented by formula (IV):

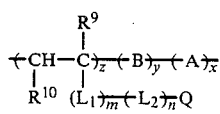

(IV)

In the above formula, $R^9$ represents a hydrogen atom or a substituted or unsubstituted alkyl group containing 1 to 6 carbon atoms, and $R^{10}$ represents a hydrogen atom or —COOR$^9$ (wherein $R^9$ has the same meaning as above). $L_1$ represents an alkylene group containing 1 to 6 carbon atoms, an arylene group containing 6 to 10 carbon atoms, an arylenealkylene group containing 7 to 11 carbon atoms, —COO—, —OCO—, or —CONR$^{11}$—, wherein $R^{11}$ represents a hydrogen atom, or a substituted or unsubstituted alkyl group containing 1 to 4 carbon atoms; and $L_2$ represents a group connecting $L_1$ to Q. m and n each represents 0 or 1. Q represents a group formed by eliminating a hydrogen atom from the compound represented by formula (I) at the PWR or Time position, which is attached to $-(L_1)_m-(L_2)_n-$.

B represents a monomer unit obtained by copolymerization of monomers having an ethylenically unsaturated group, and A represents a monomer unit obtained by copolymerization of monomers having at least two ethylenically unsaturated groups, at least one of which is contained in a side chain.

x, y and z each represents a percentage by weight, and x ranges from 0 to about 20, y from 0 to about 80, and z from about 20 to 100.

A suitable divalent linking group represented by $L_2$ in formula (IV) is represented by $+X_1+J_1-X_2+_p+J_2-X_3+_q+J_3+_r]_n$, wherein, $J_1$, $J_2$ and $J_3$, which may be the same or different, each represents

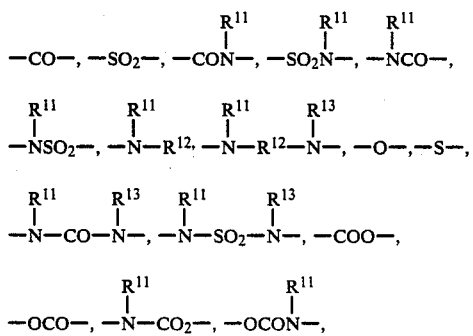

or so on, wherein $R^{11}$ has the same meaning as in formula (IV); $R^{12}$ represents an alkylene group containing from 1 to about 4 carbon atoms; $R^{13}$ represents a hydrogen atom or a substituted or unsubstituted alkyl group containing 1 to 6 carbon atoms.

$X_1$, $X_2$ and $X_3$, which may be the same or different, each represents an unsubstituted alkylene group, a substituted alkylene group, an unsubstituted arylene group, a substituted arylene group, an unsubstituted aralkylene group, or a substituted aralkylene group. p, q, r and n each represents 0 or 1.

Examples of substituent groups for the foregoing divalent linking group $L_2$ include halogen atoms, nitro groups, cyano groups, unsubstituted and substituted alkyl groups, unsubstituted and substituted alkoxy groups, an amino group which may be substituted with an alkyl group, a hydroxyl group, a group capable of producing a hydroxyl group by hydrolysis, groups represented by $-NHCOR^{14}$, $-NHCOR^{14}$, $-SOR^{14}$, $-SO_2R^{14}$, $-COR^{14}$, $-CONR^{15}R^{16}$, or $-SO_2NR^{15}R^{16}$, wherein $R^{14}$ represents an unsubstituted or substituted alkyl group, an unsubstituted or substituted phenyl group, or an unsubstituted or substituted aralkyl group, and $R^{15}$ and $R^{16}$, which may be the same or different, each represents a hydrogen atom, an unsubstituted or substituted alkyl group, an unsubstituted or substituted phenyl group, or an unsubstituted or substituted aralkyl group.

Suitable examples of substituent groups for the further substituted substituent groups of $L_2$ (including substituted alkyl, alkoxy, phenyl and aralkyl groups) include a hydroxyl group, a nitro group, alkoxy groups containing 1 to about 4 carbon atoms, groups represented by $-NHSO_2R^{14}$, groups represented by $-NHCOR^{14}$, groups represented by $-SO_2R^{15}R^{16}$, groups represented by $-CONR^{15}R^{16}$, groups represented by $-SO_2R^{14}$, groups represented by $-COR^{14}$, wherein $R^{14}$, $R^{15}$ and $R^{16}$ each has the same meaning as described above; halogen atoms, cyano groups, substituted or unsubstituted amino groups (which may be substituted with an alkyl group), and so on. B is a monomer unit in which copolymerizable ethylenically unsaturated monomers are copolymerized, and preferred examples of ethylenically unsaturated monomers include ethylene, propylene, 1-butene, isobutene, styrene, α-methylstyrene, vinyltoluene, monoethylenically unsaturated esters of aliphatic acids (such as vinyl acetate, allyl acetate, etc.), esters of ethylenically unsaturated mono- or di-carboxylic acids (such as methylmethacrylate, ethylacrylate, n-butylacrylate, n-butylmethacrylate, n-hexylmethacrylate, n-octylacrylate, benzylacrylate, cyclohexylmethacrylate, 2-ethylhexylacrylate, etc.), monoethylenically unsaturated compounds (such as acrylonitrile, methacrylonitrile, etc.), dienes (such as butadiene, isoprene, etc.), and so on.

B may contain two or more of the above-described monomer units.

Preferred copolymerizable monomers having at least two ethylenically unsaturated groups, which are represented by A, include divinylbenzene, ethylene glycol dimethacrylate, isopropylene glycol dimethacrylate, neopentyl glycol dimethacrylate, tetramethylene glycol diacrylate and tetramethylene glycol dimethacrylate. Among these monomers, divinylbenzene and ethylene glycol dimenthacrylate are particularly preferred.

Another preferred example of the polymer of the present invention is represented by formula (V):

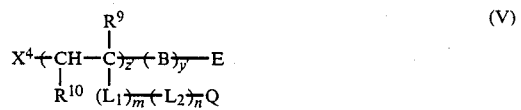

wherein E represents a monovalent group containing at least 8 carbon atoms; $X^1$ represents a hydrogen atoms, or a halogen atom (including F, Cl, Br and I); B, $L_1$, $L_2$, Q, $R^9$, $R^{10}$, m and n each has the same meaning as in formula IV; and y' and z' each represents percentages by weight of the polymerizing components excluding E and $X^4$, the ratio y'/z' ranging from 0/100 to about 90/10.

Suitable examples of a monovalent group containing 8 or more carbon atoms, which is represented by E in the above formula (V), include those represented by formula (B):

wherein $E^1$ represents an unsubstituted alkyl group, substituted alkyl group, substituted aryl group, substituted naphthyl group and so on, which each must contain at least 8 carbon atoms.

Examples of substituents for the foregoing substituted groups represented by $E^1$ may have include halogen atoms; cycano groups; alkyl groups; substituted alkyl groups; alkoxy groups; substituted alkoxy groups; unsubstituted amino groups or amino groups substituted with alkyl group(s); hydroxyl groups or groups capable of producing a hydroxyl group by hydrolysis; $-NHCOR^{1'}$, $-NHSO_2R^{1'}$, $-COOR^{1'}$, $-OCOR^{1'}$, $-SOR^{1'}$, $-CONR^{2'}R^{3'}$, and $-SO_2NR^{2'}R^{3'}$, wherein $R^{1'}$ represents an alkyl group a substituted alkyl group, a phenyl group, a substituted phenyl group, or an aralkyl group and $R^{2'}$ and $R^{3'}$, which may be the same or different, each represents hydrogen atom, alkyl group, a substituted alkyl group, a phenyl group, a substituted phenyl group, an aralkyl group, or a substituted aralkyl group.

Suitable examples of substituents for the foregoing substituted alkyl, alkoxy, phenyl and aralkyl group substituents of $E^1$ include hydroxyl groups, alkoxy groups containing 1 to about 4 carbon atoms; halogen atoms, cyano groups, unsubstituted amino groups; amino groups substituted with alkyl group(s); —NHSO$_2$R$^{1'}$, —NHCOR$^{1'}$, —COOR$^{1'}$, —OCOR$^{1'}$, —SO$_2$NR$^{2'}$R$^{3'}$; —CONR$^{2'}$R$^{3'}$, —SO$_2$R$^{1'}$, and —COR$^{1'}$, wherein R$^{1'}$, R$^{2'}$ and R$^{3'}$ each has the same meaning as described above, and so on.

Preferred examples of groups represented by E$^1$ are illustrated below. However, the invention should is not to be construed as being limited to these examples.

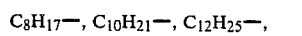

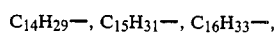

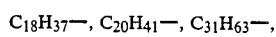

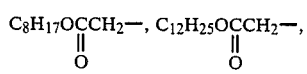

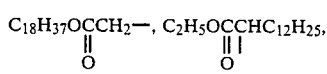

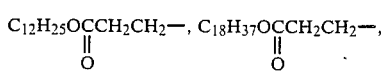

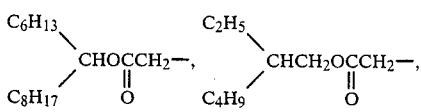

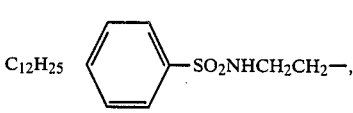

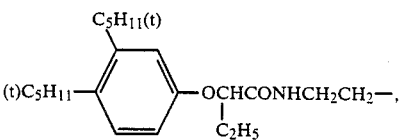

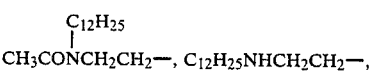

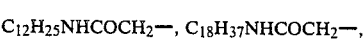

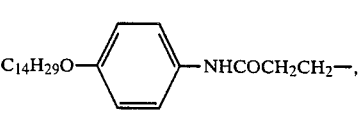

-continued

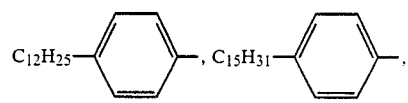

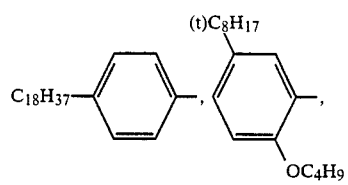

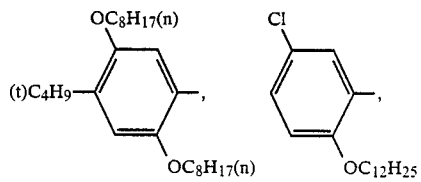

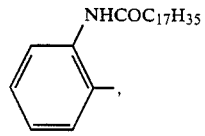

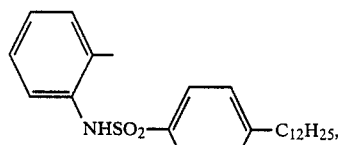

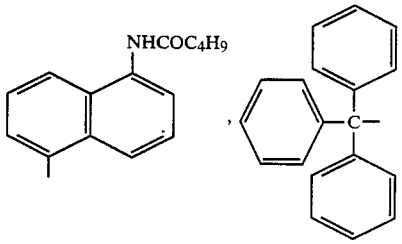

Y$^1$ in formula (B) represents —O—, —S—, —SO—, or —SO$_2$—, particularly preferably —S—, —SO—, or —SO$_2$—, and p is 0 is 1.

Still another preferred example of the polymer of the present invention is represented by the formula (VI):

$$+M-L^3+ \qquad (VI)$$

wherein M represents a divalent group containing a moiety formed by eliminating a hydrogen atom from the compound represented by formula (I) at the PWR or Time position thereof, and L$^3$ represents a divalent group capable of forming the main chain of a macromolecule together with M.

More specifically, M represents a divalent group derived from a compound containing a moiety formed by eliminating a hydrogen atom from the compound represented by formula (I) at the PWR or Time position, and containing at least two carboxyl, amino or hydroxyl groups, and L$^3$ represents a divalent group derived from a compound containing not less than two isocyanate, carboxyl, amino or hydroxyl groups.

It is preferred that the compounds represented by formula (VI) should have two functional groups.

High molecular compounds derived from bifunctional low molecular compounds, which are represented by formula (VI), include polyamides prepared by polycondensation reaction of diamines and dicarboxylic acids (or acid chlorides, polyurethanes prepared by polyaddition reaction of diols and diisocyanates, polyureas prepared by polyaddition reaction of diamines and diisocyanates, polyesters prepared by polycondensation reaction of diols and dicarboxylic acids (or acid chlorides), and so on.

As the raw materials for synthesis of the polymer represented by formula (VI), two or more compounds may be employed for each of the constitutents M and $L^3$.

Also, high molecular compounds can be obtained by using two or more low molecular compounds, which differ in functional group, as each of the constituents M and $L^3$.

For example, a high molecular compound can be prepared by using two kinds of low molecular compounds, a diamine and a dicarboxylic acid, as raw materials of M, and similarly using two kinds of low molecular compounds, a diamine and a dicarboxylic acid, as raw materials of $L^3$.

Specific examples of preferred monomer units which contain a group derived from the compound of formula (I) in accordance with the present invention, and constitute the high molecular compounds represented by formulae (IV) and (V) are illustrated below. However, the present invention is not to be construed as being limited to these examples.

The mark (*) in the following formulae shows the site at which the exemplified monomer is connected to $-(\text{Time})_t-\text{PUG}$. However, a hetero atom situated at the position marked as (*) in the foregoing examples of Time or PUG is omitted when a hetero atom is present at the site of (*), such as (*)—O—, (*)—S— or $$(*)-\underset{|}{N}-.$$

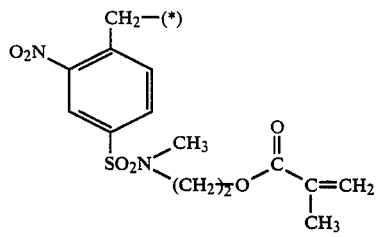

V-1

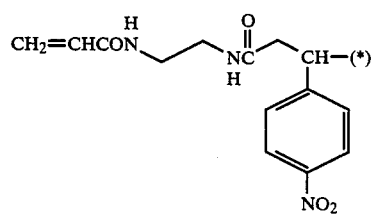

V-2

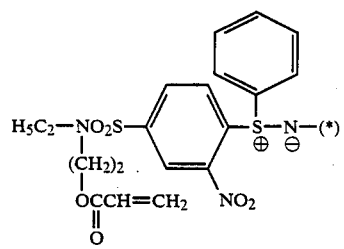

V-3

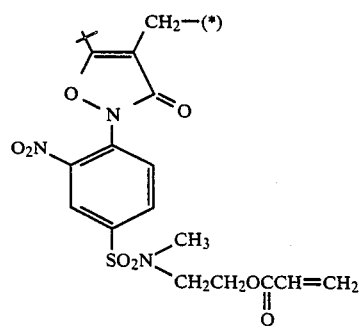

V-4

-continued
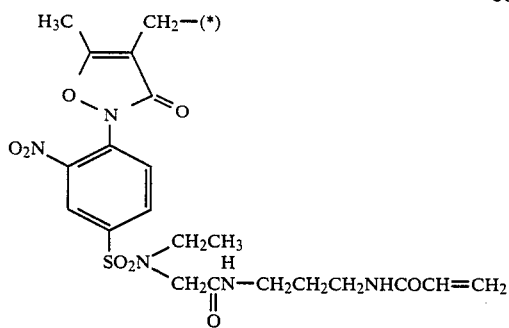
V-5
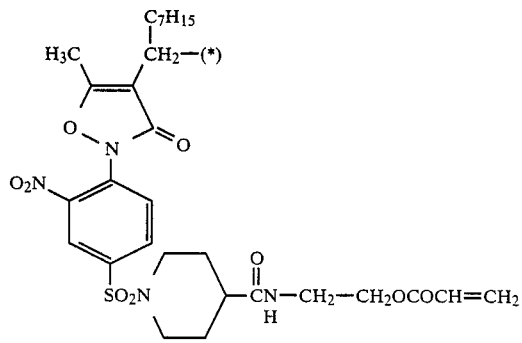
V-6
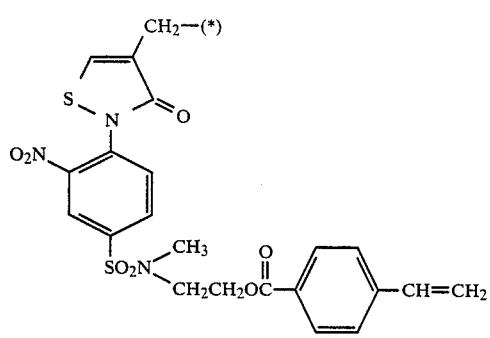
V-7
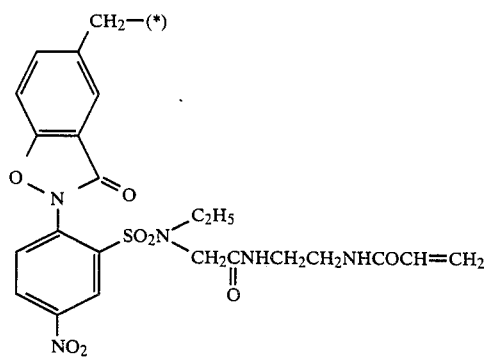
V-8
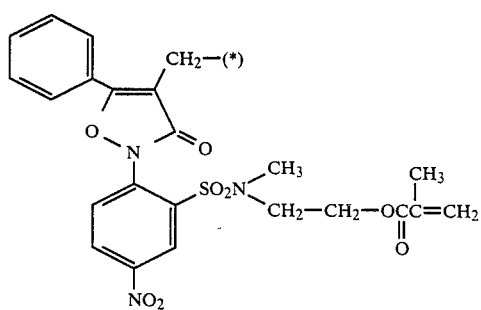
V-9

-continued
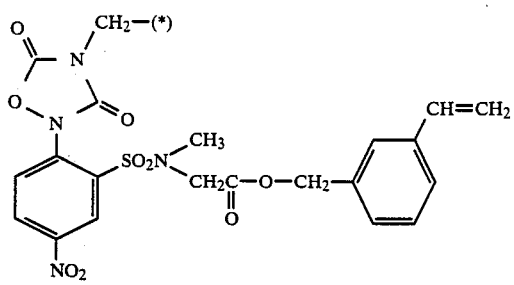 V - 10
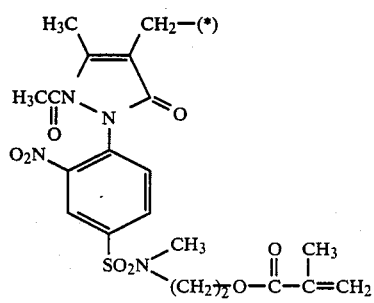 V - 11
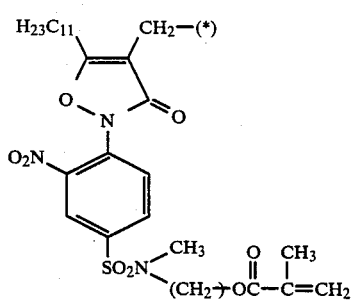 V - 12
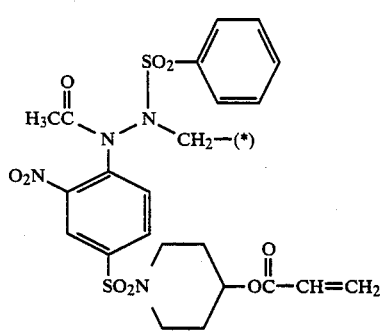 V - 13
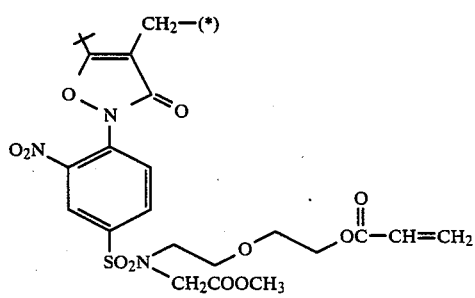 V - 14

-continued
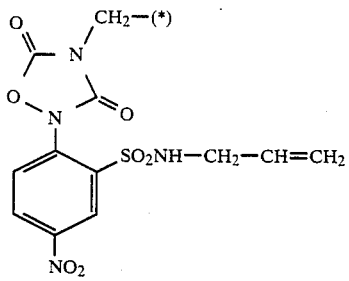 V - 15
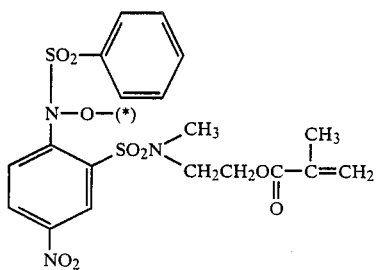 V - 16
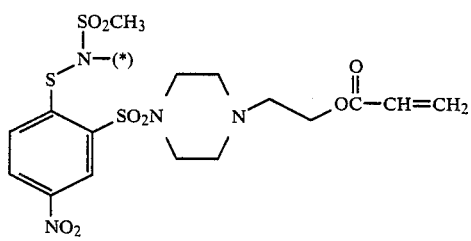 V - 17
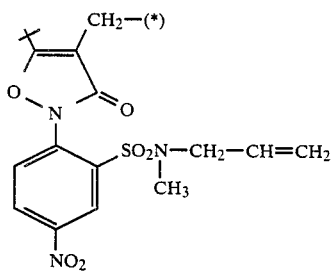 V - 18
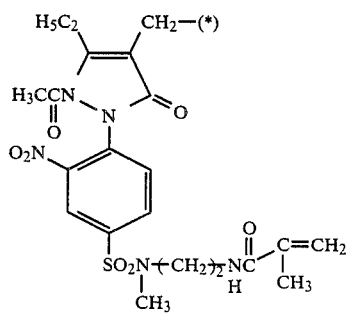 V - 19

-continued
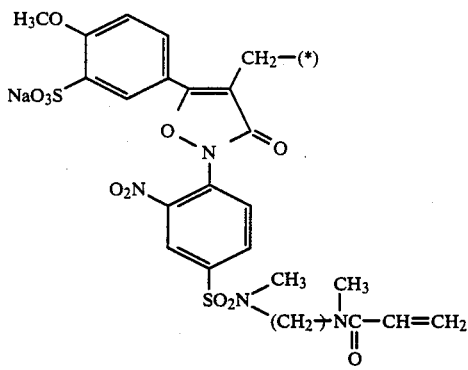
V-20
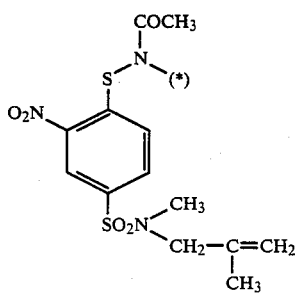
V-21
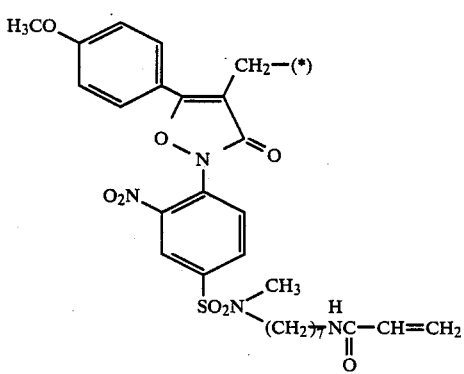
V-22
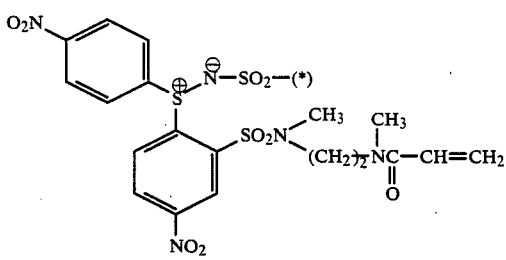
V-23
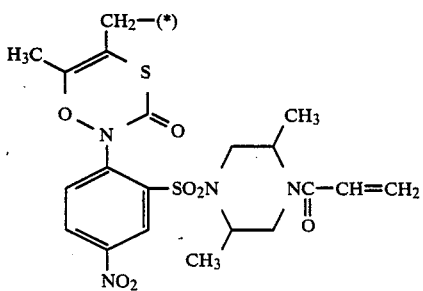
V-24

-continued
V - 25
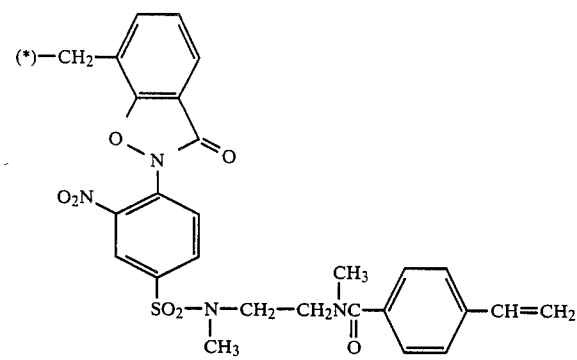
V - 26
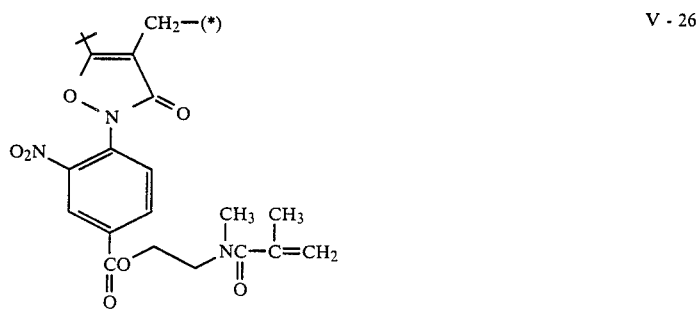
V - 27
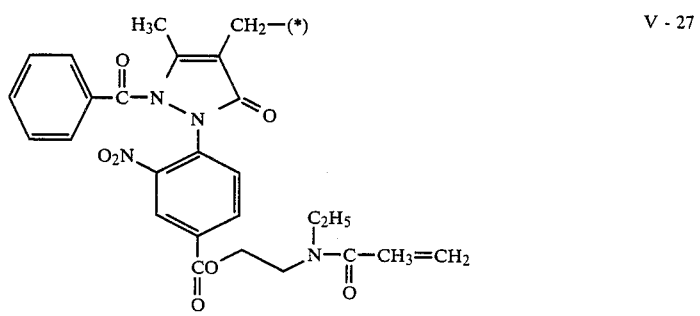
V - 28
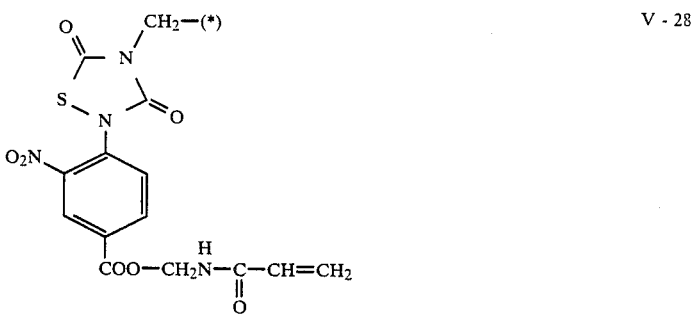
V - 29
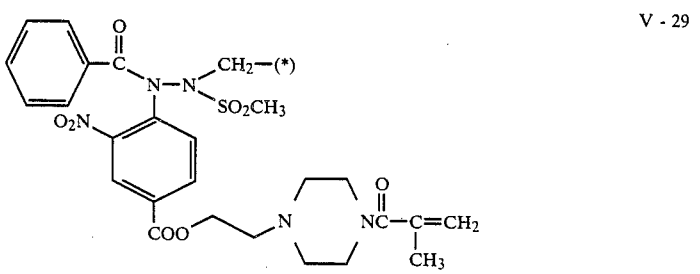

-continued
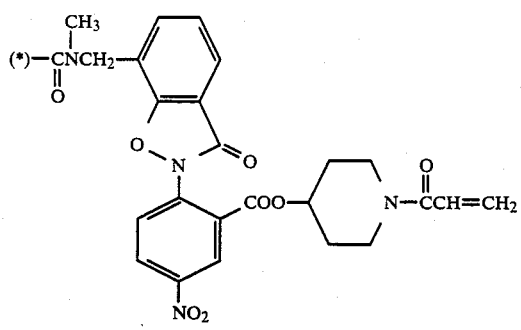
V - 30
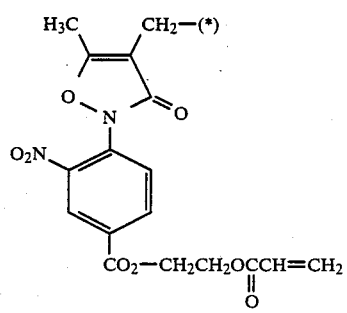
V - 31
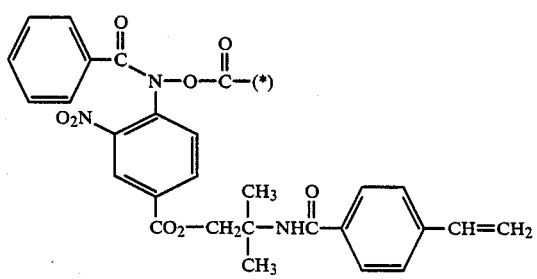
V - 32
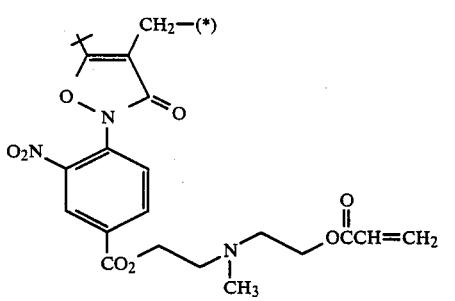
V - 33
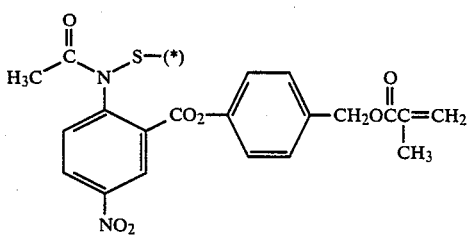
V - 34

-continued
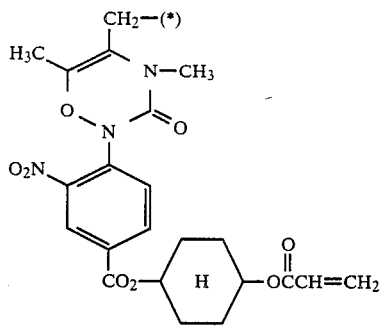
V-35
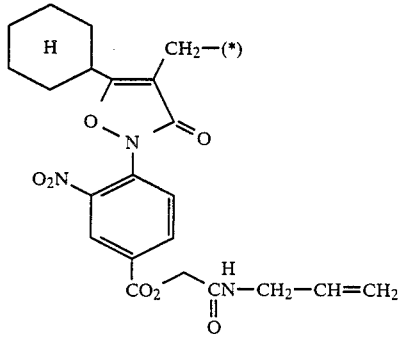
V-36
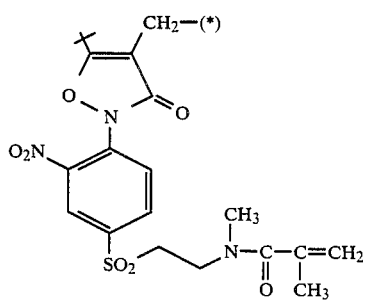
V-37
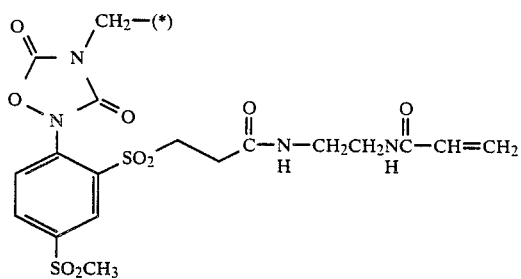
V-38
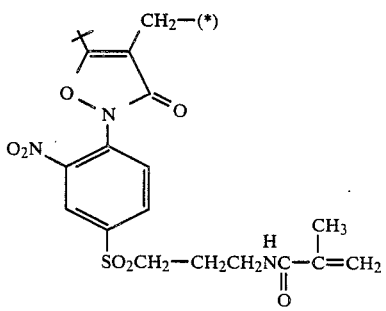
V-39

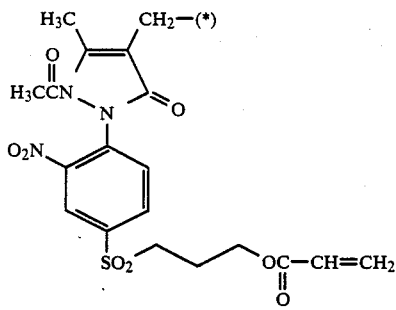

V - 40

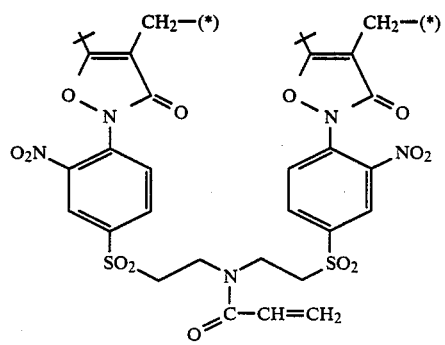

V - 41

Specific examples of a preferred divalent group M in formula (VI) are illustrated below. However, the compounds of the present invention are not to be construed as being limited to these examples.

In the following structural formulae, the mark (*) shows the site at which each group is connected to ${\rm +Time+}_t{\rm PUG}$.

However, when the mark (*) is present at the site of a hetero atom, such as (*)—O—, (*)—S— or

the hetero atom located at the (*) position of the foregoing Time or PUG is omitted.

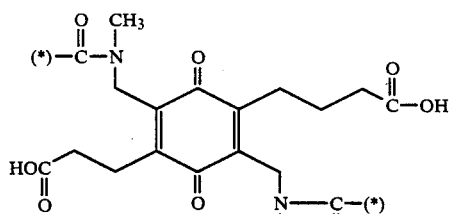

M-1

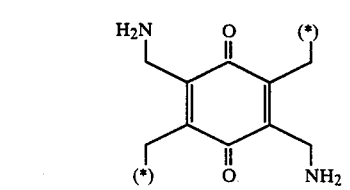

M-2

-continued

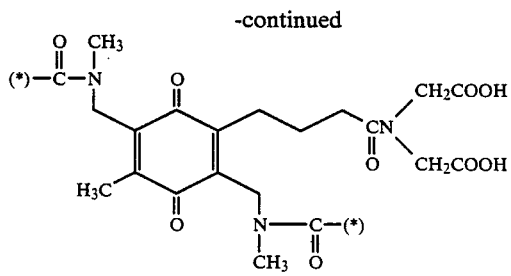

M-3

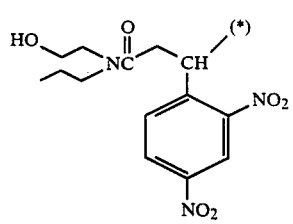

M-4

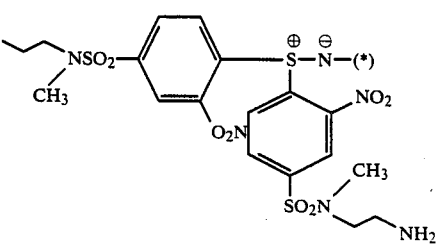

M-5

-continued
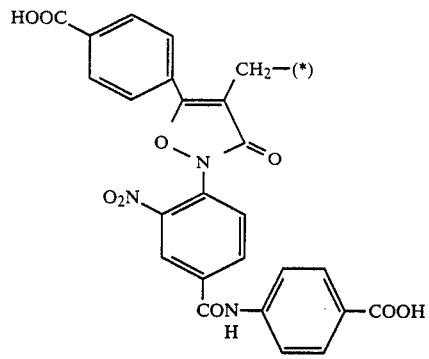
M-6
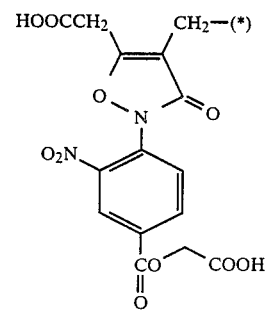
M-7
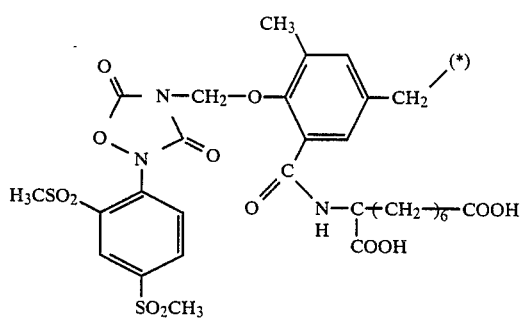
M-8
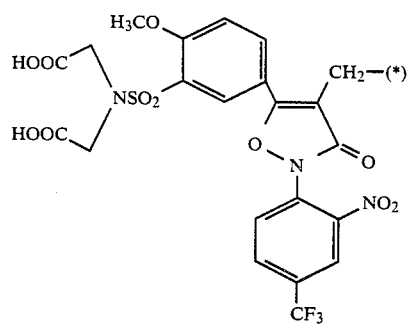
M-9
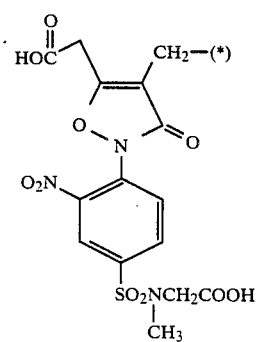
M-10
-continued
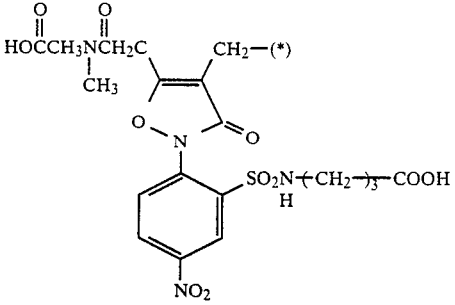
M-11
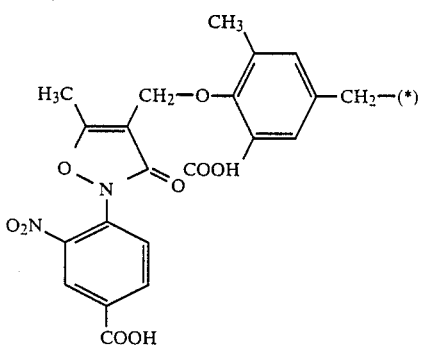
M-12
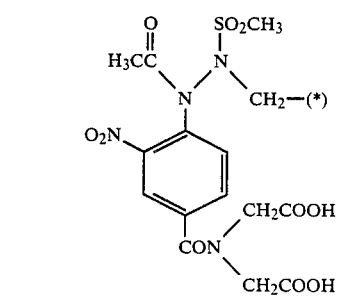
M-13
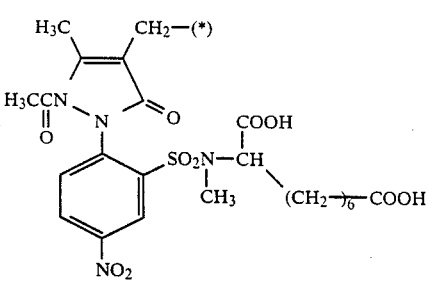
M-14
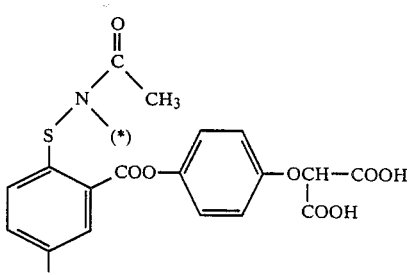
M-15

M-16
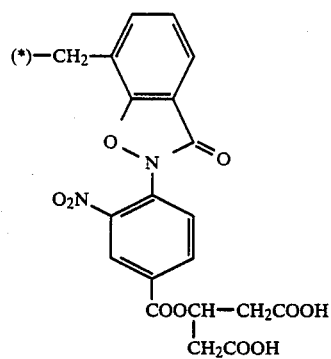
M-17
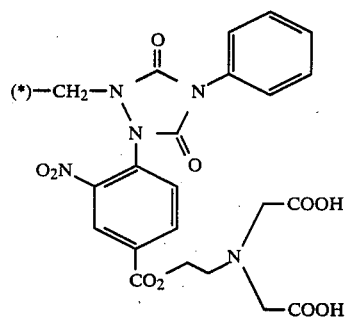
M-18
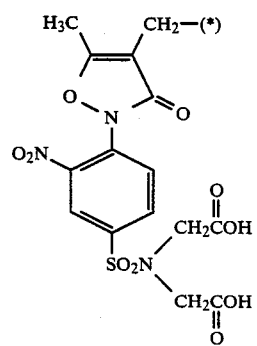
M-19
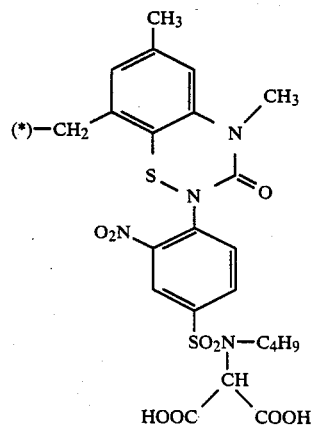
M-20
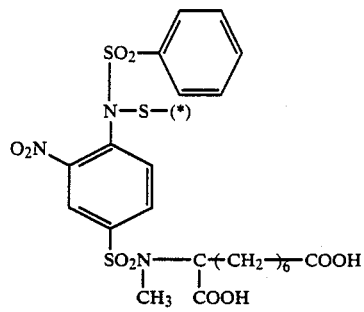
M-21
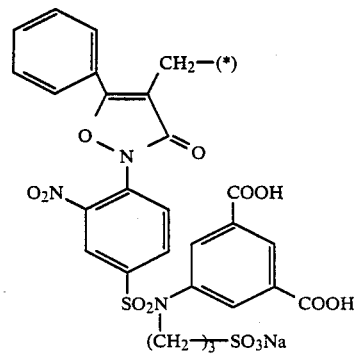
M-22
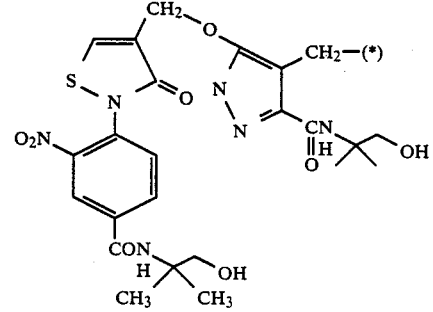
M-23
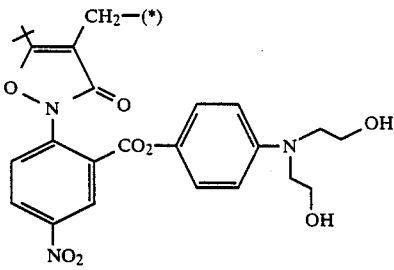
M-24
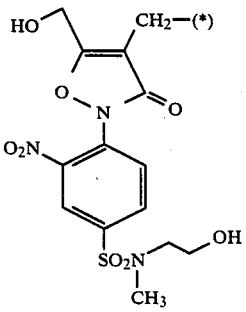

-continued
M-25
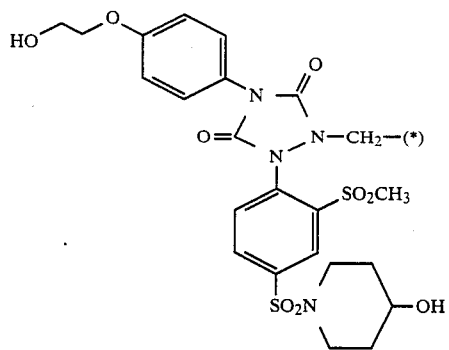
M-26
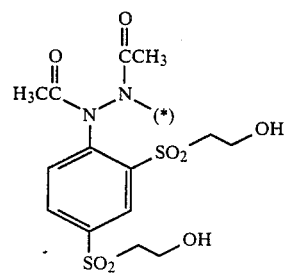
M-27
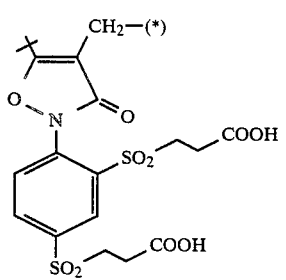
M-28
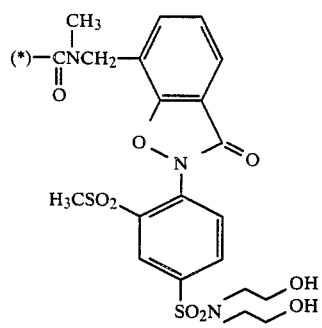
M-29
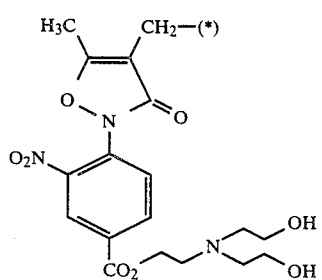
-continued
M-30
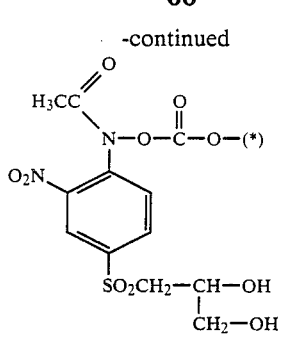
M-31
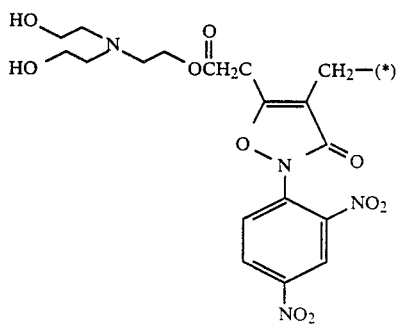
M-32
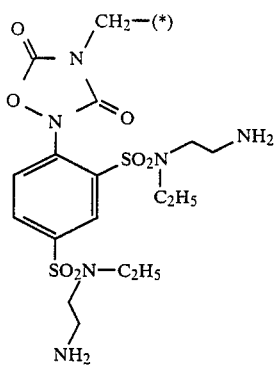
M-33
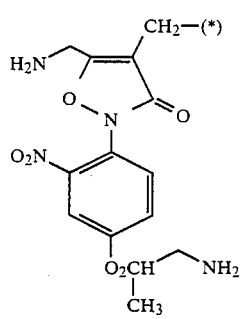
M-34
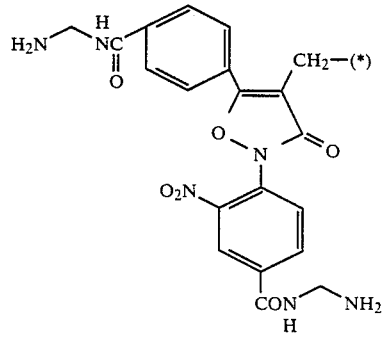

-continued

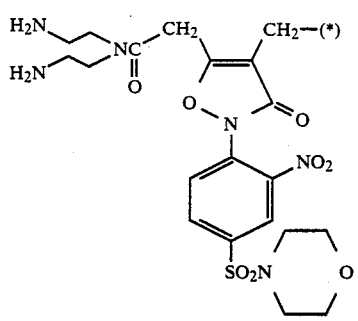 M-35

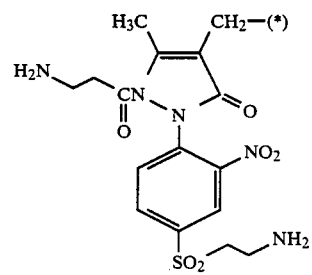 M-36

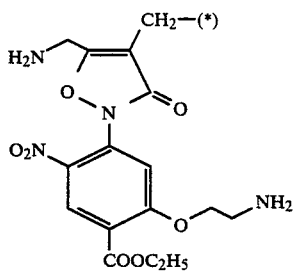 M-37

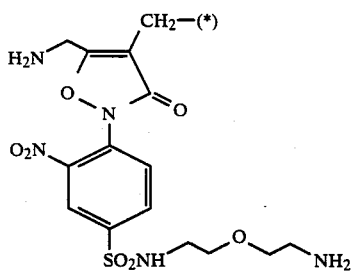 M-38

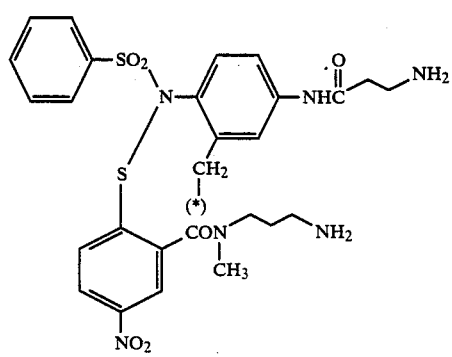 M-39

-continued

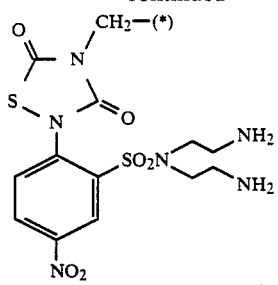 M-40

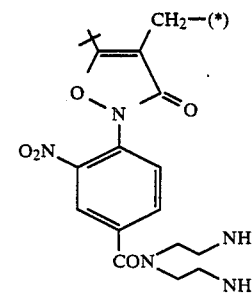 M-41

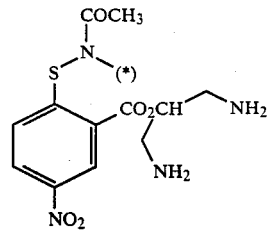 M-42

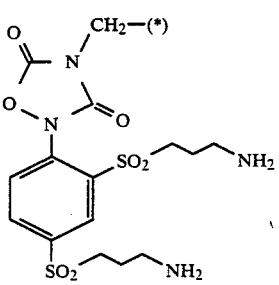 M-43

Now, specific examples of high molecular compounds preferred as polymers of the compound of the present invention, which are represented by formula (IV), are illustrated below. However, the high molecular compounds of the present invention are not to be construed as being limited to these examples.

In the examples (*) shows the site at which each compound is attached to (Time)$_t$PUG, and when the mark (*) is present at the site of a hetero atom, such as (*)—O—, (*)—S— or (*)—N—,
　　| the hetero atom located at the (*) position of the foregoing Time or PUG is omitted.

The term wt/wt or wt/wt/wt in parentheses refers to percentages by weight with respect to the corresponding low molecular compounds.

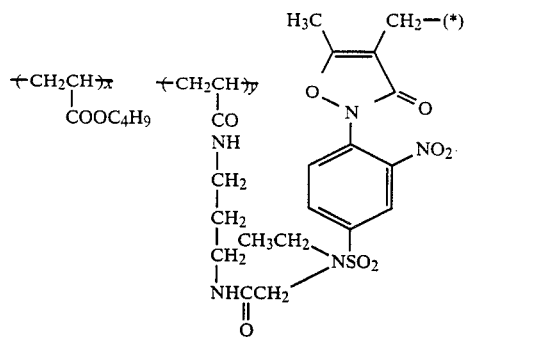
P-1
x/y = 50/50 (wt/wt)
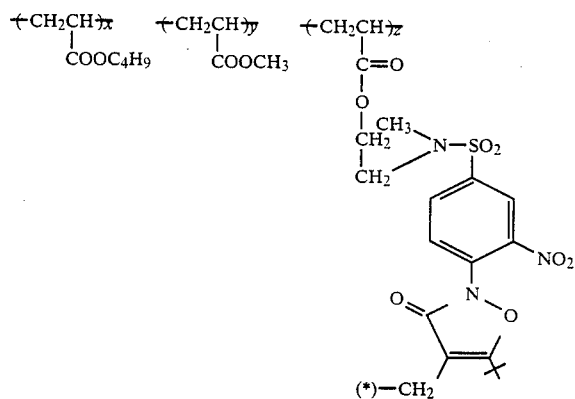
P-2
x/y/z = 30/30/40 (wt/wt/wt)
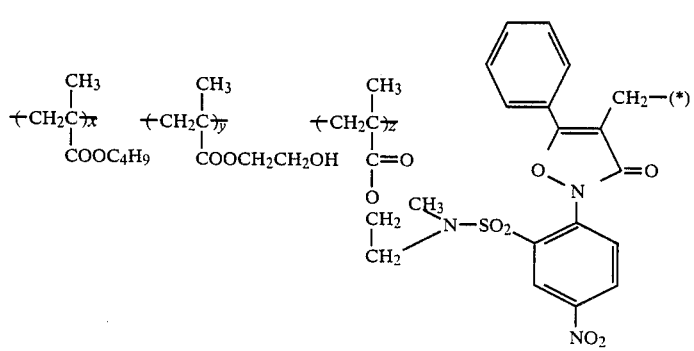
P-3
x/y/z = 20/30/50 (wt/wt/wt)
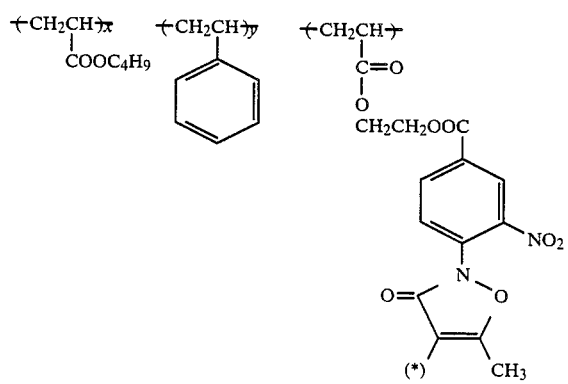
P-4
x/y/z = 20/20/60 (wt/wt/wt)

-continued
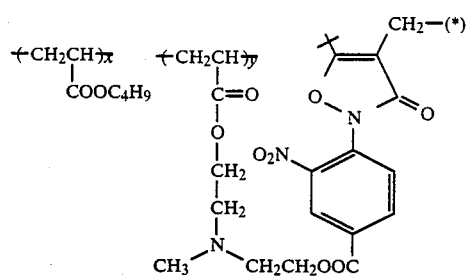
P-5
x/y = 20/80 (wt/wt)
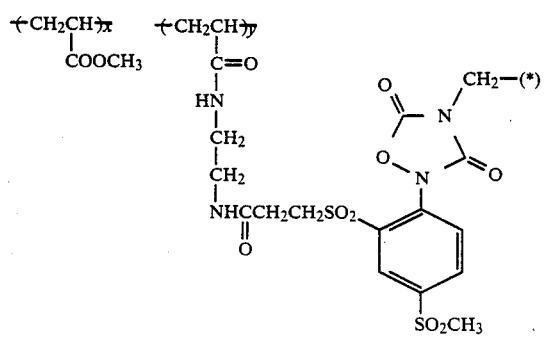
P-6
x/y = 30/70 (wt/wt)
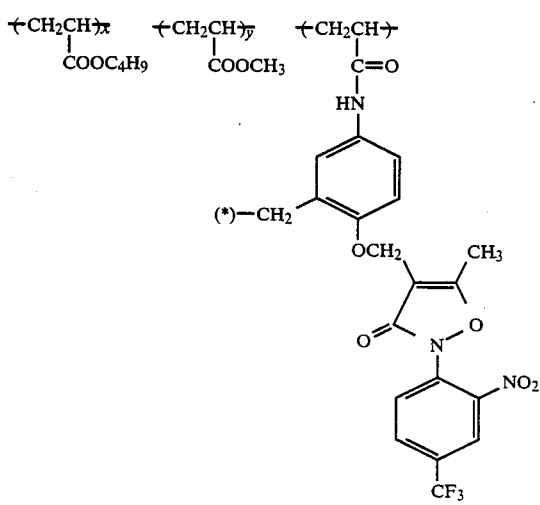
P-7
x/y/z = 25/25/50 (wt/wt/wt)
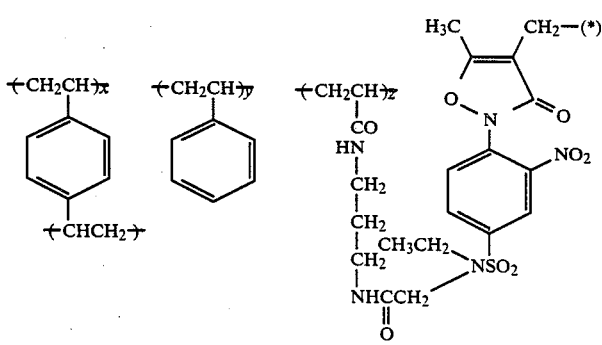
P-8
x/y/z = 2/28/70 (wt/wt/wt)

P-9

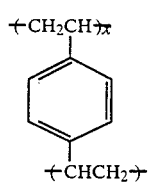 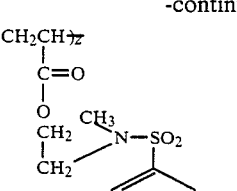

x/y/z = 10/45/45 (wt/wt/wt)

P-10

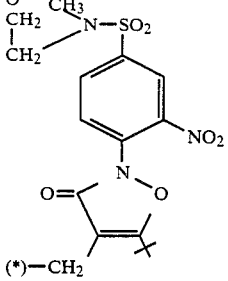

x/y = 5/95 (wt/wt)

P-11

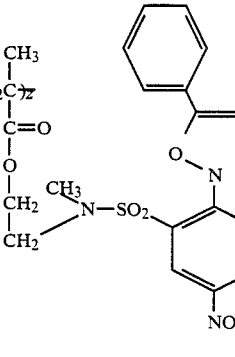

x/y/z = 1/39/60 (wt/wt/wt)

P-12

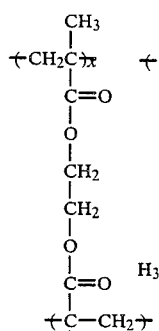 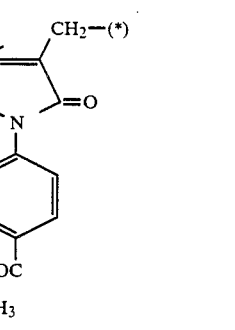

x/y = 8/92 (wt/wt)

In addition, specific examples of high molecular compounds of formula (V) concerned in the present invention are illustrated below. The mark (*) in the following structural formulae has the same meaning as described above. Among respective fractions (by weight) of the constituent elements in each polymer, the weight fraction of every terminal group corresponding to E (e.g., the group $C_{18}H_{37}S-$ in the compound T-1) is designated by x.
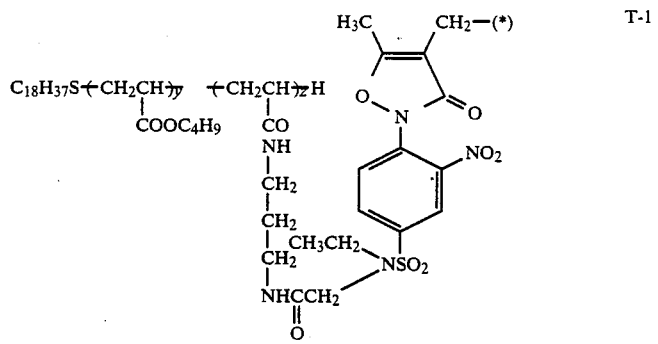
x/y/z = 5/45/50 (wt/wt/wt)
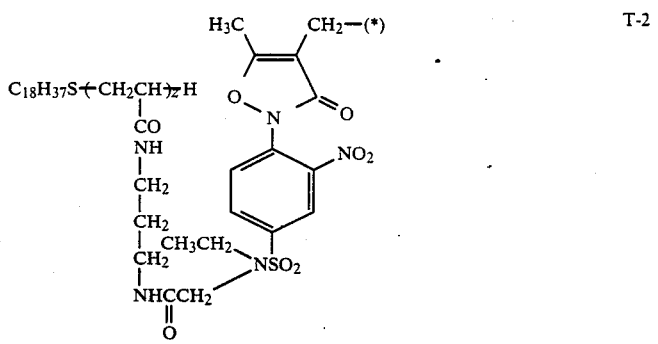
x/y = 8/92 (wt/wt)
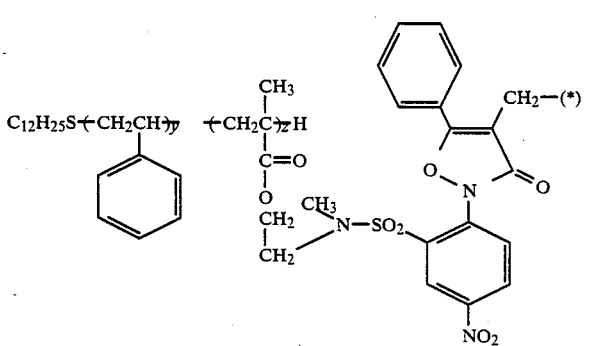
x/y/z = 6/34/60 (wt/wt/wt)
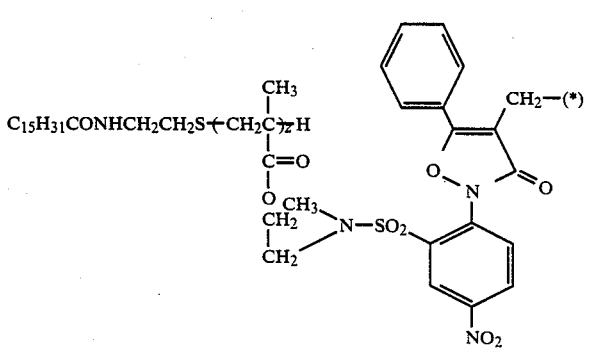
x/z = 10/90 (wt/wt)

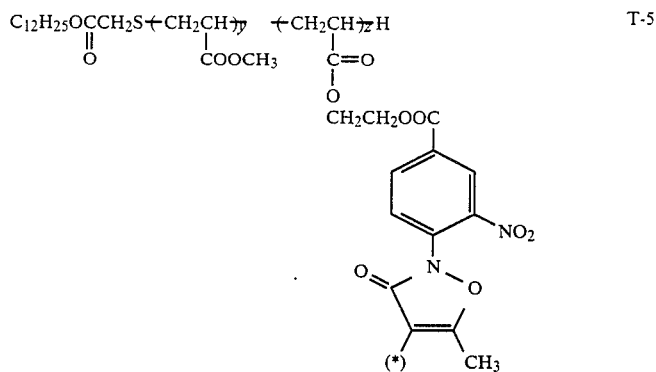
T-5
x/y/z = 4/36/60 (wt/wt/wt)
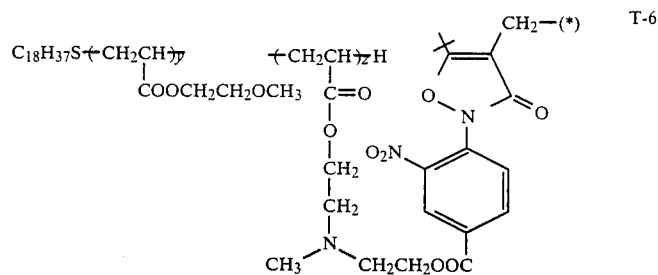
T-6
x/y/z = 6/24/70 (wt/wt/wt)
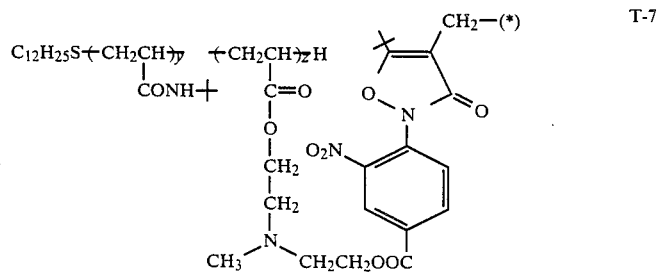
T-7
x/y/z = 5/45/50 (wt/wt/wt)
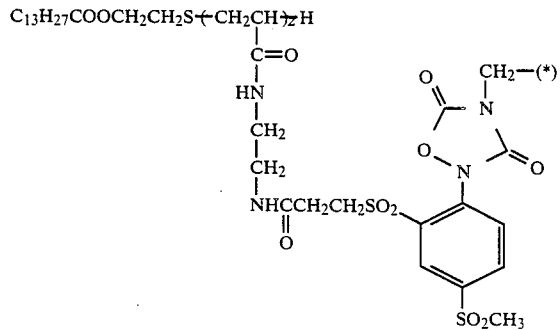
T-8
x/z = 7/93 (wt/wt)

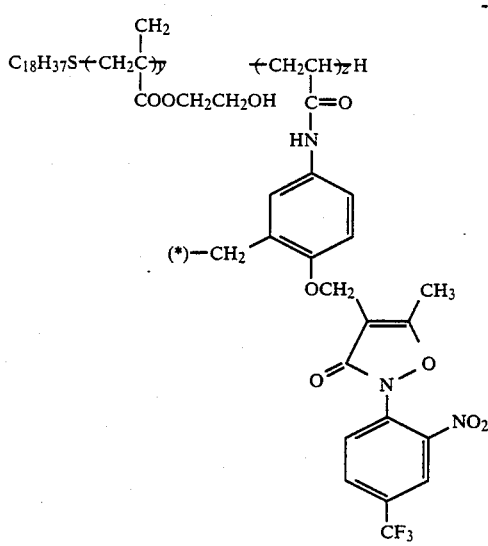

T-9 x/y/z = 5/55/45 (wt/wt/wt)

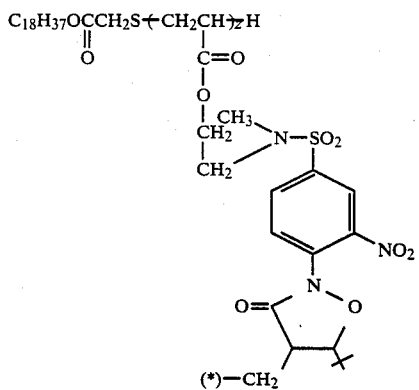

T-10 x/z = 12/88 (wt/wt)

Further, specific examples of a combination of low molecular compounds to be employed for preparation of the high molecular compound represented by formula (VI) in the present invention are described below.

Each figure in parentheses represents a mole fraction of the corresponding low molecular compound.

| | |
|---|---|
| K-1 | Exemplified compound M-4 (25)/Tetraethylene glycol (25)/Hexamethylenediisocyanate (50) |
| K-2 | Exemplified compound M-23 (20)/Diethylene glycol (30)/Ethylenediisocyanate (50) |
| K-3 | Exemplified compound M-28 (40)/1,6-Hexanediol (10)/Hexamethylenediisocyanate (40)/2,4-Diisocyanatotoluene (10) |
| K-4 | Exemplified compound M-4 (20)/1,4-Butanediol (30)/Hexamethylenedicarboxylic acid (50) |
| K-5 | Exemplified compound M-33 (30)/Hexamethylenediamine (20)/1,4-Diisocyanatocyclohexane (50) |
| K-6 | Exemplified compound M-41 (25)/Hexamethylenediamine (25)/Hexamethylenediisocyanate (50) |
| K-7 | Exemplified compound M-42 (30)/1,3-Propanediamine (20)/Adipic acid chloride (50) |
| K-8 | Exemplified compound M-14 (20)/Sebacic acid (30)/Tetraethylene glycol (25)/Ethylene glycol (25) |
| K-9 | Exemplified compound M-11 (15)/Succinic acid (35)/Diethylene glycol (25)/Tetraethylene glycol (25) |
| K-10 | Exemplified compound M-10 (25)/Adipic acid (25)/Hexamethylene glycol (50) |

The high molecular compounds of the present invention may have any average molecular weight. However, it is to be desired that they should have an average molecular weight ranging from about 1,500 to 150,000, particularly from about 5,000 to 100,000.

Methods of synthesizing the compound of the present invention are described below.

Synthesis of the high molecular compound of the present invention requires suitable copolymerizable monomers.

The moiety represented by PWR in the compound of formula (I) can be synthesized by, e.g., the synthesis examples disclosed in the patents cited previously for detailed descriptions of PWR (including U.S. Pat. Nos. 4,139,389, 4,139,379 and 4,564,577, Japanese Patent Application (OPI) Nos. 18533/84 and 84453/82, U.S. Pat. No. 4,232,107, Japanese Patent Application (OPI) No. 101649/84, Research Disclosure, IV, No. 24025 (1984), Japanese Patent Application (OPI) No. 88257/86, West German Patent Application (OLS) No. 3,008,588, Japanese Patent Application (OPI) No. 142530/81, and U.S. Pat. Nos. 4,343,893, 4619,884, 4,450,223 and 4,609,610). Detailed synthesis methods for the moiety corresponding to PWR of the compound represented by formula (II) are given hereinafter.

Connection of PWR to ─(Time)$_t$─PUG can be achieved by reference to the above-cited patents and the methods described hereinafter.

PUG can be synthesized by reference to, e.g., the patents, and publication cited in the detailed description of PUG, whilt Time can be synthesized by reference to Japanese Patent Application (OPI) Nos. 147244/86 and 244873/85, and the patents cited therein.

Now methods for synthesizing the compound represented by formula (II) are described in detail. Since, it is difficult to collectively discuss all general synethsis methods of the compound represented by formula (II), general synthesis methods depending on every X atom (including oxygen, sulfur and nitrogen) attached to N are first described, and then concrete examples of the general methods are given for the purpose of further understanding.

To begin with, a general synthesis method of the compound containing an oxygen atom as X in formula (II) is described.

The most significant point regarding the synthesis method thereof is the way of combining an N—O bond-containing group with an electron-accepting group. This method of bonding can be classified into two processes. One process includes introducing a nitro group into an electron accepting moiety, reducing the nitro group with a zinc-ammonium chloride system to convert it into hydroxylamine, and binding $-(\text{Time})_t\text{PUG}$ to the resulting moiety. The other process includes introducing a group readily undergoing substitution, such as a halogen atom or so on, into an electron accepting moiety, and submitting the resulting moiety to a nucleophilic substitution reaction with hydroxylamine or an equivalent compound. The synthesis according to the former process can be effected using the methods described in S. R. Sandler & W. Karo, *Organic Functional Group Preparations*, and the synthesis according to the latter process can be achieved by running the reaction in a solvent, such as ethanol, dimethylformamide or dimethyl sulfoxide, under neutral or basic conditions.

Secondly, a general synthesis method of the compound represented by formula (II) in which X is a sulfur atom, and the N—S bond does not constitute a hetero ring is described. The method has two routes in the broad sense.

In route A, a sulfenamide is prepared from a sulfenyl chloride and an amine, and then changed to N-acyl- or N-sulfonyl-sulfenamide by using the nucleophilic property of the residual amine.

In route B, on the other hand, an N-acylated or N-sulfonylated compound is first prepared from an amine, and an anion is produced on that nitrogen, followed by nucleophilic substitution of the anion for a sulfenyl chloride.

The sulfenyl chloride is prepared by the reaction of the corresponding disulfide or thiol with chlorine or sulfuryl chloride. The disulfide is chiefly prepared by the replacement reaction of an alkali disulfide with $R_1$—Cl (or $R_1$—$N_2 \oplus X \ominus$), and the thiol is prepared in accordance with general synthesis methods described in Saul Patai, *The Chemistry of the Thiol Group Part I*, Chap. 4, (John Wiley & Sons 1974).

On the otherhand, general sysnthesis methods of the compounds containing the N—S bond as a part of the hetero ring are classified into two groups.

In methods belonging to the first group, a hetero ring containing a N—S bond is first systhesized, and then an electron accepting moiety is bonded to the nitrogen atom. Many methods fo synthesizing hetero rings are known. Many of them are summarized, e.g., in *Comprehensive Heterocyclic Chemistry*. The reaction with an electron accepting moiety can be conducted in a solvent, such as ethanol, dimethylformamide, dimethylsulfoxide or the like, under neutral or basic conditions.

In methods belonging to the second group, ring closure is carried out using the nitrogen atom attached to an electron accepting moiety.

Third, general methods of synthesizing the compound represented by formula (II) in which X is a nitrogen atom are described below. They are classified as Method A or Method B.

(Method A):

An electro accepting group which can undergo the aromatic nucleophilic substitution reaction, such as 4-halo-3-nitrobenzenesulfonamide, is allowed to react with hdrazide or sulfonyl hydrazine in an aprotic solvent, such as dimethyl sulfoxide or dimethylformamide, in the presence of a base, and then halomethylated. Thereafter, a photographically useful group is bound through a replacement reaction. On the other hand, when the photographically useful group to be bonded is reactive to hydrazide or sulfonyl hydrazine, it can be introduced through a reaction with hydrazide or sulfonyl hydrazide.

(Method B):

An electro accepting group which can undergo the aromatic nucleophilic substitution reaction, such as 4-halo-3-nitrobenzenesulfonamides, is allowed to react with a heterocyclic compound which has an N—N single bond, either of the nitrogen atoms being dissociative, in the presence of an aprotic polar solvent, as in Method A to bind the electron accepting group to the nitrogen atom of the heterocyclic ring. By taking advantage of this reaction, the heterocyclic compounds can be selected with regard to the release of photographically useful groups, as shown in some of the specific compound examples.

In the above-described manner, monomers exhibiting activities in the polymerization reaction can be synthesized.

In the case of the polymers represented by formula (IV), monomers previously illustrated as V—1 to V—95 are polymerized using general polymerization processes, for example, a solution polymerization process performed in an organic solvent, or a suspension or emulsion polymerization process carried out using water as a dispersion medium. In particular, the emulsion polymerization process is preferred when x (or the fraction of the monomer unit A) is not zero.

The polymers represented by formula (V) can be synthesized by polymerizing monomers previously illustrated as V—1 to V—95 in the presence of a chain transfer agent represented by E—$X^1$ (wherein E and $X^1$ have the same meanings as described previously) in accordance with a general polymerization method, e.g., a solution polymerization carried out in an organic solvent, a suspension or emulsion polymerization performed with the monomers dispersed in water, or so on. The polymers obtained by the use of such chain tranfer agents are called "telomers", and described in detail in *Olygomer*, compiled by Shin Ohgawara, et al., pp. 10–30, (Kohdansha Scientific, 1976).

Usable chain transfer agents include various compounds, as described in *Olygomer*. Among them, mercaptans (thiols) and halides are particularly preferred over others.

Moreover, the polymers represented by formula (V) may be synthesized through a polymerization reaction using a chain transfer agent containing not less than 8 carbon atoms, which is represented by E—$X^1$ as described above, or by first running a polymerization reaction using a chain transfer agent containing less than 8 carbon atoms (e.g., 2-mercaptoethylamine, 2-mercaptoethanol, etc.) and then a macromolecular reaction (e.g., reaction of a telomer with myristic acid chloride in the presence of 2-mercaptoethylamine).

The preferred molecular weight of the polymer represented by formula (V), though depending on the monomers used, ranges from about 1,500 to 15,000 as a number average.

Polymers represented by formula (VI) can be synthesized by carring out a polycondensation or polyaddition reaction using monomers previously illustrated as M—1 to M—43.

The syntheses of high molecular compounds through polycondensation or polyaddition are described in detail, e.g., in Shin Jikken Kagaku Kohza ("New Lectures on Experimental Chemistry"), Vol. 19 (Kohbunshi Kagaku (I), which means "Polymer Chemistry (I)"), pp. 117–184, ed. by Japanese Chemical Society (1978); Takayuki Ohtsu & Masayoshi Kinoshita, Kohbunshi Gosei no Jikkenho ("Experimental Techniques for Syntheses of High Molecular Compounds"), pp. 287–338, (Kagaku Dohjin, Kyoto, 1972); and so on.

Specific examples and preparation methods of diols, diamines, dicarboxylic acids and diisocyanates from which $L^3$ can be derived are described in detail, e.g., in Kohbunshi Jikkengaku ("Experimental Studies on Polymers"), Vol. 3 (Monomer II), (Kyoritsu Shuppan, Tokyo, 1977); Japanes Patent Application (OPI) No. 145556/86; and so on.

Whe PUG is unstable in a polymerization reaction, the polymerization reactionis carried out prior to introduction of PUG, and the polymer obtained is reacted with PUG or such a low molecular compound as to produce PUG, resulting in synthesis of the intended polymer.

Specific examples of polymer syntheses described above are given below.

SYNTHESIS EXAMPLE 1

Synethesis of Compound 8 employed in Example 4:

(Step 1)

Synthesis of 4-Chloro-3-nitrobenzenesulfonyl Chloride;

To a mixed solution containing 1,280 g of potassium 4-chloro-3-nitrobenzenesulfonate, 1,150 ml of acetonitrile, 250 ml of Sulfolane (tetrahydrothiophene 1,1-dioxide) and 30 ml of dimethylacetamide was dropwise added 1,250 ml of phoshporus oxychloride under an inside temperature at 60° C. to 70° C. After the reaction was continued for 3 hours at 73° C., the reaction mixture was cooled with water, and thereto was slowly added 400 ml of water. The thus obtained product was poured into 5 liters of ice-cold water. The crystalline precipitate was filtered off, washed with water, and dried.

Yield was 1,060 g, and yield rate was 84%.

(Step 2)

Synthesis of 4-Chloro-3-nitro-N-methyl-N-(2-hydroxyethyl)benzenesulfonamide;

A solution containing 500 g of 4-chloro-3-nitrobenzenesulfonyl chloride in 1,000 ml of acetonhitrile was dropwise added to a solution containing 161 g of N-methylethanolamine in 1,500 ml of water as the mixture was cooled with ice-cold water. After the conclusion of dropwise addition, the stirring was continued for 1 hour at 20° C., and then the reaction mixture was made weakly acidic with dilute hydrochloric acid, extracted with ethyl acetate, washed 4 to 5 times with dilute hydrochloric acid, and concentrated. Thus, the intended oily matter was obtained. Yield: 459 g. Yield rate: 86%.

(Step 3)

Synthesis of 5-t-Butyl-3-hydroxyisooxazole;

The above-described compound can be synthesized with ease by reference to the methods described in the following publications and patent specifications.

For instance, Sankyo Kenkyusho Nenpo, vol. 22, p. 215 (1970), Japanese Patent Publication No. 9675/77, Bulletin de la Societe Chimique de France, p. 1978, Japanese Patent Application (OPI) Nos. 206668/82 and 206667/82, Tetrahedron, vol. 20, p. 2835 (1964), Japanese Patent Application (OPI) Nos. 194867/83 and 70878/82, Japanese Patent Publication No. 48953/74, Japanese Patent Application (OPI) No. 190977/84, Journal of Organic Chemistry, vol. 48, p. 4307 (1983), Chemical and Pharmaceutical Bulletin, vol. 14, p. 277, Heterocycles, vol. 12, No. 10, p. 1297, Canadian Journal of Chemistry, vol. 62, p. 1940, and Japanese Patent Application (OPI) No. 501907/84 can be referred to.

Specifically, 5-t-butyl-3-hydroxyisooxazole was synthesized as follows.

583.7 g of hydroxylamine hydrochloride was dissovled in 2 liter of 4N water solution of sodium hydroxide and cooled on an ice bath. Thereto was added 2 liters of ethanol, and further added a 1:1 mixed solution of 4N sodium hydroxide and ethanol in order ot control the pH of the resulting solution to 10.0. Thereto were dropwise added 1,380 g of ethyl pivaloylacetate and a 1:1 mixed solution of 4N sodium hydroxide and ethanol such that the pH of the reaction mixture was adjusted to 10.0±0.2, and the temperature thereof was controlled to 0°–5° C. After the conclusion of the dropwise addition, the stirring was continued for 2 hours at room temperature, and then the reaction product was poured into 6 kg of concentrated hydrochloric acid cooled to 0° C. The solution was allowed to stand for 12 hours. The thus precipitated crystals were filtered off, thoroughly washed with water, and dried. Yield: 770 g. Yield rate: 68%.

(Step 4)

Synthesis of 5-t-Butyl-2-[4-N-methyl-N-(2-hydroxyethyl)sulfamoyl-2-nitrophenyl]-4-isooxazoline-3-one;

400 g of 4-chloro-3-nitro-N-methyl-N-(2-hydroxyethyl)benzenesulfonamide, 288 g of 5-t-butyl-3-hydroxyisooxazole, 290 g of potassium carbonate and 1.5 liter of dimethyl sulfoxide were mixed, and the reaction was continued for 6 hours at 65° C.

The reaction product was poured into dilute hydrochloric acid, and the crystalline precipitate was filtered off, washed with water, and dried. Yield: 542 g. Yield rate: 87%.

(Step 5)

Synethesis of
5-t-Butyl-4-chlormethyl-2-[4-N-methyl-N-(2hydroxyethyl)sulfamoyl-2-nitrophenyl]-4isooxazoline-3-one;

392 g of 5-t-butyl-2-[4-N-methyl-N-(2-hydroxyethyl)-sulfamoyl-2-nitrophenyl]-4-isooxazoline-3-one, 200 g of zinc chloride, 200 g of paraformaldehyde and 1.5 liter of acetic acid were mixed, and heated at 80° C. for 8 hours with stirring as hydrogen chloride gas was bubbled thereinto. To the thus obtained reaction mixture, 500 ml of water was further added, and the mixture was heated under reflux for 1 hour. After cooling, the reaction product was poured into ice-cold water to separate out crystals. The crystals were filtered off, and dried. Yield: 347 g. Yield rate: 79%.

(Step 6)

Synthesis of
5-t-Butyl-4-(1-phenyl-5-tetrazolylthio)-methyl-2-[4-N-methyl-N-(2-hydroxyethyl)sulfamoyl-2-nitrophenyl]-4-isooxazoline-3-one.

300 g of the chloromethyl compound synthesized in step 5, 119 g of 1-phenyl-5-mercaptotetrazole and 111 g of potassium carbonate were dissolved in 1,000 ml of acetone, and stirred for 1 hour at room temperature. The reaction mixture was poured into diluted hydrochloric acid, extracted with ethyl acetate, washed with water, and concentrated. To the residue obtained, hexane was added to crystalized the intended product. Yield: 324 g. Yield rate: 82%.

(Step 7)

118 g of 5-t-butyl-4-(1-phenyl-5-tetrazolylthio)methyl-2-[-N-methyl-N-(2-acryloyloxyethyl)sulfamoyl-2-nitrophenyl]-4-isooxazoline-3-one was dissolved in 400 ml of acetonitrile, and thereto was added 20 ml of pyridine. The mixture was cooled with ice-cold water, and thereto was dropwise added 18.1 g of acryloyl chloride. After 6 hours' stirring at room temperature, the reaction mixture was poured into ice-cold diluted hydrochloric acid to separate out crystals. The crystals were filtered off, and dried. Yield: 113 g. Yield rate: 88%.

(Step 8)

A 16 g portion of the monomer, 5-t-butyl-4-(1-phenyl-5-tetrazolthio)methyl-2-[4-N-methyl-N-(2-acryloyloxyethyl)sulfamoyl-2-nitrophenyl]-4-isooxazoline-3-one, synthesized in step 7, 12 g of butylacrylate and 12 g of methylacrylate were dissolved in 160 ml of dimethylacetamide. The solution was heated at 80° C. with stirring in a stream of nitrogen, and thereto was added 10 ml of a dimethylacetamide solution containing 0.4 of dimethyl azobisisobutyrate to initiate the polymerization. After 2 hours' reaction, 10 ml of dimethylacetamide solution containing 0.4 g of dimethyl azobisisobutyrate was further added, and the reaction was continued for additional 3 hours. Thereafter, the reaction mixture was cooled, and poured into 2 liters of water to precipitate solids. The solids were filtered off, thoroughly washed with water, and heated under reduced pressure to dryness. Thus, 38.1 g of the polymer illustrated below was obtained.

According to determination of nitrogen, this polymer contained the monomer synthesized in step 7 in a fraction of 48.5 wt %.

Structure of Compound 8

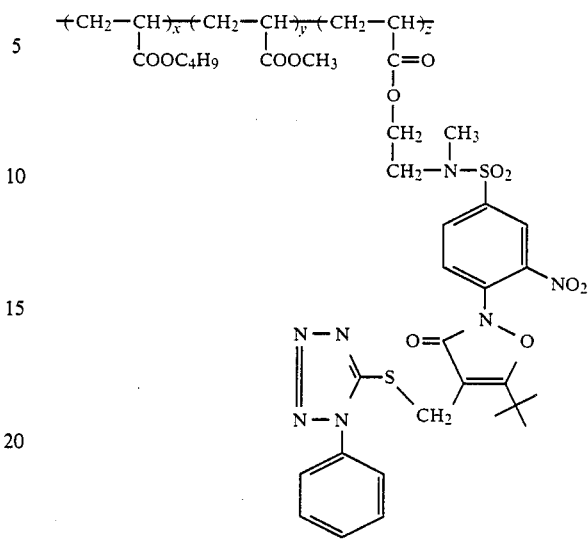

$x/y/z = 30/30/40$
(wt/wt/wt)

The high molecular compound of the present invention may be incorporated into a light-sensitive layer, or another consitituent layer (e.g., a protective layer, an interlayer, a filter layer, an antihalation layer, an image-receiving layer, etc.

An amount of the high molecular compound used in the present invention is not particularly limited, and the preferred range of the amount used depends on the kind of PUG.

For instance, where PUG is a dye (including not only dyes for image-formation, but also filter dyes, antihalation dyes and so on), a preferred coverage of the dye moiety, though depending on its absorptivity, ranges from about $10^{-3}$ to $10^3$ g/m$^2$, particularly from about $10^{-3}$ to 10 g/m$^2$. Where PUG is an ultraviolet absorbent, a preferred coverage thereof is within the same range as that of the above-described dyes. Where PUG is a development inhibitor, a preferred content of the polymer based on the development inhibitor moiety ranges from about $10^{-7}$ to $10^{-1}$ mole, particularly from $10^{-3}$ to $10^{-2}$ mole, per mole of silver halide. Where PUG is a development accelerator or a nucleating agent, a preferred content of the polymer based on the moiety derived from the development accelerator or the nucleating agent ranges from about $10^{-7}$ to $10^{-2}$ mole, particularly from about $10^{-5}$ to $10^{-2}$ mole, per mole of silver halide. Where PUG is a solvent for silver halide, a preferred content of the polymer based on the solvent moiety range from about qb $10^{-5}$ to $10^3$ mole, particularly from about $10^{-4}$ to 10 mole, per mole of silver halide.

When the high molecular compounds of the present invention are soluble in water, they can be dissolved in water or an organic solvent miscible with water, and in that condition can be added to a coating composition containing a hydrophilic colloid. On the other hand, when they can be obtained in the form of latex dispersion, they can be directly added to a hydrophilic colloidal composition for coating. Further, in the case of oil-soluble high molecular compounds, they can be dispersed into a hydrophilic colloidal coating composition using dispersing methods usually employed for dispersion of couplers (e.g., oil dispersion method, Fisher's dispersion method, etc.). Furthermore, according to the solid dispersion method, they can be dispersed without using any solvent.

The high molecular compounds of the present invention are those which can release a photographically useful group upon reduction. Accordingly, if a reducing substance is made to act uniformly on the high molecular compound-containing layer, uniform release of the photographically useful group takes place therein (overall release), while if the reducing substance is converted into an oxidized substance corresponding to the development of silver halide, the photographically useful group can be released countercorresponding to the development of silver halide. Suitable examples are summarized below.

$NaBH_4$, $LiBH_4$, $LiAl(O\text{-}tC_4H_9)_3H$, and $LiAL(OCH_3)_2H$; sulfur or phosphorus compounds having an oxidation potential or 0.80 V or less, such as $Na_2SO_3$, $NaHS$, $NaHSO_3$, $H_3P$, $H_2S$, $Na_2S$ and $Na_2S_2$.

The reducing organic compounds which are usable include, for example organic nitrogen compounds such as alkylamines and arylamines, organic sulfur compounds such as alkylmercaptans and arylmercaptans and organic phosphorus compounds such as alkylphosphines and arylphosphines, and in particular, compounds which follow the Kendal-Pelz theory, are preferred.

Especially preferred reducing agents are given below.

3-Pyrazolidones and precursors thereof, such as 1-phenyl-3-pyrazolidone, 1-phenyl4,4-dimethyl-3-pyrazolidone, 4-hydroxymethyl-4-methyl-1-phenyl -3-

| | Examples of Use | |
|---|---|---|
| Kind of PUG | Overall Release | Release counter-corresponding to AgX Development |
| Image-forming dyes | — | Posi-posi dye image forming system |
| Photographic dyes (YF, AH, etc.) | YFE substitute, Dyeing for separate layers, Improvement in color reproduction, Improvement in sharpness, Control of sensitivity | Improvement in tone of silver image, Improvement in sharpness |
| UV absorbent | Improvement in color reproduction | Control of sensitivity, Control of gradation |
| Brightening agent | Enhancement of whiteness at white background, Acceleration of desilvering | Improvement in S/N due to enhancement of whiteness at nonimage area alone |
| Oxidation inhibitor | Stain restrainer, Discoloration inhibitor | Stain restrainer |
| Dyes for masking | — | Improvement in color reproduction |
| Development inhibitor & Antifoggant | Decrease in Dmin, Cessation of development | Improvement in graininess, Improvement in sharpness, Control of screen range |
| Silver halide solvent | Acceleration of development | Improvement in sharpness |
| Development accelerator | Acceleration of development | Control of gradation, Control of sensitivity |
| Nucleating agent | Acceleration of nucleation, Acceleration of development | Control of gradation |
| Fixation accelerator | Acceleration of fixation | Acceleration of fixation |
| Reducing agent | Prevention of color-mixing, Acceleration of development, Improvement in graininess, Control of gradation | Prevention of color-mixing, Improvement in graininess, Control of gradation |
| Silver image toning agent | Control of tone | Control of tone |
| Film quality improving agent | Acceleration of development, Enhancement of covering power of silver image | Acceleration of development |
| Toe portion cutting-off agent | Increase in contrast | Control of gradation |
| Bleach accelerator | Acceleration of bleaching | Acceleration of bleaching |

The compound of the present invention releases a photographically useful group or a precursor thereof by accepting an electron from a reducing substanc. Consequently, if the reducing substance is converted to the oxidized body in an imagewise distribution, the photographically useful group or the precursor thereof can be released in the reverse imagewise distribution.

The reducing substances used for the reduction of the compounds can be inorganic compounds or organic compounds, and their oxidation potential is preferably lower than the standard oxidation-reduction potential of silver ion-silver, which is 0.80 V.

Examples of usable inorganic compounds include metals having an oxidation potential of 0.80 V or less, such as Mn, Ti, Si, Zn, Cr, Fe, Co, Mo, Sn, Pb, W, $H_2$, Sb, Cu and Hg; ions and complexes thereof having an oxidation potential of 0.80 V or less, such as $Cr^{2+}$, $V^{2+}$, $Cu^+$, $Fe^{2+}$, $MnO_4^{2-}$, $I^-$, $Co(CN)_6^{4-}$, $Fe(CN)_6^{4-}$, $(Fe\text{-}EDTA)^{2-}$; metal hydrides having an oxidation potential of 0.80 V or less, such as NaH, LiH, KH, pyrazolidone, 1m-tolyl-3pyrazolidone, 1-p-tolyl-3-pyrazolidone, 1-phenyl-4-methyl-3-pyrazolidone, 1-phenyl-5-methyl-3pyrazolidone, 1-phenyl-4,4-bis-(hydroxymethyl)-3-pyrazolidone, 1,4-dimethyl-3-pyrazolidone, 4methyl-3-pyrazolidone, 4,4-dimethyl-3-pyrazolidone, 1-(3-chlorophenyl)-4-methyl-3-pyrazolidone, 1-(4chlorophenyl)-4-methyl-3-pyrazolidone, 1-(4-tolyl)-4-methyl-3-pyrazolidone, 1-(2-tolyl)-4methyl-3-pyrazolidone, 1-4-tolyl)-3-pyrazolidone, 1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone, 1,5-diphenyl-3-pyrazolidone, 1-phenyl-4-methyl-4-stearoyloxymethyl-3-pyrazolidone, 1-phenyl-4-methyl-4-lauroyloxymethyl-3-pyrazolidone, 1-phenyl-4,4-bis(lauroyloxmethyl)-3-pyrazolidone, 1-phenyl-2acetyl-3-pyrazolidone and 1-phenyl-3-acetoxypyrazolidone.

Hydroquinones and precursors thereof, such as hydroquinone, toluhydroquinone, 2,6-dimethyl-hydroquinone, t-butylhydroquinone, 2,5-di-t-butylhydroquinone, t-octylhydroquinone, 2,5-di-t-octylhydroquinone, pentadecylhydroquinone, sodium 5-pentadecylhydroquinone- 2-sulfonate, p-benzoyloxyphenol, 2-methyl-4-benzoyloxyphenol and 2-t-butyl-4(4-chlorobenzoyloxy)phenol.

Various reducing agents and combinations thereof as illustrated in U.S. Pat. No. 3,039,869 may also be used in the present invention.

Color developers are usable as a reducing substance in the present invention, including p-phenylene-type color developers as described in U.S. Pat. No. 3,531,286. Among them, N,N-diethyl-3-methyl-p-phenylenediamine is typical. Other useful reducing agents include aminophenols as described in U.S. Pat. No. 3,761,270. Among the aminophenol reducing agents, especially useful compounds are 4-amino-2,6-dichlorophenol, 4-amino-2,6-dibromophenol, 4amino-2-methylphenol sulfate, 4-amino-3-methylphenol sulfate, 4-amino-2,6-dichlorophenol hydrochloride. Further, Research Disclosure, Vol. 151, RD No. 15108 Nov., 1976) and U.S. Pat. No.4,021,240 describe 2,6-dichloro-4-substituted sulfonamidophenols and 2,6-dibromo-4-substituted sulfonamidophenols; and Japanese patent Application (OPI) No. 116740/84 describes p-(N,N-dialkylaminophenyl)sulfamines; and these are usable in the present invention. In addition to the aforesaid phenol-type reducing agents, naphthol-type reducing agents such as 4-aminonaphthol derivatives as described in Japanese Patent Application (OPI) No. 259253/86 and 4-substituted sulfonamidonaphthol derivatives as described in Research Disclosure, Vol. 178, RD No. 17842 (Feb., 1979) and Japanese Patent Application (OPI) No. 88136/81 are especially useful. Further, general color developers are usable in the present invention, which are described in various publications. For instance, U.S. Pat. No. 2,895,825 describes aminohydroxypyrazole derivatives; U.S. Pat. No. 2,892,714 describes aminopyrazoline derivatives; and Research Disclosure, Vol. 194, RD No. 19412 (June, 1980), pp. 227–230 and ibid., Vol. 194, RD No. 19415 (June 1980), pp. 236–240 describe hydrazone derivatives. These color developers may be used singly or in the form of a combination of two or more thereof.

When a nondiffusible reducing substance is incorporated in a light-sensitive material, the combined use of the reducing substance with an electron-transfer agent (abbreviated as ETA, hereinafter) is desirable for acceleration of electron transfer between the reducing substance and developable silver halide emulsions.

ETA can be selected from the above-described reducing substances. In order for ETA to perform its function more effectively, it desired that ETA have a mobility greater than the immobile reducing substances.

As for the reducing substances to be used in combination with ETA, any of the above-described reducing agents can be employed, provided that they do not move in a substantial sense inside the layer of a light-sensitive material. Particularly preferred examples of such reducing substances include hydroquinones, aminophenols, aminonaphthols, 3-pyrazolidinones, saccharin and precursors thereof, picoliniums, the compounds described as electron donors in Japanese Patent Application (OPI) No. 110827/78, and so on.

Specific examples of reducing substances which can be preferably used in combination with ETA are illustrated below.

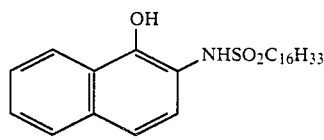

S-1

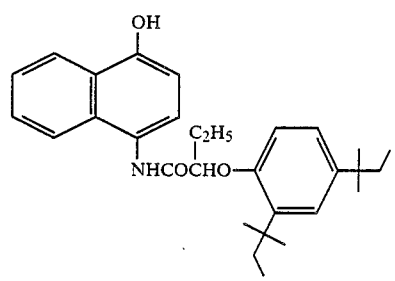

S-2

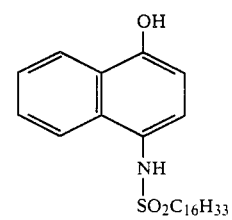

S-3

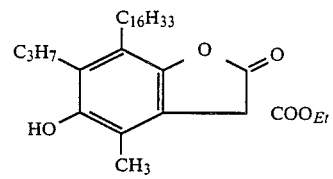

S-4

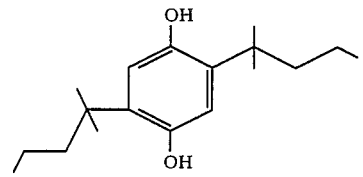

S-5

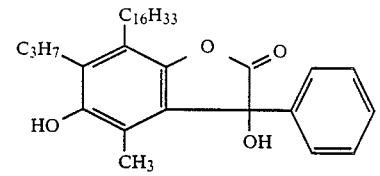

S-6

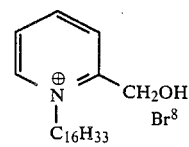

S-7

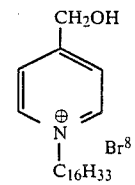

S-8

-continued

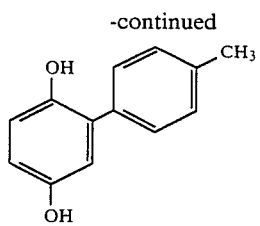

S-23

ETA's usable in combination with the reducing substance may be any ETA which may be cross-oxidized with the substance. Preferred examples thereof are diffusible 3-pyrazolidines, aminophenols, phenylenediamines and reductones.

Specific examples include the following compounds: 3-pyrazolidinones such as 1-phenyl-3-pyrazolidinone, 4,4-dimethyl-1-phenyl-3-pyrazolidinone, 4-hydroxymethyl-4-methyl-1-phenyl-3-pyrazolidinone, 4-hydroxymethyl-4-methyl-1-tolyl-3-pyrazolidinone, 4-hydroxymethyl-4-methyl-1-(4'-methoxy)-3-pyrazolidinone, 4,4bis(hydroxymethyl)-1-phenyl-3-pyrazolidinone, 4,4-bis(hydroxymethyl)-1-tolyl-3-pyrazolidinone, 4,4-bis(hydroxymethyl)-1(4'-methoxy)-3-pyrazolidinone, 4,4-dimethyl-1-toly-3-pyrazolidinone and 1,5-diphenyl-3-pyrazolidinone; aminophenols such as p-aminophenol, p-methylaminophenol, p-dimethylaminophenol, p-dimethylaminophenol, p-dibutylaminophenol, p-piperidinoaminophenol and 4-dimethylamino-2,6-dimethoxy phenol; phenylenediamines such as N-methyl-p-phenylenediamine, N,N-dimethyl-p-phenylenediamine, N,N-diethyl-p-phenylenediamine, N,N,N',N'-tetramethyl-p-phenylenediamine and 4-diethylamino-2,6-dimethoxyamine; and reductones such as piperidinohexose-reductone and pyrrolidinohexose-reductone.

In addition, such precursors that can be hydrolyzed under alkaline conditions to form the aforesaid compounds may be used in the present invention. Such precursors are described, for example, in Japanese Patent Application (OPI) No. 52055/80, Japanese Patent Publication No. 39727/79 and Japanese Patent Application (OPI) No. 135949/82.

The compounds of formula (I) of the present invention may be used in conventional silver halide photographic materials which are to be developed with a developer near normal temperature (for example, X-ray films, lith filsm and other black-and-white photographic materials, color negative films, color papers, color reversal or other color photographic materials, color diffusion transfer photographic materials) or may also be used in other photographic materials for heat development.

In case the present compounds are eapplied to conventional silver halide photographic materials, two systems are preferred for the reaction of the aforesaid reducing substance or the combination of the aforesaid reducing substance and ETA with the photographic material. In one system, the reducing substance or the combination of the substance and ETA is applied to the photographic material in the form of a developer in development thereof; and in the other system, the reducing substance is previously incorporated in the photographic material and the ETA is applied to the material in the form of a developer. In the former system, the preferred amount to be used is 0.001 mole/liter to 1 mole/liter, which is the concentration of the substance(s) in the total developer solution. In the latter system of previous incorporation in the element, 0.01 to 50 moles of the reducing substance is preferably incorporated into the material per mole of the present compound(s), and the concentration of ETA in the solution is preferably 0.001 mole/liter to 1 mole/liter.

On the other hand, in case the present compounds are applied to a heat developable photographic material, the reducing substance or the combination of the reducing substance and ETA is preferably previously incorporated into the heat developable photographic material. In this case, the total amounts are 0.01 to 50 moles, preferably 0.1 to 5 moles, of the reducing substance per mole of the present compound(s), and the total amounts are 0.001 to 5 moles, preferably 0.01 to 1.5 mole of reducing substance per mole of silver halide.

The silver halide which can be used in the present invention may include any of silver chloride, silver bromide, silver iodide, silver chlorobromide, silver chloroiodide, silver iodobromide, and silver chloroiodobromide.

A halogen composition in the silver halide grains may be uniform, or the silver halide grains may have a multiple structure in which the composition is different between a surface portion and an inner portion (see Japanese Patent Application (OPI) Nos. 154232/82, 108533/83, 48755/84 and 52237/84, U.S. Pat. No. 4,433,048 and European Pat. No. 100,984, etc.).

Also, a tabular grain silver halide emulsion containing grains having a thickness of 0.5 μm or less, a diameter of at least 0.6 μm and an average aspect ratio of 5 or more (see U.S. Pat. No. 4,414,310 and 4,435,499, and West German Patent Application (OLS) No. 3,241,646 A1, etc.), and a monodispersed emulsion having a nearly uniform distribution of grain size (see Japanese Patent Application (OPI) Nos. 178235/82, 100846/83 and 14829/83, PCT Application (OPI) No. 83/02338 A1, and European Pat. Nos. 64,412 A3 and 83,377 A1, etc.) may be used in the present invention.

Two or more kinds of silver halides in which a crystal habit, a halogen composition, a grain size and/or a distribution of grain size, etc. are different from each other may be used in mixture. Further, two or more kinds of monodispersed emulsions having different grain size from each other may be employed in mixture to control gradation.

An average grain size of the silver halide used in the present invention is preferably from 0.001 μm to 10 μm, and more preferably from 0.001 μm to 5 μm.

These silver halide emulsion can be prepared by any of an acid process, a neutral process, and an ammonia process. Further, a reaction system of soluble silver salts and soluble halogen salts may be any of a single jet process, a double jet process and a combination thereof. In addition, a reverse mixing process in which silver halide grains are formed in the presence of an excess of silver ions, or a controlled double jet process in which the pAg in the liquid phase is ketp constant, can also be utilized.

Moreover, for the purpose of increasing growth of grains, a concentration of addition, the amount of addition and/or speed of addition of silver slats and halogen salts added may be raised (see Japanese Patent Application (OPI) Nos. 142329/80 and 158124/80, and U.S. Pat. No. 3,650,757, etc.).

Furthermore, silver halide grains of epitaxial junction type (see Japanese Patent Application (OPI) No.

16124/81, and U.S. Pat. No. 4,094,684, etc.) may be employed.

In the step for formation of silver halide grains used in the present invention, ammonia, an organic thioether derivative as described in Japanese Patent Publication No. 11386/72, or a compound containing sulfur as described in Japanese Patent Application (OPI) No. 144319/78, etc., can be used as a solvent for silver halide.

In a process of the formation or physical ripening of silver halide grains, a cadmium salt, a zind salt, a lead salt, or a thallium salt, etc., may coexist. These salts are used for the purposes of improving a change in photographic performance against the pressure, etc. Further, for the purpose of eliminating high-intensity reciprocity failure or low-intensity reciprocity failure, a water-soluble iridium salt such as iridium (III or IV) chloride, ammonium hexachloroiridiate, etc. or a water-soluble rhodium salt such as rhodium chloride, etc., can be used.

Soluble salts may be removed from the silver halide emulsion after precipitate formation or physical ripening, and a noodle washing process or a flocculation process can be used for this purpose.

While the silver halide emulsion may be employed without being subjected to after-ripening, it is usually chemicalloy sensitized. For the chemical sensitization, a sulfur sensitization method, a reduction sensitization method, and a noble metal sensitization method, etc., which are known in the field of emulsions for conventional type photographic light-sensitive materials can be applied alone or in combination therewith. Such a chemical sensitization may be carried out in the presence of a nitrogen-containing heterocyclic compound (see Janpanese Patent Application (OPI) Nos. 126526/83 and 215644/83etc.).

The silver halide emulsion used in the present invention can be that of a surface latent image type in which a latent image is formed mainly on the surface of grains, or that of an internal latent image type in which a latent image is formed mainly in the interior of grains. Further, a direct reversal emulsion in which an internal latent image type emulsion and a nucleating agent are used in combination may be used. Examples of the internal latent image type emulsions suitable for this purpose are described in U.S. Pat. Nos. 2,592,250 and 3,761,276, Japanese Patent Publication No. 3534/83, and Japanese Patent Application (OPI) No. 136641/84, etc. Preferred examples of the nucleating agents suitably used in the present invention are described in U.S. Pat. Nos. 3,227,552, 4,245,037, 4,255,511, 4,266,031 and 4,276,364, and West German Patent Application (OLS) No. 2,635,316, etc.

The silver halide used in the present invention can be spectrally sensitized with methine dyes or other dyes. Suitable dyes which can be employed include cyanine dyes, merocyanine dyes, comples cyanine dyes, complex merocyanine dyes, holopolar cyanine dyes, hemicyanine dyes, styryl dyes, and hemioxonal dyes. Of these dyes, cyanine dyes, merocyanine dyes and complex merocyanine dyes are particularly useful. Any conventionally utilized nucleus for cyanine dyes is applicable to these dyes as a basic heterocyclic nucleus. That is, a pyrroline nucleus, an oxazoline nucleus, a thiazole nucleus, a selenazole nucleus, an aimidazole nucleus, a tetrazole nucleus, a pyridine nucleus, etc., and further,f nuclei formed by condensing an alicyclic hydrocarbon ring with these nuclei and nuclei formed by condensing an aromatic hydrocarbon ring with these nuclei, that is, an indolenine nucleus, a benzindolenine nucleus, a benzoselenazole nucleus, a benzimidazole nucleus, a quinoline nucleus, etc., are appropriate. The carbon atoms of these nuclei may also be substituted.

To merocyanine dyes and complex merocyanine dyes, as nuclei having a ketomethylene structure, 5- or 6-membered heterocyclic nuclei such as a pyrazolin-5-one nucleus, a thiohydantoin nucleus, a 2-thiooxazolidin-2,4-dione nucleus, a thiazolidin-2,4-dione nucleus, a rhodanine nucleus, a thiobarbituric acid nucleus, etc., may also be applicable.

These sensitizing dyes can be employed individually, and can also be employed in combinations thereof. A combination of sensitizing dyes is often used, particularly for the purpose of supersensitization.

The sensitizing dyes may be present in the emulsion together with dyes which themselves do not give rise to spectrally sensitizing effects but which exhibit a supersensitizing effect or materials which do not substantially absorb visible light but which exhibit a supersensitizing effect. For example, aminostilbene compounds substituted with a nitrogen-containing heterocyclic group (for example, those described in U.S. Pat. Nos. 2,993,390 and 3,635,721, etc.), aromatic organic acid-formaldehyde condensates (for example, those described in U.S. Pat. No. 3,743,510, etc.), cadmium salts, azaindene compounds, etc., can be present. The combinations as described in U.S. Pat. Nos. 3,615,613, 3,615,641, 3,617,295 and 3,635,721 are particularly useful.

Gelatin is preferably used as the binder or protective colloid in the emulsion layers or intermediate layers of the present photogrpahic mateials, but other conventional hydrophilic colloids may be used alone or together with gelatin.

The gelatin may be either a lime processed gelatin or acid processed gelatin in the present invention. Details on the preparation of gelatins are given in *The Marcromolecular Chemistry of Gelatin*, written by Arther Vaise, published by Academic Press, 1964.

The photographic emulsions used in the present invention may contain surfactants signly or in the form of a mixture thereof.

These are essentially used as a coating auxiliary and sometimes for some other purposes such as emulsification and dispersion, improvement of photographic characteristic for sensitization, static charge prevention and blocking prevention. These surfactants are classified into natural surfactants such as saponin; nonionic surfactants such as alkyleneoxide type, glycerin type or glycidol type surfactants; cationic surfactants such as higher alkylamines, quaternary ammonium salts, pyridine and the like heterocyclic compounds or phosphonium or sulfonium salts; anionic surfactants containing an acidic group such as a carboxylic acid, sulfonic acid, phosphoric acid, sulfate or phosphate group; and ampholytic surfactants such as amino acids, aminosulfonic acids or aminoalcohol sulfates or phsophates.

The photographic emulsions used in the present invention may contain various compounds for the purpose of the prevention of fog in manufacture, storage or photographic processing of the photographic materials or for the purpose of stabilization of photographic characteristic of the materials. For these purposes, various compounds which are known as anti-fogging agents or stabilizers may be used, including azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole); mercaptopyrimidines; mercaptotriazines; thioketo compounds such as oxazolinthione; azaindenes such as triazaindenes, tetrazaindenes (especially 4-hydroxy-substituted (1,3,3a,7-tetrazaindenes), pentazaindenes; as well as benzenethiosulfonic acid, benzenesulfinic acid and benzenesulfonic acid amide.

The photographic emulsion layers of the present photographic materials may contain, for the purpose of increasing sensitivity, intensification of contrast or acceleration of development, for example, thioether compounds, thiomorpholines, quatrnary ammonium salt compounds, urethane derivatives, urea derivatives, imidazole derivatives or 3-pyrazolidones.

The present photographic materials may further contain, in the photographic emulsion layers or in any other hydrophilic colloid layers, a water insoluble or sparingly soluble synthetic polymer dispersion for the purpose of the improvement of the dimensional stability of the material. Polymers usable for this purpose are homopolymers or copolymers of alkyl (meth)acrylates, alkoxyalkyl (meth)acrylates, glycidyl (meth) acrylates, (meth)acrylamides, vinyl esters (such as vinyl acetate), acrylonitriles, olefins and/or styrenes; as well as copolymers made of a combination of the said monomers and other monomer components such as acrylic acid, methacrylic acid, $\alpha,\beta$-unsaturated dicarboxylic acids, hydroxyalkyl (meth)acrylates, sulfoalkyl (meth)acrylates and styrenesulfonic acids.

The present photographic materials may contain in the photographic emulsion layers, or in any other hydrophilic colloid layers, an inorganic or organic hardener. For example, chromium salts (such as chromium alum, chromium acetate), aldehydes (such as formaldehyde, glyoxale, glutaraldehyde), N-methylol compounds (such as dimethylolurea, methyloldimethylhydantoin), dioxane derivatives (such as 2,3-dihydroxydioxane), active vinyl compounds (such as 1,3,5-triacryloyl-hexahydro-s-triazine, 1,3-vinylsulfonyl-2-propanol), active halogen-containing compounds (such as 2,4dichloro-6-hydroxy-s-triazine), mucohalogenic acids (such as mucochloric acid, muchophenoxychloric acid) and like hardeners. They may be used singly or in the form of a combination thereof.

The silver halide photographic materials of the present invention may contain other various conventional additives well known in the art, for example, whitening agents, dyes, desensitizers, coating assistants, antistatic agents, plasticizers, sliding agents, matting agents, development accelerators, mordanting agents, ultraviolet light absorbents, discoloration inhibitors and color fog-preventing agents.

Examples of such additives which may be used in the present invention are disclosed, for example, in *Research Disclosure*, Vol. 176, RD. No. 17643 Dec., 1978). pp. 22-31.

Various color couplers may be used in the present photographic materials. "Color couplers" herein mean compounds capable of forming dyes by a coupling reaction with an oxidized aromatic primary amine developing agent. Typical examples of usable color couplers are naphthol or phenol type compounds, pyrazolone or pyrazoloazole type compounds and open or heterocyclic ketomethylene compounds. Examples of cyan, magenta and yellow couplers which may be used in the present invention are described in the patent publications referred to in *Research Disclosure*, Vol. 176, RD NO. 17643 (Dec., 1978), Item VII-D and ibid,. Vo. 187, RD No. 18717 (Nov., 1979).

The color couplers to be incorporated in the photographic materials of this invention are preferably non-diffusible and have a ballast group or are polymerized. Two equivalent couplers where the coupling split-off group is substituted are preferred to four equivalent couplers where the coupling active site has a hydrogen atom, because the amount of the silver coated is reduced. Further, couplers capable of forming a dye with a diffusibility, non-coloring coupler, a DIR coupler capable of releasing a development inhibitor on coupling or a coupler capable of releasing a development accelerator on coupling may also be used.

Typical yellow couplers used in the present invention are oil protected acrylacetamide couplers. Examples are described, e.g., in U.S. Pat. Nos. 2,407,210, 2,875,057 and 3,265,506. Two equivalent yellow couplers are preferably used in the present invention, and examples are oxygen atom-releasing type yellow couplers as described in U.S. Pat. Nos. 3,408,194, 3,447,928, 3,933,501, and 4,022,620; and nitrogen atom-releasing type yellow couplers as described in Japanese Patent Publication No. 10739/83, U.S. Pat. Nos. 4,401,752 and 4,326,024, *Research Disclosure*, Vol. 180, RD No. 18053 (Apr., 1979), British Patent No. 1,425,020 and West German Patent Application (OLS) Nos. 2,219,917, 2,261,361, 2,329,587, and 2,433,812. The $\alpha$-pivaloylacetanilide type couplers are excellent in the fastness of the colored dyes, in particular in the light fastness thereof, and the $\alpha$-benzoylacetanilide type couplers generally form dyes of high color density.

The magenta couplers which may be used in the present invention are oil protected type indazolone or cyanoacetyl couplers especially 5-pyrazolone type couplers, such as pyrazolotriazoles. Among the 5-pyrazolone type couplers, those in which the 3-position is substituted by an arylamino group or an acylamino group are preferred in view of the hue or the color density of the colored dyes; typical examples thereof are described in U.S. Pat. Nos. 2,311,082, 2,343,703, 2,600,788, 2,908,573, 3,062,653, 3,152,896, and 3,936,015. As the releasing group in the two equivalent 5-pyrazolone type couplers, preferred are the nitrogen atom-releasing groups as described in U.S. Pat. No. 4,310,619 and the arythio groups as described in U.S. Pat. No. 4,351,897. The 5-pyrazolone type couplers with a ballast group as described in European Patnt. No. 73,636 also can form dyes with a high color density and are useful herein.

Examples of pyrazoloazole type couplers useful herein are pyrazolobenzimidazoles as described in U.S. Pat. No. 3,061,432, preferably pyrazole (5,1-c) (1,2, 4) triazoles as described in U.S. Pat. No. 3,725,067, pyrazolotetrazoles as described in *Research Disclosure*, Vol. 242, RD No. 24220 (Jun. 1984) and Japanese Patent Application (OPI) No. 33552/85 and pyrazolopyrazoiles as described in ibid., Vol. 242, RD No. 24230 (Jun. 1984) and Japanese Patent Application (OPI) No. 43659/85. Imidazo(1,2-b) pyrazoles as described in U.S. Pat. No. 4,500,630 are preferable because of the lower yellow side absorption of the colored dyes and the light fastness thereof, and in particular, pyrazolo(1,5-b) (1,2,4)-triazoles as described in U.S. Pat. No. 4,540,654 are especially preferred.

Cyan couplers which may be used in the present invention are oil protected type napthol and phenol couplers; typical examples thereof are naphthol type couplers as described in U.S. Pat. No. 2,474,293, especially oxygen atom-releasing type two equivalent naphthol couplers as described in U.S. Pat. Nos. 4,052,212, 4,146,396, 4,228,233, and 4,296,200. Examples of phenol type couplers are given in, e.g., U.S. Pat. Nos. 4,369,929, 2,801,171, 2,772,162, and 2,895,826. Cyan couplers which are resistant to moisture and temperature are preferably used in the present invention, and typical examples thereof are phenol type cyan couplers having an ethyl or higher alkyl group in the m-position of the phenol nucleus, as described in U.S. Pat. No. 3,772,002; 2,5-diacylamino substituted phenol type couplers, as described in U.S. Pat. Nos. 2,772,162, 3,758,308, 4,126,396, 4,334,011, and 4,327,173, West German patent application (OLS) No. 3,329,729 and European Patent No. 121,365; and phenol type couplers having a 2-phenylureido group and a 5-acylamino group, as described in U.S. Pat. Nos. 3,446,622, 4,333,999, 4,451,559, and 4,427,767. In addition, naphthol type cyan couplers having a sulfonamido or amido group in the 5-position of the naphthol nucleus thereof, as described in Japanese Patent Applications (OPI) Nos. 237448/85, 153640/86 and 145556/86 and European Patent. No. 161,626, can preferably be used in the present invention, to form color images of high fastness.

In order to correct unnecessary absorption of dyes formed from the magenta and cyan couplers in the short wavelength region, colored couplers are preferably used in color negative photographic materials for photographing. Typical examples of colored couplers are yellow colored magenta couplers as described in U.S. Pat. No. 4,163,670 and Japanese patent Publication No. 39413/82; and magenta colored cyan couplers as described in U.S. Pat. Nos. 4,004,929 and 4,138,258 and British Patent No. 1,146,368.

Couplers forming dyes with an appropriate diffusibility may be used for an improvement of graininess. Regarding smearing couplers, examples of magenta couplers are described in U.S. Pat. No. 4,366,237 and British Patent No. 2,125,570; and yellow, magenta or cyan couplers are described in European Patent No. 96,570 and West German Patent Application (OLS) No. 3,234,533.

The dye forming couplers and the aforesaid special couplers may form dimers or higher polymers. Typical examples of polymerized dye forming couplers in general are described in U.S. Pat. Nos. 3,451,820 and 4,080,211. Examples of polymerized magenta couplers are described in British Patent No. 2,102,173, U.S. Pat. No. 4,367,282, Japanese Patent Application (OPI) No. 232455/86 and U.S. Pat. application Ser. Nos. 849,589 (filed Apr. 8, 1986) and 866,833 (filed May 27, 1986).

Regarding the incorporation of various kinds of couplers into the photographic materials per the present invention, two or more different kinds of couplers may be added to one light-sensitive layer, or the same coupler may of course be added to two or more different layers with no problem.

The compounds of the present invention may be used together with couplers, and may be added to the same emulsion layer together with the couplers, or may be added to an intermediate layers(s) or another photographic auxiliary layer(s) in the form of an independent emulsified dispersion.

The amount of the present compounds to be used is 0.1 to 50 mole%, preferably 0.3 to 15 mole%, based on the coupler in each light-sensitive layer, or the yellow coupler in the blue-sensitive layer, the magenta coupler in the green-sensitive layer or the cyan coupler in the red-sensitive layer, in the color photographic material. The amount is preferably $1\times10^{-5}$ mole to $8\times10^{-2}$ mole, especially $1\times10^{-4}$ mole to $5\times10^{-2}$ mole, per mole of the silver halide in the layer to which the present compound is to be added.

The compounds of the present invention can be used in various kinds of photographic light-sensitive materials such as photographic materials for electron beam, black-and-white photographic materials having high resolving power, black-and-white photographic materials for diffusion transfer process, color photographic materials for X-ray, and color photographic materials for diffusion transfer process.

In the case the silver halide photographic materials of the present invention are processed by a conventional wet method, any and every general means may be used. Known processing solutions may thus be used. The processing temperature is generally selected in the range of 18° C. to 50° C., but this may be lower than 18° C. or higher than 50° C. In accordance with the desire use of the photographic materials, any black-and-white photographic processing for development for the formation of silver images or color photographic processing for development for the formation of color images may be applied to the materials.

Details on various useful photographic processing procedures are described in T. H. James, 4th Ed., *The Theory of the Photographic Process*, pp. 291–436, and *Research Disclosure*, Vol. 176, RD No. 17643 (Dec., 1978), pp. 28–30.

For fixing after black-and-white development, conventional fixers of general compositions may be used. The fixers may contain a thiosulfate or thiocyanate as a fixing agent or an organic sulfur containing compound which is known to be effective as a fixing agent. The fixer may contain a water-soluble aluminum salt as a hardener.

After color development, the photographic emulsion layers are generally bleached. The bleaching may be carried out simultaneously with fixing or separately therefrom.

As the bleaching agent there may be used polyvalent metal compounds such as iron(III), cobat(III), chromium(VI) or copper (II) compounds, peracids, quinones or nitroso compounds. For instance, ferricyanides, bichromates and iron(III) or cobalt(III) organic complexes, for example, with an organic acid such as an aminopolycarboxylic acid (e.g., ethylenediaminetetraacetic acid, nitrilotriacetic acid, 1,3-diamino-2-propanol-tetraacetic acid), citric acid, tartaric acid or malic acid; persulfates and permanganates; and nitrosophenols, etc., may be used. In particular, potassium ferricyanide, sodium ethylenediaminetetraacetato ferrate and ammonium ethylenediaminetetraacetato ferrate are especially useful. Ethylenediaminetetraacetato ferrate complexes are useful either in an independent bleaching solution or in a combined bleach-fix bath.

The bleaching or bleach-fixing solution may contain various additives such as a bleach accelerator as described in U.S. Pat. Nos. 3,042,520 and 3,241,966 and thiol compound as described in Japanese Patent Application (OPI) No. 65732/78.

In particular, compounds of formula (I) of the present invention where a diffusible dye has been introduced as a PUG group are preferably used for heat developable silver halide photographic materials where mobile dyes are formed by heat development and these are transferred to and fixed in a dye fixing layer, as described, e.g., in Japanese Patent Application (OPI) Nos. 149046/83, 154445/84, 165054/84, 180548/84, 218443/84, and 133449/85 and U.S. Pat. Nos. 4,503,137, 4,474,876, 4,483,914, 4,455,363, and 4,500,626.

In the case the present compounds are used in heat developable photographic materials, the compounds do not always require the above-described electron transfer agent (ETA). That is, the use of only the reducing substance (RE) enables to sufficiently take place the reaction. In particular, the use of 4-substituted sulfonamidonaphthols are preferred.

In the case the present compounds are used in heat developable photographic materials, organic metal salts may be used as oxidizing agent, together with the light-sensitive silver halide(s). In this case, the light-sensitive silver halide(s) and the organic metal salt(s) are necessarily kept in direct contact with each other or in close contact with each other.

Among the organic metal salts, organic silver salts are especially preferred.

Organic compounds useful for the formation of the aforesaid organic silver salt oxidizing agents are described, e.g., in Japanese Patent Application (OPI) No. 107243/86 and U.S. Pat. No. 4,500,626 (52nd column and 53rd column). In addition, silver salts of alkynyl group containing carboxylic acids such as silver phenylpropiolate, as described in Japanese Patent Application (OPI) No. 113235/85, are also useful.

The amount of the organic silver salt(s) which may be used is 0.01 to 10 moles, preferably 0.01 to 1 mole, per mole of the light-sensitive silver halide. The total amount of the light-sensitive silver halide and the organic silver salt as coated is suitably 50 mg/m$^2$ to 10 mg/m$^2$, calculated in terms of the coated silver amount.

The image forming substances of heat developable photosensitive materials may be silver, or the compounds of the present invention which contain dyes as PUG's. In case the compounds of the present invention which contain photographically useful groups other than dyes as PUG's are applied to heat developable photosensitive materials, the image forming substances used therein may be silver, or compounds of the kind which can produce or release mobile dyes corresponding or counter-corresponding to reduction of light-sensitive silver halide under a high temperature condition by which silver is produced, that is to say, dye-providing substances.

The present invention can be applied to not only silver image-producing heat-developable photosensitive materials, as described in *Shashin-Kogaku no Kiso* ("Fundamentals of Photographic Engineering"), volume of nonsilver photography, pp. 242–255, (Corona Co., Ltd. 1982); *Eizo Joho* ("Information on Images"), p. 40 (Apr. 1978); Nebletts, *Handbook of Photograpahy and Reprography*, pp. 32–33, (7th Ed., Van Nostrand Reinhold Company); U.S. Pat. Nos. 3,152,904, 3,301,678, 3,392.020 and 3,457,075, British Patent Nos. 1,131,108 and 1,167,777, and *Research Disclosure*, RD-17029, pp. 9–15 (Jun. 1978); but also color image-producing heat-developable photosensitive materials. Heat developable photosensitive materials for obtaining color images include those described in U.S. Pat. Nos. 3,531,286 and 3,761,270, Belgian Patent No. 802,519, *Research Disclosure*, pp. 31–32 (Sep. 1975), U.S. Pat. Nos. 4,021,240, 4,463,079, 4,474,867, 4,478,927, 4,507,380, 4,500,626 and 4,483,914, Japanese Patent Application (OPI) Nos. 149046/83, 149047/83, 152440/84, 154445/84, 165054/84, 180548/84, 168439/84, 174832/84, 174833/84, 174834/84, 174835/84 and so on, U.S. Pat. No. 4,499,180, Japanese Patent Application (OPI) No. 116943/84, European Patent No. 125,421, U.S. Pat. No. 4,499,172, Japanese Patent Application (OPI) Nos. 180537/84, 84640/86, 218443/84 and 238056/86, and European Patent (OPI) No. 210660.

Further, the compounds of the present invention can be applied to silver halide photographic materials for the color diffusion transfer process, which are developed using a processing solution at room temperature or in the vicinity thereof. The color diffusion transfer process is described, e.g., in Belgian Patent No. 757,959.

A photographic element for the color diffusion transfer process is preferably a film unit containing a light-sensitive material (light-sensitive element) and a dye-fixing element (image-receiving element).

A typical representative film unit has a structure of the non-peel-apart type, in which the above-described image-receiving and light-sensitive elements are laminated on a transparent support, and it is unnecessary to peel the light-sensitive element from the image-receiving element after the completion of transfer of images. More specifically, the image-receiving layer comprises at least one mordanting layer, and in a preferred embodiment of the light-sensitive element a combination of a blue-sensitive emulsion layer, a green-sensitive emulsion layer and a red-sensitive emulsion layer, a combination of a green-sensitive emulsion layer, a red-sensitive emulsion layer and an infrared-sensitive emulsion layer, or a combination of a blue-sensitive emulsion layer, a red-sensitive emulsion layer and an infrared-sensitive layer is employed, and a yellow dye-providing substance, a magenta dye-providing substance and a cyan dye-providing substance are incorporated in the element so as to associate themselves with the constituent layers, respectively, in any one of the combinations. (the term "infrared-sensitive emulsion layer" used herein refers to an emulsion layer having sensitivity to light of wavelengths of 700 nm or longer, particular 740 nm or longer.) In addition, a white reflective layer containing a solid pigment like titanium oxide is provided between the mordanting layer and the light-sensitive layer or the dye-providing substance containing layer so that the transferred images can be observed through the transparent support. In order to effect development processing in the light, a light-intercepting layer may be further provided between the white reflective layer and the light-sensitive layer. Furthermore, a peeling-apart layer may be provided at an appropriate location in order to enable a part of all of the light-sensitive element to be peeled from the image-receiving element, if desired. (This format is described, e.g., in Japanese Patent Application (OPI) No. 67840/81 and Canadian Patent No. 674,082).

In another type of film unit of the non-peel-apart type the above-described light-sensitive element is provided on a transparent support, and thereon is provided a white reflective layer, and further thereon is laminated an image-receiving layer.

As for peel-apart film units, in which an image-receiving element, a white reflective layer, a peeling-apart layer and a light-sensitive element are laminated on the same support, and the light-sensitive element is peeled from the image-receiving element in purpose, a detailed description thereof is given in U.S. Pat. No. 3,730,718.

On the other hand, representative types of the film unit of the type which has a light-sensitive element and an image-receiving element on separate supports can be classified into two groups. One group includes film units of the peel-apart type, and the other group include those of the non-peel-apart type. More specifically, in preferred embodiments of the film units of the peel-apart type, an image-receiving element has a light reflecting layer on the back side of a support and at least one image-receiving layer on the surface side thereof, while a light-sensitive element is applied to a separate support having a light-intercepting layer. Therein, the light-sensitive layer is not arranged face to face with the mordanting layer before the conclusion of exposure, but the light-sensitive element is designed so that the light-sensitive layer may be reserved to be brought into a face-to-face contact with the image-receiving layer after the conclusion of exposure (for example, during development-processing). After the transfer of images into the mordanting layer is completed, the light-sensitive element is speedily peeled apart from the image-receiving element.

In preferred embodiments of the film units of the non-peel-apart type, at least one mordanting layer is provided on a transparent support, a light-sensitive element is provided on a separate transparent support or a separate support having a light-intercepting layer, and the light-sensitive element is superposed on the image-receiving element so that the light-sensitive layer may be disposed face to face with the mordanting layer.

Photographic elements for the above-described color diffusion transfer process may be combined with a pressure-rupturable container (processing element) retaining an alkaline processing solution. For instance, in the film unit of the non-peel-apart type which has an image-receiving element and a light-sensitive element on one support in a laminated condition, the processing element is preferably arranged between the light-sensitive element and a cover sheet provided thereon. On the other hand, in the front where the light-sensitive element and the image-receiving element are coated on two separate supports, it is to be desired that the processing element should be arranged between these elements at the time of development-processing at the latest. In the processing element, light-intercepting substances (e.g., carbon black, dyes capable of changing their colors depending on pH, etc.) and/or white pigments (e.g., titanium oxide, etc.) are preferably contained according to the format of the film unit to be combined. Moreover, it is to be desired in the film units of color diffusion transfer process that a neutralization timing mechanism constituted by a neutralizing layer and a neutralization timing layer should be incorporated in a cover sheet, an image-receiving element or a light-sensitive element.

The present invention is now illustrated in greater detail with reference to the following specific examples, but the present invention is not to be construed as being limited thereto. Unless otherwise indicated, all parts, percents and ratios are by weight.

EXAMPLE 1

Preparation of Sample 101:

On a cellulose triacetate film support with a subbing layer were coated layers having the following compositions to prepare a multilayer color light-sensitive material. The thus-obtained material was called Sample 101.

The first layer: Antihaliationg layer

A gelatin layer (dry thickness: 2 microns) containing 0.25 g/m$^2$ of black colloidal silver, 0.04 g/m$^2$ of U-1, 0.1 g/m$^2$ of U-2, 0.1 g/m$^2$, and 0.01 of Oil-2.

The second layer: Interlayer

A gelating layer (dry thickness: 1 micron) containing 5 mg/m$^2$ of Cpd-A 10 mg/m$^2$ of Cpd-B, 50 mg/m$^2$ of Cpd-C, 0.05 g/m$^2$ of I-1, and 0.05 ml/m$_2$ of Oil-1.

The third layer: First red-sensitive emulsion layer

A gelatin layer (dry thickness: 1 micron) containing 0.5 g/m$^2$ (based on silver) of a silver iodobromide emulsion spectrally sensitized with the sensitizing dyes S-1 and S-2 (mean grain size: 0.3, iodide content: 4 mol%), 0.2 g/m$^2$ of C-1, 0.05 g/m$^2$ of C-2, $2\times10^{-3}$ g/m$^2$ of I-2, and 0.12 ml/m$^2$ of Oil-1.

The fourth layer: Second red-sensitive emulsion layer

A gelatin layer (dry thickness: 2.5 microns) containing 0.8 g/m$^2$ (based on silver) of a silver iodobromide emulsion spectrally sensitized with the sensitizing dyes S-1 and S-2 (means grain size: 0.6 micron, iodide content: 3 mol%), 0.55 g/m$^2$ of C-1, 0.14 g/m$^2$ of C-2, $1\times10^{-3}$ g/m$^2$ of I-2, 0.33 ml/m$^2$ of Oil-1, and 0.02 g/m$^2$ of D-1.

The fifth layer: Interlayer

A gelatin layer (dry thickness: 1 micron) containing 0.1 g/m$^2$ Cpd-C, 0.1 ml/m$^2$ of Oil-1, 10 mg/m$^2$ of Cpd-A, 20 mg/m$^2$ of Cpd-B, and 0.02 g/m$^2$ of D-2.

The sixth layer: First green-sensitive emulsion layer

A gelatin layer (dry thickness: 1 micron) containing 0.7 g/m$^2$ (based on silver) of a silver iodobromide emulsion spectrally sensitized with the sensitizing dyes S-3 and S-4 (mean grain size: 0.3 micron, iodide content: 4 mol%), 0.20 g/m$^2$ of C-3, 0.10 g/m$^2$ of C-5, and 0.26 ml/m$^2$ of Oil-1.

The seventh layer: Second green-sensitive emulsion layer

A gelatin layer (dry thickness: 2.5 microns) containing 0.7 g/m$^2$ (based on silver) of a silver iodobromide emulsion spectrally sensitized with the sensitizing dyes S-3 and S-4 (mean grain size: 0.6 micron, iodide content: 2.5 mol%), 0.10 g/m$^2$ of C-4, 0.10 g/m$^2$ of C-5, 0.05 ml/m$^2$ of Oil-2, and 0.05 g/m$^2$ of D-3.

The eight layer: Interlayer

A gelatin layer (dry thickness: 1 micron) containing 10 mg/m$^2$ of Cpd-A, 20 mg/m$^2$ of Cpd-B, 50 mg/m$^2$ of Cpd-C, 0.1 ml/m$^2$ of Oil-2, and 0.01 g/m$^2$ of D-4.

The ninth layer: Yellow filter layer

A gelatin layer (dry thickness: 1 micron) containing 0.1 g/m$^2$ of yellow colloidal silver, 0.02 g/m$^2$ of Cpd-C, and 0.04 ml/m$^2$ of the high-boiling organic solvent Oil-1.

The tenth layer: First blue-sensitive emulsion layer

A gelatin layer (dry thickness: 1.5 microns) containing 0.6 g/m$^2$ (based on silver) of a silver iodobromide emulsion spectrally sensitized with the sensitizing dye S-5 (mean grain size: 0.3 micron, iodide content: 2 mol%), 0.1 g/m$^2$ of C-6, 0.4 g/m$^2$ of C-7, and 0.1 ml/m$^2$ of Oil-1.

The eleventh layer: Second blue-sensitive emulsion layer

A gelatin layer (dry thickness: 3 microns) containing 1.1 g/m$^2$ of a silver iodobromide emulsion spectrally sensitized with the sensitizing dye S-6 (mean grain size: 0.6 micron, iodide content: 2 mol%), 0.4 g/m$^2$ of C-6, 0.8 g/m² of C-8, 0.23 ml/m² of Oil-1, and 0.02 g/m² of D-5.

The twelfth layer: Interlayer

A gelatin layer (dry thickness: 1 micron) containing 5 mg/m² of Cpd-A, 10 mg/m² of Cpd-B, and 0.1 ml/m² of Oil-2.

The thirteenth layer: First protective layer

A gelatin layer (dry thickness: 2 microns) containing 0.02 g/m² of U-1, 0.32 g/m² of U-2, 0.03 g/m² of U-3, and 0.28 ml/m² of Oil-2.

The fourteenth layer: Second protective layer

A gelatin layer (dry thickness: 2.5 microns) containing 0.1 g/m² (based on silver) of a surface-fogged fine grain silver iodobromide emulsion (iodide content: 1 mol%, mean grain size: 0.06 micron), and polymethylmethacrylate particles (mean particle size: 1.5 microns).

In addition to the above-described ingredients, a gelatin hardener and a surface active agent were added to each layer.

The compounds used for preparing the sample are illustrated below.

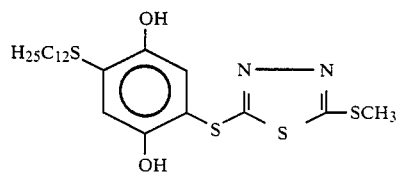
I-1

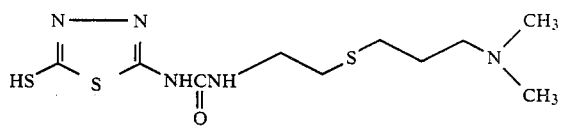
I-2

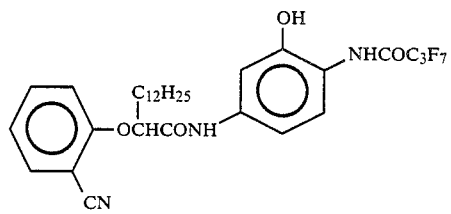
C-1

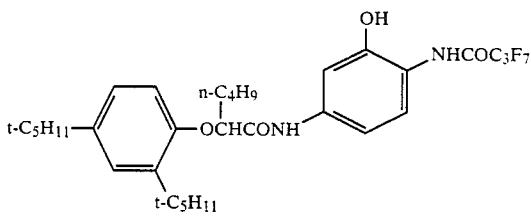
C-2

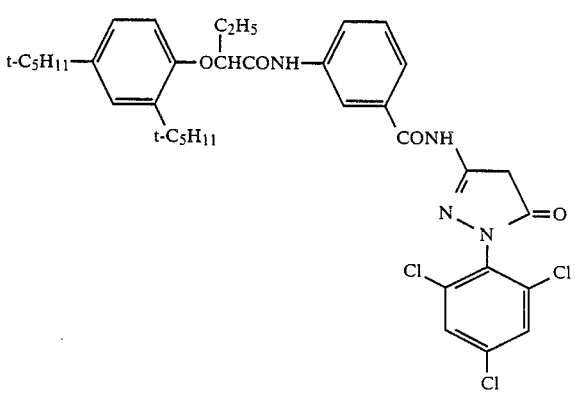
C-3

-continued
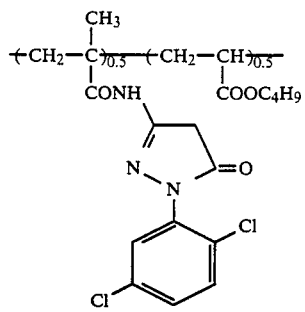
C-4
Average Molecular Weight: about 20,000
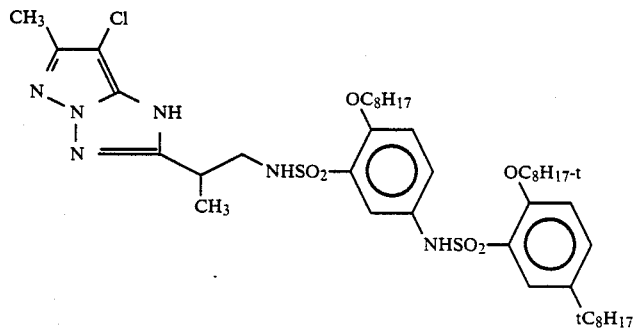
C-5
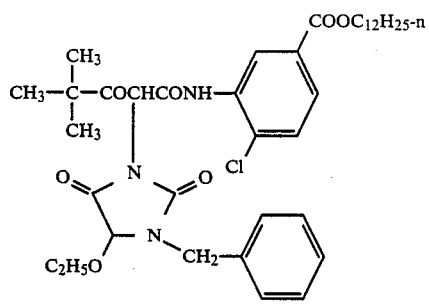
C-6
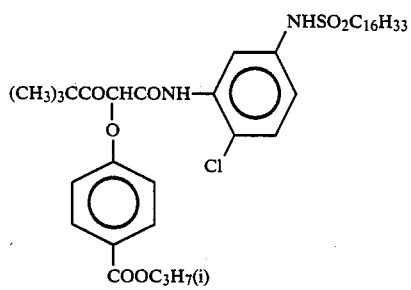
C-7
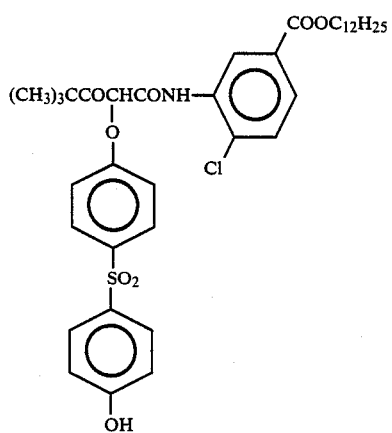
C-8

-continued
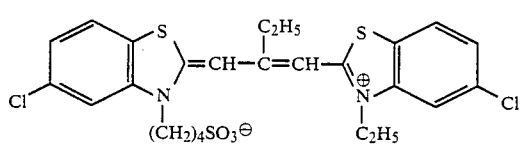
S-1
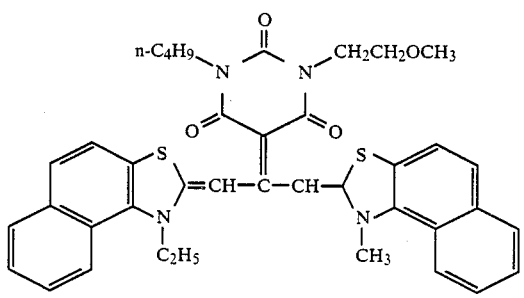
S-2
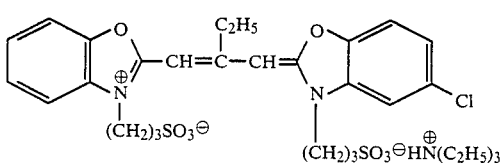
S-3
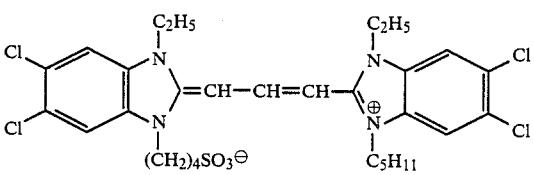
S-4
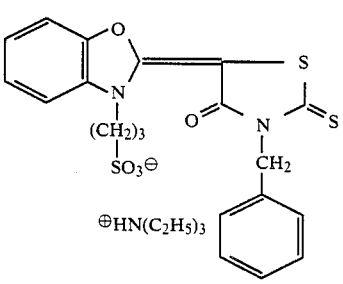
S-5
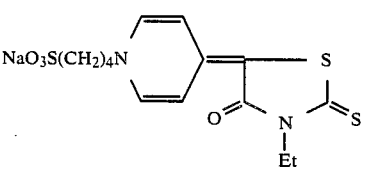
S-6
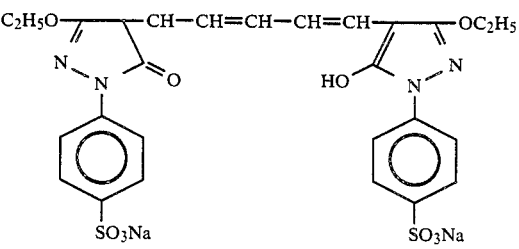
D-1

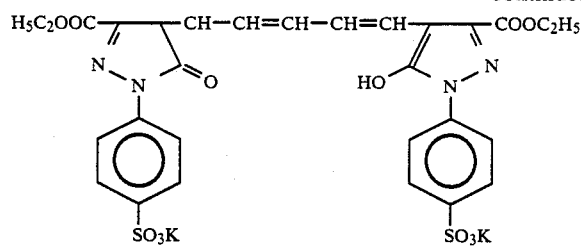
D-2
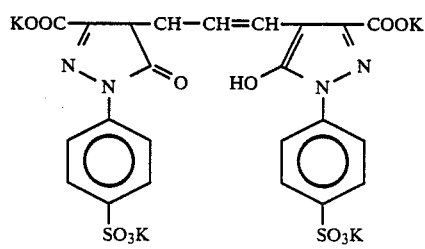
D-3
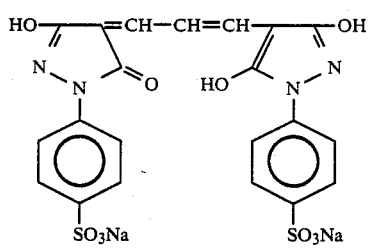
D-4
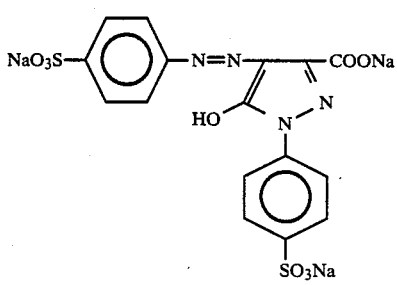
D-5
Tricresyl Phosphate     Oil-1
Dibutyl Phthalate     Oil-2
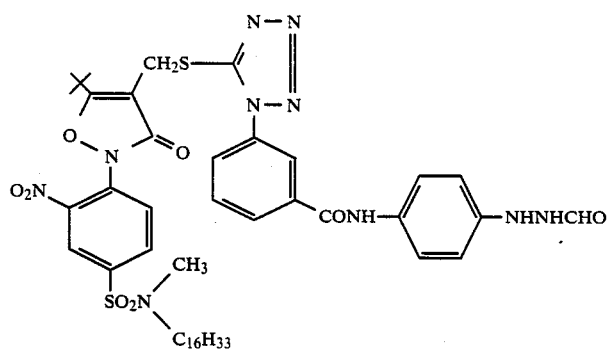
Cpd-A
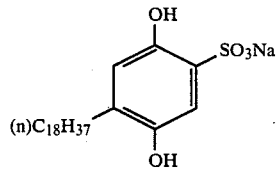
Cpd-B

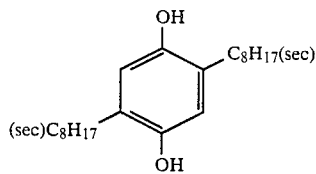
Cpd-C
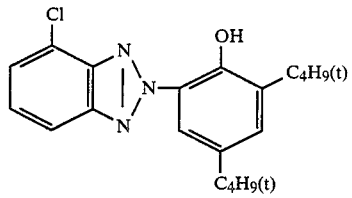
U-1
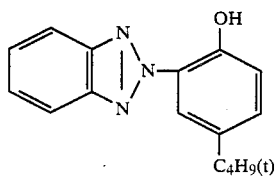
U-2
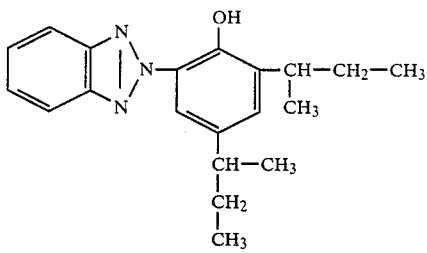
U-3
Preparation of Samples 102 to 104:
Samples 102 to 104 were prepared in the same manner as Sample 101, except that compound Cpd-A in the second layer, the fifth layer, the eighth layer and the twelfth layer was replaced by equimolar amounts of the compounds (1), (2) and (3) of the present invention, respectively.
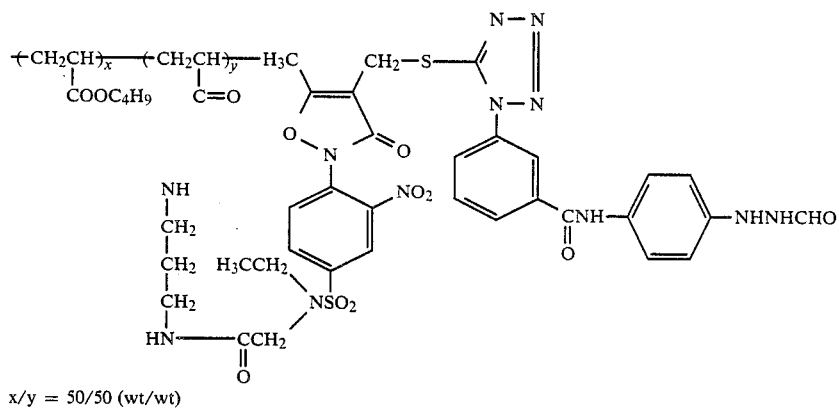
Compound (1)
$x/y = 50/50$ (wt/wt)
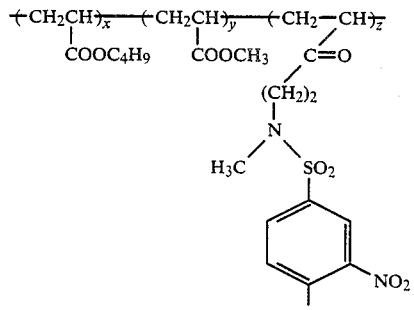
Compound (2)

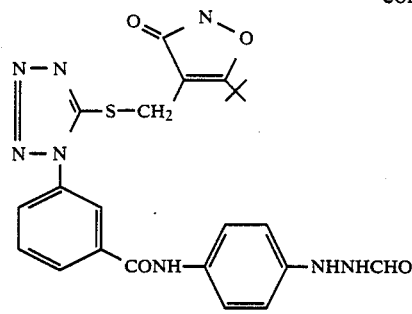

x/y/z = 30/30/40 (wt/wt/wt)

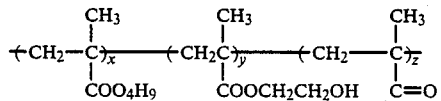

Compound (3)

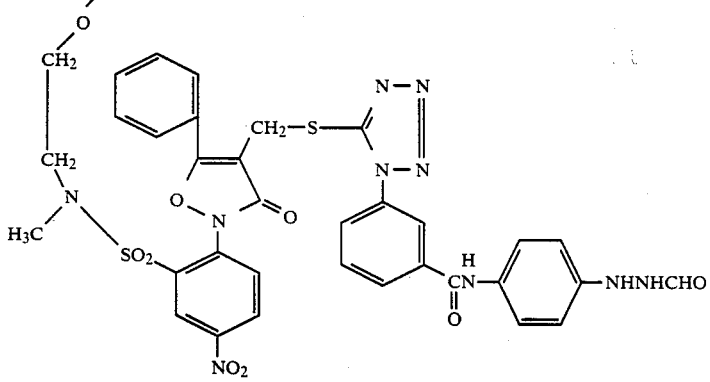

x/y/z = 20/30/50 (wt/wt/wt)

The thus prepared silver halide color photographic materials 101 to 104 were optically exposed, and then processed using an automatic developing machine in accordance with the process described below. The processing was continued until the accumulated amount of the replenisher used for the color developer became three times the capacity of the tank.

| Processing Step | Time | Temperature | Capacity of Tank | Amount replenished |
|---|---|---|---|---|
| First development | 6 min. | 38° C. | 12 l | 2,200 ml/m² |
| First washing | 45 sec. | 38° C. | 2 l | 2,200 ml/m² |
| Color development | 6 min. | 38° C. | 12 l | 2,200 ml/m² |
| Bleach | 2 min. | 38° C. | 4 l | 860 ml/m² |
| Bleach-fix | 4 min. | 38° C. | 8 l | 1,100 ml/m² |
| Second washing (1) | 1 min. | 38° C. | 2 l | — |
| Second washing (2) | 1 min. | 38° C. | 2 l | 1,100 ml/m² |
| Stabilization | 1 min. | 25° C. | 2 l | 1,100 ml/m² |
| Drying | 1 min. | 65° C. | — | — |

The replenishment in the second washing was carried out according to the counter-current process, in which a replenisher was fed to the bath for the second washing (2), and the solution overflowing the bath was introduced into the bath for the second washing (1).

The processing solutions had the following compositions, respectively.

| First Developer | Solution | Replenisher |
|---|---|---|
| Pentasodium nitrilo-N,N,N-tri methylenephosphonate | 2.0 g | 2.0 g |
| Sodium Sulfite | 30 g | 30 g |
| Potassium Hydroquinonemonosulfonate | 20 g | 20 g |
| Potassium Caarbonate | 33 g | 33 g |
| 1-Phenyl-4-methyl-4-hydroxymethyl-3-pyrazolidone | 2.0 g | 2.0 g |
| Potassium Bromide | 2.5 g | 1.4 g |
| Potassium Thiocyanate | 1.2 g | 1.2 g |
| Potassium Iodide | 2.0 mg | — |
| Water to make | 1,000 ml | 1,000 ml |
| pH | 7.0 | 7.0 |

The pH of the first developer was adjusted to the above value using hydrochloric acid and sodium hydroxide.

| First Washing Bath | Solution | Replenisher |
|---|---|---|
| Ethylenediaminetetramethylenephosphonic Acid | 2.0 g | 2.0 g |
| Disodium Phosphate | 5.0 g | 5.0 g |
| Water to make | 1,000 ml | 1,000 ml |
| pH | 7.0 | 7.0 |

The pH of the first washing bath was adjusted to the above value using hydrochloric acid and sodium hydroxide.

| Color Developer | Solution | Replenisher |
|---|---|---|
| Pentasodium nitrilo-N,N,N-tri | 2.0 g | 2.0 g |

| Color Developer | Solution | Replenisher |
|---|---|---|
| methylenephosphonate | | |
| Sodium Sulfite | 7.0 g | 7.0 g |
| Trisodium Phosphate Dodecahydrate | 36 g | 36 g |
| Potassium Bromide | 1.0 g | — |
| Potassium Iodide | 90 mg | — |
| Sodium Hydroxide | 3.0 g | 3.0 g |
| Citrazinic Acid | 1.5 g | 1.5 g |
| N-Ethyl-N-($\beta$-methanesulfonamidoethyl)-3-methyl-4-aminoaniline Sulfate | 11 g | 11 g |
| 3,6-Dithiaoctane-1,8-diol | 1.0 g | 1.0 g |
| Water to make | 1,000 ml | 1,000 ml |
| pH | 11.80 | 12.00 |

The pH was adjusted to the above values using hydrochloric acid and potassium hydroxide.

| Bleaching Bath | Solution | Replenisher |
|---|---|---|
| Disodium Ethylenediaminetetraacetate Dihydrate | 10.0 g | 10.0 g |
| Ammonium Ethylenediaminetetraacetatenato Ferrate (III) Dihydrate | 120 g | 120 g |
| Ammonium Bromide | 100 g | 100 g |
| Ammonium Nitrate | 10 g | 10 g |
| Bleach Accelerator | 0.005 mol | 0.005 mol |

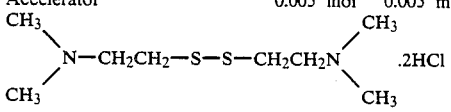

| | | |
|---|---|---|
| Water to make | 1,000 ml | 1,000 ml |
| pH | 6.30 | 6.30 |

The pH was adjusted to the above value using hydrochloric acid or aqueous ammonia.

| Bleach-Fix Bath | Solution | Replenisher |
|---|---|---|
| Ammonium Ethylenediaminetetraacetato Ferrate(III) Dihydrate | 50 g | 50 g |
| Disodium Ethylenediaminetetraacetate Dihydrate | 5.0 g | 5.0 g |
| Sodium Thiosulfate | 80 g | 80 g |
| Sodium Sulfite | 12.0 g | 12.0 g |
| Water to make | 1,000 ml | 1,000 ml |
| pH | 6.60 | 6.60 |

The pH was adjusted to the above value using hydrochloric acid or aqueous ammonia.

Second Washing Bath (Both solution and replenisher)

City water was passed through a column of mixed-bed system which was packed with an H-type strong acid cation-exchange resin (Amberlite IR-120, products of Rohm & Haas Co.) and an OH-type anion-exchange resin (Amberlite IR-400, products of Rohn & Haas Co.) to reduce the calcium ion concentration and magnesium ion concentration to below 3 mg/l, and thereto were added 20 mg/l of sodium dichloroisocyanurate and 1.5 g/l of sodium sulfate. The ph of the resulting solution ranged from 6.5 to 7.5.

| Stabilizing Bath | Solution | Replenisher |
|---|---|---|
| Formaldehyde (37%) | 5.0 ml | 5.0 ml |
| Polyoxyethylene-p-mononylphenyl Ether (mean degree of polymerization: 10) | 0.5 ml | 0.5 ml |
| Water to make | 1,000 ml | 1,000 ml |

The pH of the stabilizing bath was not adjusted. The photographic properties of each sample (including the maximum color density of developed image (Dmax), the minimum color density of developed image (Dmin), and the gradation ($\gamma$)) are shown in Table 1.

TABLE 1

| Sample | Compound | Dmax Y | Dmax M | Dmax C | Dmin Y | Dmin M | Dmin C | $\gamma$ Y | $\gamma$ M | $\gamma$ C |
|---|---|---|---|---|---|---|---|---|---|---|
| 101* | Cpd-A | 3.32 | 3.38 | 3.08 | 0.18 | 0.14 | 0.15 | 2.2 | 2.4 | 2.4 |
| 102** | (1) | 3.47 | 3.51 | 3.16 | 0.19 | 0.14 | 0.16 | 2.2 | 2.4 | 2.4 |
| 103** | (2) | 3.53 | 3.57 | 3.19 | 0.18 | 0.15 | 0.15 | 2.3 | 2.4 | 2.4 |
| 104** | (3) | 3.50 | 3.58 | 3.17 | 0.18 | 0.15 | 0.16 | 2.2 | 2.4 | 2.4 |

*Comparison
**Invention

As shown in the data of Table 1, Sample 101, and Samples 102 to 104 which utilized the compounds of the present invention produced reversal images even when processing with a reversing bath was not performed. In addition, the data in Table 1 indicate that the Dmax values achieved by using the compounds of the present invention were greater than those achieved by using conventional low molecular compound.

This is because the adverse influence produced by a low molecular weight compound on silver halide grains due to diffusion can be reduced by the use of the compounds of the present invention.

EXAMPLE 2

Preparation of Emulsion A:

A water solution of silver nitrate and a water solution of sodium chloride in which ammonium hexachlororhodate(III) was contained in an amount of $2.5 \times 10^{-5}$ mol per mol of silver were mixed in a gelatin solution at 35° C. in accordance with a double jet method as the pH of the mixed system was controlled to 2.3. Thus, a monodisperse silver chloride emulsion having a mean grain size of 0.1 micron was made.

After the grain formation, the soluble salts were removed from the emulsion by the flocculation method wellknown in the art, and 4-hydroxy-6-methyl-1,3,3a,7-tetraazaindene and 1-phenyl-5-mercaptotetrazole were added as stabilizer to the resulting emulsion. Gelatin and silver contained in a 1 Kg portion of the emulsion were 55 g and 105 g, respectively. The thus prepared emulsion was called Emulsion A.

Production of light-sensitive material:

Sample 201

The Emulsion A, 20 mg/g Ag of the nucleating agent illustrated by the following formula, 2 mg/g Ag of the organic desensitizer illustrated by the following formula were added,

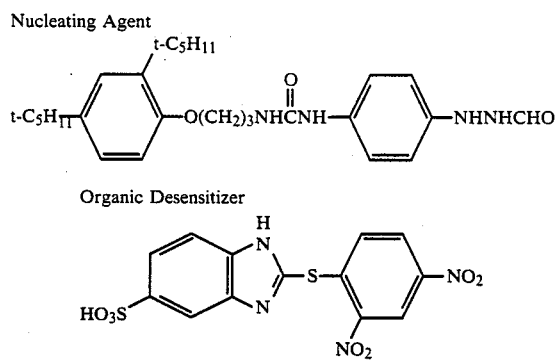

Nucleating Agent

Organic Desensitizer and sodium salt of 2,4-dichloro-6-hydroxy-1,3,5-triazine was further added as hardener. The resulting emulsion was coated on a transparent support of polyethylene terephthalate at a coverage of 3.5 g/m² based on silver. On the emulsion coat, a protective layer containing gelatin (1.3 g/m²) and the compound for comparison UV-1 (0.1 g/m²) was further provided, and dried (to prepare Sample 201).

The compound UV-1 was coated in the form of a gelatin dispersion. The dispersion was prepared in the following manner: A solution containing 14.9 g of the compound UV-1 dissolved in 39 ml of methyl ethyl ketone was mixed with 260 g of a 5.0 wt % water solution of gelatin at 45° C. with stirring to prepare a faintly milky dispersion.

Sample 202

Another sample was prepared in the same manner as Sample 201, except the compound UV-1 was not used. This sample was called Sample 202.

Sample 203

Still another sample was prepared in the same manner as Sample 201, except 0.05 g/m² of water-soluble ultraviolet absorbent UV-2 illustrated below was used in place of 0.1 g/m² of the compound UV-1. This sample was called Sample 203.

Samples 204 to 206

Other samples were prepared in the same manner as Sample 201, except the compound UV-1 was replaced by equimolar amounts of the compounds 4, 5 and 6 of the present invention, respectively. These samples were called Sample 204, 205 and 206, respectively.

In preparing a composition for a protective layer, each of the compounds 4, 5 and 6 was dissolved in ethyl acetate, and then dispersed into gelatin.

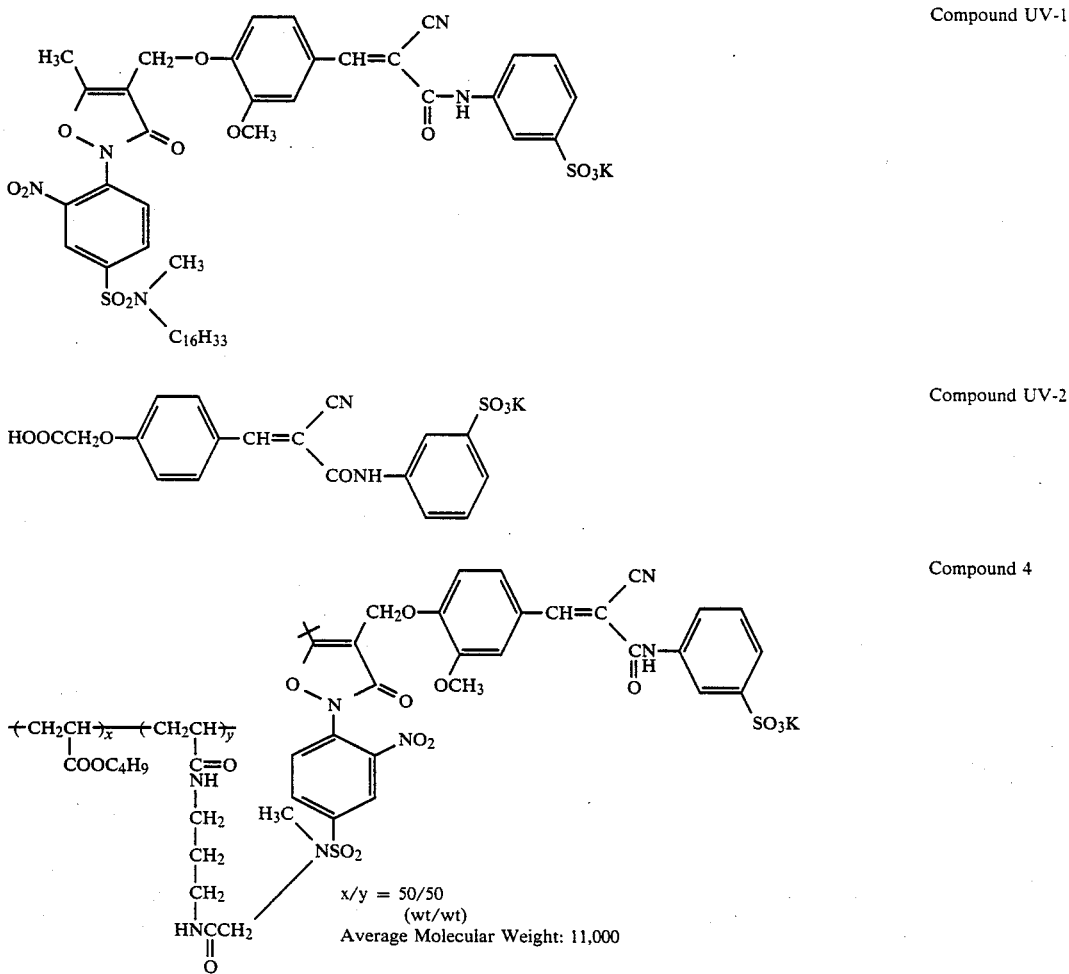

-continued

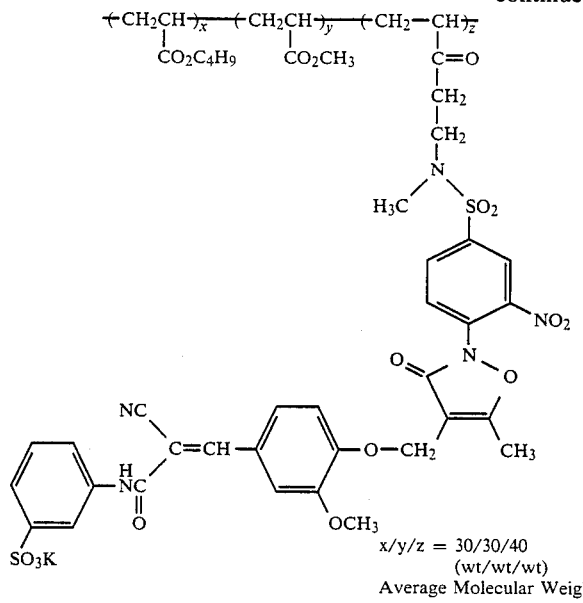

Compound 5 x/y/z = 30/30/40
(wt/wt/wt)
Average Molecular Weight: 16,000

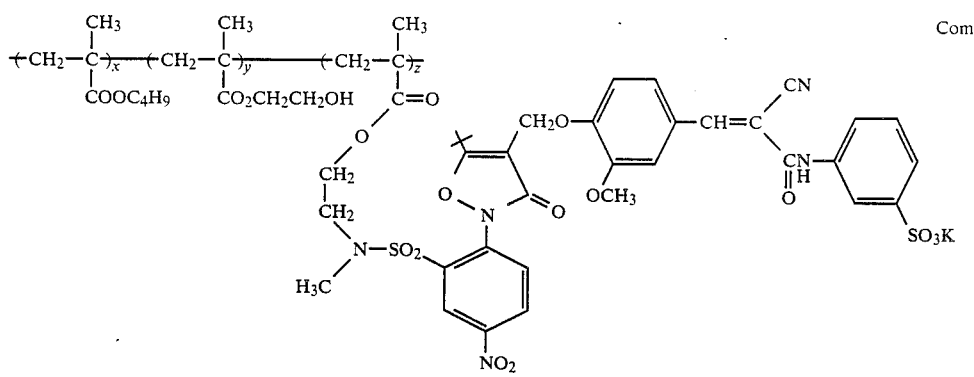

Compound 6 x/y/z = 20/30/50
(wt/wt/wt)
Average Molecular Weight: 14,000

Evaluation of Properties (1) The foregoing 6 samples each was exposed through an optical wedge by means of a daylight printer P-607, produced by Dainippon Screen Mfg. Co., Ltd., developed at 38° C. for 20 seconds using the developer described below, fixed by a conventional manner, washed with water, and dried. UV optical densities in the highlight portions of Samples 201, 203, 204, 205 and 206 were as low as that of Sample 202, which meant the completion of decolorization.

| Basic formula of developer: | |
|---|---|
| Hydroquinone | 35.0 g |
| N-methyl-p-aminophenol one-half sulfate | 0.8 g |
| Sodium hydroxide | 13.0 g |
| Potassium tertiary phosphate | 74.0 g |
| Potassium sulfite | 90.0 g |
| Tetrasodium ethylenediaminetetraacetate | 1.0 g |
| Potassium bromide | 4.0 g |
| 5-Methylbenzotriazole | 0.6 g |
| 3-Diethylamino-1,2-propanediol | 15.0 g |
| Water to make | 1 liter |
| | (pH = 11.5) |

The sensitivities of Samples 203 and 201 were lower than that of Sample 202 by 0.4 and 0.5, respectively, expressed in terms of log E, and those of Samples 204 to 206 were lowered by 0.5. These sensitivity values of Samples 201, 203, 204, 205 and 206 were within the correct region.

(2) Test of safelight safety:

A time for which each sample was safe under illuminance of 400 lux using a UV-cut fluorescent lamp (FLR-40SW-DLX-NU/M, produced by Toshiba Co., Ltd.) as safelight was examined. While the time was 10 minutes with respect to the comparative sample 202, it was 20 minutes with respect to Sample 203, 25 minutes with respect to Sample 201, and about 25 minutes, with respect to Samples 204 to 206 which utilized the present compounds 4 to 6, respectively.

As can be seen from the results of the tests (1) and (2), the compound UV-1 and its polymeric compounds 4, 5 and 6 proved to effectively lower the sensitivity to the corrrect region, and, what is more, to enhance the safelight safety.

(3) Test of tone variability:

Each of the above-described six samples was exposed with the foregoing printer through a plain halftone screen, and subjected to the same development processing as in test (1).

After determination of an exposure time required for the transfer of halftone dot area in a ratio of 1:1 onto each sample through the contact work, each sample was exposed for two or four times the exposure time determined, and examined for the degree of increase in halftone dot area transferred. The degree of increase means that the tone variability of the sample becomes better the greater it is. The results are shown in Table 2. As can be seen from the data shown in Table 2, tone variability was markedly low in Sample 203, while it was high in Samples 201, 204, 205 and 206. This is because the dye used in Sample 203 was homogeneously diffused throughout the sample, from the layer to which it had been added to the light-sensitive layers, due to its solubility and diffusibility in water, so enlargement of halftone dot area from the increase in exposure time was reduced by the irradiation inhibiting effect of the dye.

On the other hand, the compound UV-1 and the high molecular compounds 4, 5 and 6 concerned in the present invention were fixed to the layers to which they had been added, so they contributed to the achievement of high tone variability.

TABLE 2

| | Tone Variability (expressed in terms of the increment of halftone dot area) | |
|---|---|---|
| | Two-fold Exposure | Four-fold Exposure |
| Comparative | | |
| Sample 202 | +5% | +9% |
| Sample 203 | +2% | +4% |
| Sample 201 | +5% | +10% |
| Present | | |
| Sample 204 | +6% | +10% |
| Sample 205 | +5% | +10% |
| Sample 206 | +5% | +9% |

(4) Evaluation of stain caused by reducer:

Strips of the present samples 204 to 206 which had been processed in the same manner as in test (3) were dipped in Farmer's reducer described below at 20° C. for 60 sec., washed with water, and dried. Thereupon, a 50% dot was reduced to 33% dot, and generation of stain was not observed.

| Farmer's Reducer | | |
|---|---|---|
| First solution | Water | 200 ml |
| | Sodium thiosulfate | 20 g |
| Second solution | Water | 100 ml |
| | Hexacyanoferrate(III) | 10 g |

The first solution, the second solution and water were mixed in a ratio of 100:5:100 parts (by volume) at the time of use.

As described above, the compounds 4, 5 and 6 concerned in the present invention had equal or higher ability, compared with the corresponding low molecular compound UV-1 which could release the UV absorbent by reduction. These compounds, which were different from a simple water-soluble UV absorbent, were fixed to the layers to which they had been added, so they did not create any trouble due to migration.

In addition, while the corresponding low molecular compound UV-1 dissolved at 40° C. separated out little by little asfter the lapse of three days, the present compounds 4, 5 and 6 had the advantage in that they did not cause such a trouble.

EXAMPLE 3

On a transparent polyethylene terephthalate support were coated the layers described below in this order to prepare a light-sensitive element.

(I) Dye image receiving layer containing 4.0 g/m$^2$ of copoly[styrene-N-vinylbenzyl-N,N,N-trihexylammonium], and 4.0 g/m$^2$ of gelatin.

(II) White reflective layer containing 22 g/m$^2$ of titanium dioxide, and 2.2 g/m$^2$ of gelatin.

(III) Opaque layer containing 2.7 g/m$^2$ of carbon black, and 2.7 g/m$^2$ of gelatin.

(IV) Cyan dye providing layer constituted with a gelatin dispersion containing 0.33 millimole/m$^2$ of the cyan dye providing compound A and 0.4 millimole/m$^2$ of the compound S-11, and 1.1 g/m$^2$ of gelatin (including gelatin contained in the foregoing dispersion).

Cyan dye providing compound A

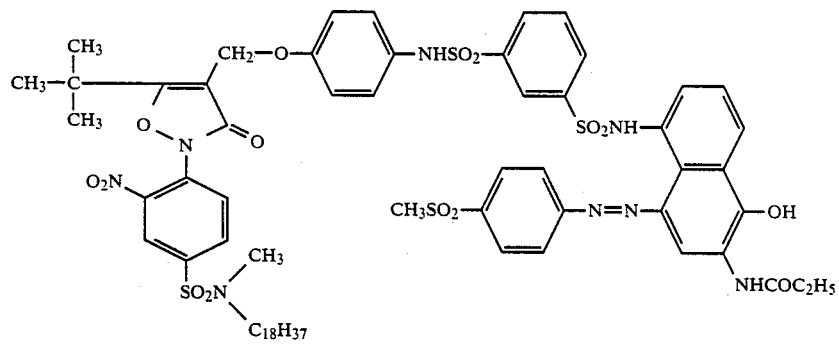

(V) Red-sensitiive layer containing a red-sensitive silver iodobromide emulsion (containing 0.5 g/m$^2$ of silver), and 1.1 g/m$^2$ of gelatin (including gelatin contained in the foregoing emulsion).

(VI) Interlayer containing 0.82 g/m$^2$ of 2,5-di(t-pentadecyl)hydroquinone, 0.8 g/m$^2$ of vinyl acetate, and 0.4 g/m$^2$ of gelatin.

(VIII) Magenta dye providing layer constituted with a gelatin dispersion containing 0.3 millimole/m$^2$ of the magenta dye providing compound B and 0.4 millimole/m$^2$ of the compound S-11, and 2.0 g/m$^2$ of gelatin (including gelatin contained in the foregoing dispersion).

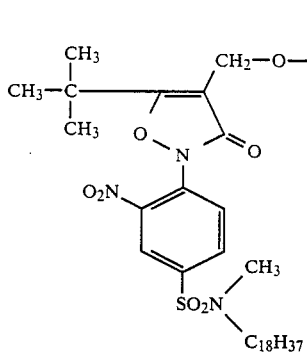
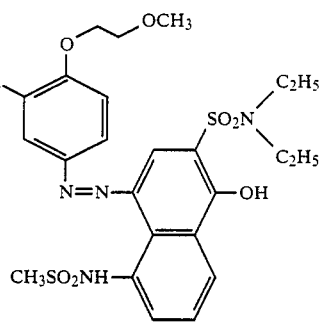

Compound B (VIII) Green-sensitive layer constituted with a green-sensitive silver iodobromide emulsion (containing 0.54 g/m² of silver), and 1.1 g/m² of gelatin (including gelatin contained in the foregoing emulsion).

(IX) The same interlayer as (VI).

(X) Yellow dye providing layer constituted with a gelatin dispersion containing 0.5 millimole/m² of the yellow dye providing compound C and 0.6 millimole/m² of the compound S-11, and 1.1 g/m² of gelatin (including gelatin contained in the foregoing dispersion).

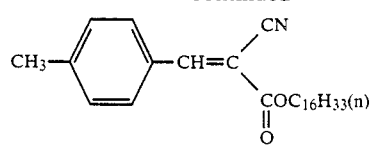

-continued

A cover sheet was prepared by coating on a transparent polyethylene terephthalate film support the following layers in this order.

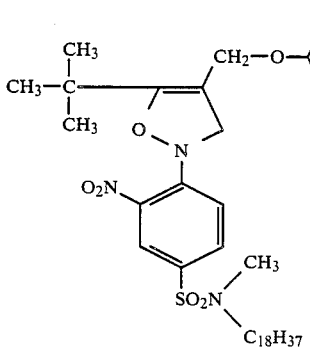

Compound C (XI) Blud-sensitive layer containing 0.5 g/m² of a blue-sensitive silver iodobromide emulsion, and 1.1 g/m² of gelatin (including gelatin contained in the foregoing emulsion).

(XII) Protective layer containing 0.9 g/m² of polymethylmethacrylate latex (mean particle size: 4 microns), 0.4 millimole/m² of the following ultraviolet absorbent A, 0.4 millimole/m² of the following ultraviolet absorbent B, 0.15 g/m² of bisvinylsulfonylmethyl ether as a hardener, and 1.3 g/m² of gelatin.

Ultraviolet absorbent A

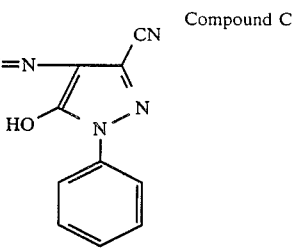

Ultraviolet absorbent B (i) Acid neutralizing layer constituted with 17 g/m² of polyacrylic acid, 0.06 g/m² of N-hydroxysuccinimidobenzenesulfonate, and 0.5 g/m² of ethylene glycol.

(ii) Timing layer prepared by coating cellulose acetate (acetylation degree: 54%) in a layer 2 microns thick.

(iii) Timing layer prepared by coating copoly[vinylidene chloride-acrylic acid] latex in a layer 4 microns thick.

Further, a processing solution with the following composition was prepared.

| | |
|---|---|
| Potassium hydroxide | 48 g |
| 4-Hydroxymethyl-4-methyl-1-p-tolyl-3-pyrazolidinone | 10 g |
| 5-Methylbenzotriazole | 2.5 g |
| Sodium sulfite | 1.5 g |
| Potassium bromide | 1 g |
| Benzyl alcohol | 1.5 ml |
| Corboxymethyl cellulose | 6.1 g |
| Carbon black | 150 g |
| Water to make | 1 liter |

The thus prepared light-sensitive element was called Sample 301, and Samples 302 to 304 were further prepared in the same manner as Sample 301, except changes were carried out in the respects described in Table 3.

Each of Samples 301 to 304 which had been allowed to stand for 3 days under conditions of 45° C. and 80% RH, and each of Samples 301 to 304 which had been made it not only unnecessary to provide an insulating layer but also to reduce the gelatin content in the layer (VII). Owing to these advantages, increased transfer speeds were achieved. Thus, the light-sensitive elements concerned in the present invention were excellent for instant photography.

TABLE 3

| Light-sensitive Element | Details | | | Storage | | | | Transfer Speed | Note |
|---|---|---|---|---|---|---|---|---|---|
| | Magenta dye providing Compound | Gelatin Content in Layer (VII) | Insulating Layer | Storage at Room Temp. | | Storage at 45° C., 80% for 3 days | | | |
| | | | | $D_{max}^G$ | $D_{min}^G$ | $D_{max}^G$ | $D_{min}^G$ | | |
| 301 | A | 2.0 g/m² | absent | 2.05 | 0.27 | 2.10 | 0.41 | 120 sec. | Comparison |
| 302 | A | 2.0 g/m² | Gelatin Layer (0.5 g/m²) provided between Layer (VI) and Layer (VII) | 2.00 | 0.26 | 2.03 | 0.33 | 130 sec. | Comparison |
| 303 | Compound-7 (equimolar amount to A) | 2.0 g/m² | absent | 2.08 | 0.26 | 2.10 | 0.29 | 119 sec. | Invention |
| 304 | Compound-7 (equimolar amount to A) | 0.7 g/m² | absent | 1.97 | 0.26 | 2.05 | 0.29 | 103 sec. | Invention |

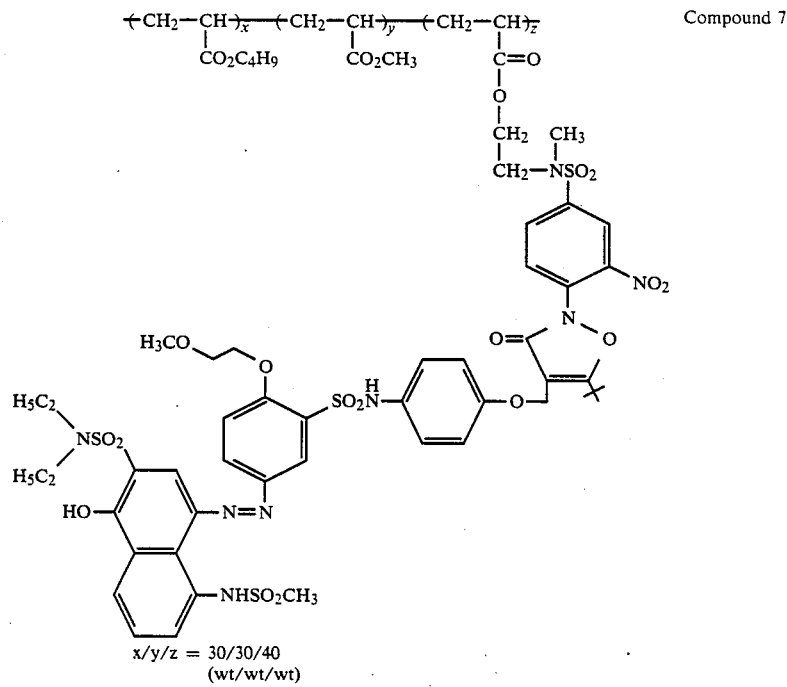

Compound 7 x/y/z = 30/30/40 (wt/wt/wt)

allowed to stand at room temperature were optically exposed through a wedge, and thereon were superposed the foregoing cover sheets, respectively. Therebetween, the processing solution described above was uniformly spread in a layer 80 microns thick with a pair of juxtaposed rollers.

After the lapse of 1 hour from the spread of processing solution, each sample was subjected to sensitometry. The results obtained are shown in Table 3.

In order to determine the change in density of developed image, the time required for the density to be reduced to one-half the density attained at the lapse of 1 hour from the beginning of processing was examined.

As can be seen from the data shown in Table 3, the light-sensitive elements ultilizing the high molecular dye-providing compounds of the present invention

EXAMPLE 4

Integrated type color diffusion transfer light-sensitive sheets and cover sheets were prepared in the following manners Preparation of light-sensitive sheet On a transparent polyethylene terephthalate support were coated the layers described below in this order to prepare each of light-sensitive elements 1 to 9.

(1) Image receiving layer containing 3.0 g/m² of copoly[styrene-N-vinylbenzyl-N-methyl-piperidinium chloride], and 3.0 g/m² of gelatin.

(2) White reflective layer containing 20 g/m² of titanium dioxide, and 2.0 g/m² of gelatin.

(3) Light intercepting layer containing 2.0 g/m² of carbon black, and 1.5 g/m² of gelatin.

(4) Layer containing 0.44 g/m² of the cyan dye releasing redox compound illustrated below, 0.09 g/m² of tricyclohexyl phosphate, 0.008 g/m² of 2,5-di-t-pentadecylhydroquinone, and 0.8 g/m² of gelatin.

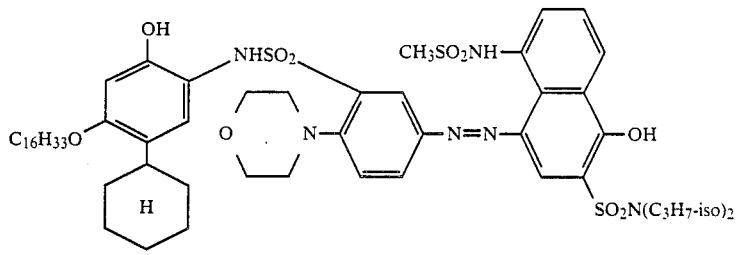

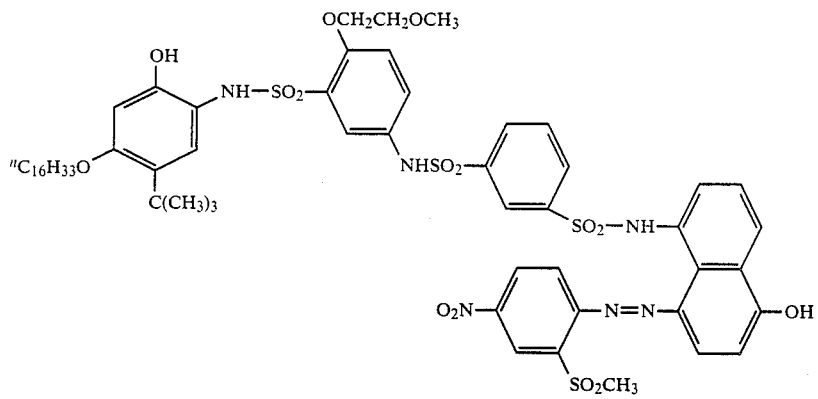

(5) Red-sensitive emulsion layer containing a red-sensitive internal latent image type direct-positive silver bromide emulsion (containing 1.03 g/m² of silver), 1.2 g/m² of gelatin, 0.04 mg/m² of the nucleating agent illustrated below, and 0.13 g/m² of sodium 2-sulfo-5-n-pentadecylhydroquinone.

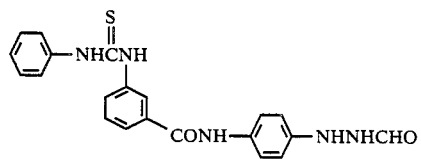

(6) Layer containing 0.43 g/m² of 2,5-di(t-pentadecyl)hydroquinone, 0.1 g/m² of trihexylphosphate, and 0.4 g/m² of trihexylphosphate, and 0.4 g/m² of gelatin.

(7) Layer containing 0.3 g/m² of the magenta dye releasing redox compound illustrated below, 0.08 g/m² of tricyclohexylphosphate, 0.009 g/m² of 2,5-di-tert-pentadecylhydroquinone, and 0.5 g/m² of gelatin.

(8) Green-sensitive emulsion layer containing a green-sensitive internal latent image type direct-positive silver bromide emulsion (containing 0.82 g/m² of silver), 0.9 g/m² of gelatin, 0.03 mg/m² of the same nucleating agent as used in layer (5), and 0.08 g/m² of sodium salt of 2-sulfo-5-n-pentadecylhydroquinone.

(9) The same interlayer as (6).

(10) Layer containing 0.53 g/m² of the yellow dye releasing redox compound having the following structure, 0.13 g/m² of tricyclohexyl phosphate, 0.014 g/m² of 2,5-di-t-pentadecylhydroquinone, and 0.7 g/m² of gelatin.

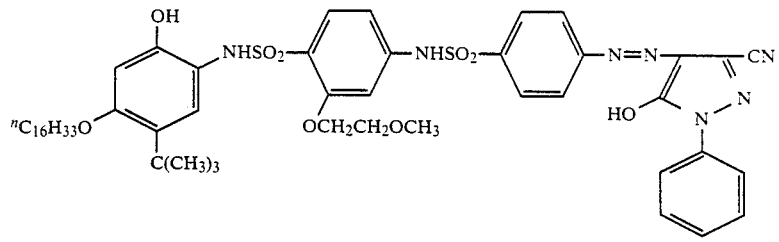

(11) Blue-sensitive emulsion containing a blue-sensitive internal image type direct-positive silver bromide emulssion (containing 1.09 g/m² of silver), 1.1 g/m² of gelatin, 0.04 mg/m² of the same nucleating agent as used in the layer (5), 0.07 g/m² of sodium salt of 2-sulfo-5-n-pentadecylhydroquinone, and the compound shown in Table 4 in the amount described in Table 4.

(12) Ultraviolet absorbing layer containing the ultraviolet absorbents with the following structures in an amount of $4 \times 10^{-3}$ mol/m² each, and 0.30 g/m² of gelatin.

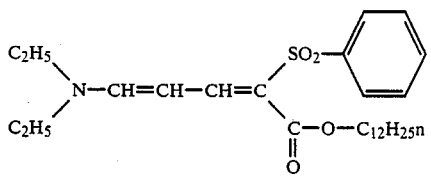

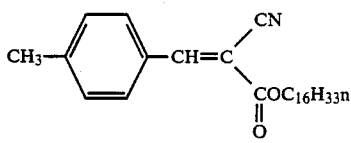

(13) Protective layer containing 0.10 g/m² of polymethylmethacrylate latex (mean particle size: 4 microns), 0.8 g/m² of gelatin and 0.02 g/m² of triacyrloyltriazine as a hardener.

Preparation of Cover Sheet A:

A cover sheet was prepared by coating on a transparent polyethylene terephthalate support the following layers (1') to (4') in this order.

(1') Neutralizing layer containing 10 g/m² of acrylic acid/butylacrylate (8/2 by weight) copolymer with a mean molecular weight of 50,000, and 0.2 g/m² of 1,4-bis(2,3-epoxypropoxy)butane.

(2') Second timing layer prepared by coating a mixture constituted with 95 wt % of cellulose acetate (acetylation degree: 51.0%) and 5 wt % of a methyl vinyl ether/maleic acid monomethyl ester alternating copolymer at a coverage of 7.5 g/m².

(3') Auxiliary neutralizing layer containing a 1.05 g/m² of a methyl vinyl ether/maleic anhydride alternating copolymer, and 0.98 mmol/m² of 5-(2-cyano-1-methylthio)-1-phenyltetrazole.

(4') First timing layer prepared by mixing a styrene/n-butyl acrylate/acrylic acid/N-methylolacrylamide (49.7/42.3/3/5 by weight) copolymer latex and a methylmethacrylate/acrylic acid/N-methylolacrylamide (93/4/3 by weight) copolymer latex in a ratio of 6 to 4 on a solids basis, and coating the mixture in a layer 2 microns thick.

| Composition of processing solution A: | |
|---|---|
| 1-p-tolyl-4-hydroxymethyl-4-methyl-3-pyrazolidinone | 14 g |
| Methylhydroquinone | 0.3 g |
| 5-Methylbenzotriazole | 3.5 g |
| Sodium sulfite (anhydrate) | 0.2 g |
| Sodium salt of carboxymethyl cellulose | 58 g |
| Potassium hydroxide (28% aq. soln.) | 200 ml |
| Benzyl alcohol | 1.5 ml |
| Carbon black | 150 g |
| Water | 685 ml |

Each of the thus prepared light-sensitive elements 1 to 9 was optically exposed through a continuous wedge, and then passed between a pair of pressure-applying rollers in the condition that it was combined with the above-described processing solution and the cover sheet, resulting in spread of the processing solution between the sensitive element and the cover sheet. After the lapse of 1 hour, densities were measured with a color densitometer, and Dmax and Dmin shown in Table 4 were obtained.

In addition, the change in Dmax was examined every 5 seconds immediately after the spread processing, and the time required for the density to be reduced to one-half the density (Dmax) measured at the lapse of 1 hour from the spread of processing solution was examined. The time determined represents the transfer speed, i.e., the shorter, the better.

As can be from the data shown in Table 4, the photographic elements utilizing the high molecular compounds of the present invention had greatly lowered Dmin without a drop in Dmax, similar to the photographic elements utilizing low molecular antifoggant-releasing compounds corresponding to their respective high molecular ones, and what is more, had a great advantage of no retardation in transfer speed.

Moreover, the high molecular compounds of the present invention proved table to accomplish effects equivalent to those of the low molecular compounds corresponding thereto even when the former compounds were used in smaller amounts than the latter, based on unit molar quantity.

It is assumed that this merit results from changes caused by converting low molecular compounds into high molecular ones in their exisiting state in the photographic system, and in its turn, in timing of cross-speed.

Further, it was proved by other analytical experiments that a difference in transfer speed corresponds to a difference in silver development speed. Namely, retardation of transfer is attributable to slowness of silver development.

TABLE 4

| | Compound | Amount | $D_{max}{}^B$ | $D_{min}{}^B$ | Transfer Speed $T_{50}$ % (sec.) | Note |
|---|---|---|---|---|---|---|
| 1 | Absent | — | 1.89 | 0.33 | 113 | Comparison |
| 2 | Comparative Compound AF-1 | $1.0 \times 10^{-5}$ (mol/m²) | 1.85 | 0.32 | 119 | Comparison |
| 3 | Comparative Compound AF-1 | $5.0 \times 10^{-5}$ (mol/m²) | 1.80 | 0.30 | 152 | Comparison |
| 4 | Comparative Compound AF-2 | $1.4 \times 10^{-4}$ (mol/m²) | 1.88 | 0.27 | 113 | Comparison |
| 5 | Comparative Compound AF-3 | $1.4 \times 10^{-4}$ (mol/m²) | 1.88 | 0.26 | 110 | Comparason |
| 6 | Comparative Compound AF-4 | $1.4 \times 10^{-4}$ (mol/m²) | 1.87 | 0.25 | 112 | Comparison |
| 7 | Present Compound 7 | $1.4 \times 10^{-4}$ (unit mol/m²) | 1.88 | 0.25 | 112 | Invention |
| 8 | Present Compound 8 | $1.4 \times 10^{-4}$ (unit mol/m²) | 1.89 | 0.27 | 113 | Invention |
| 9 | Present | $1.4 \times 10^{-4}$ (unit mol/m²) | 1.87 | 0.25 | 114 | Invention |

TABLE 4-continued
| Compound | Amount | $D_{max}{}^B$ | $D_{min}{}^B$ | Transfer Speed $T_{50}\%$ (sec.) | Note |
|---|---|---|---|---|---|
| Compound 9 | | | | | |
Comparative Compound AF-1
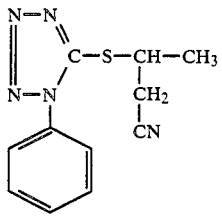
Comparative Compound AF-2
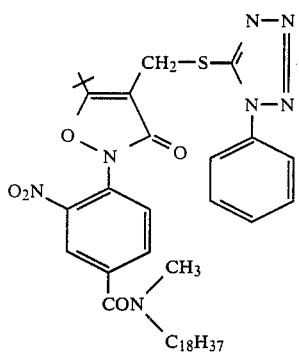
Comparative Compound AF-3
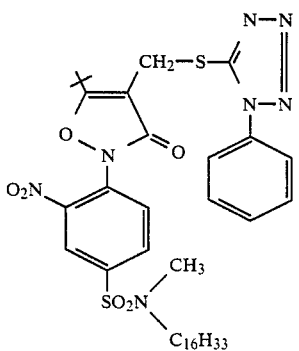
Comparative Compound AF-4
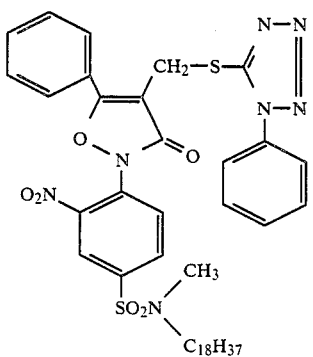
Present Compound 7

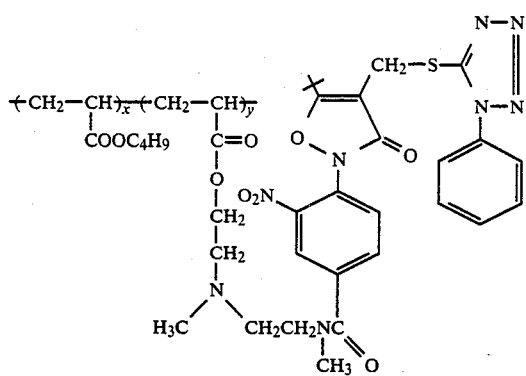

x/y = 50/50 (wt/wt)

Present Compound 8

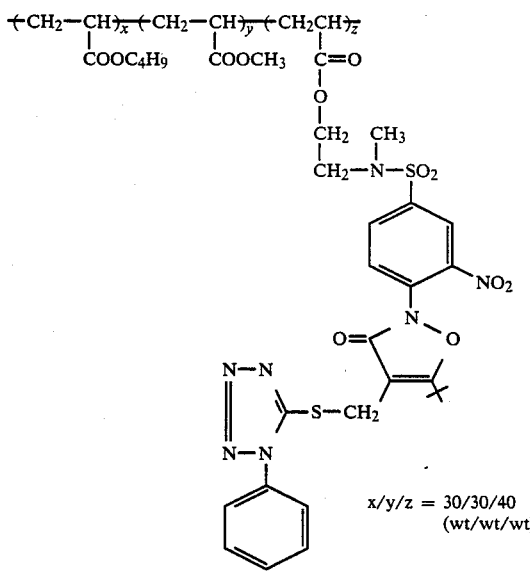

x/y/z = 30/30/40 (wt/wt/wt)

Present Compound 9

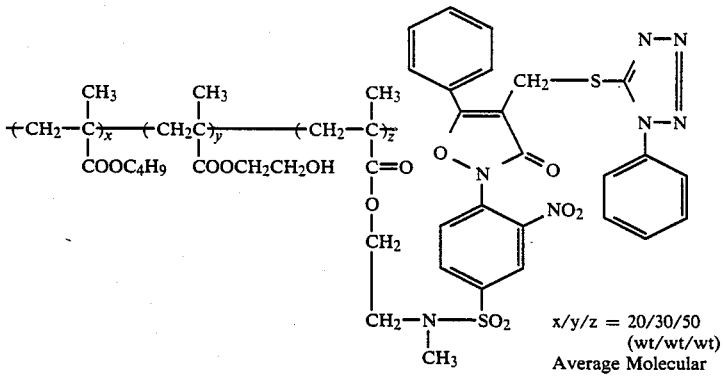

x/y/z = 20/30/50 (wt/wt/wt)
Average Molecular Weight: 13,000

EXAMPLE 5

Samples 501 and 502 were prepared in the same manner as in Example 2, except the following compounds were used respectively in place of the compound UV-1 (wherein gelatin dispersions of the compounds used were prepared in the same manner as those of the compounds 4, 5 and 6).

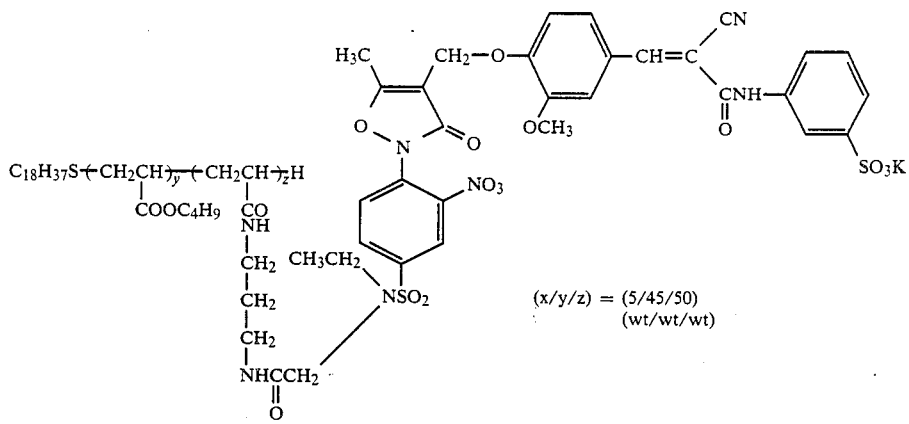

Compound 10

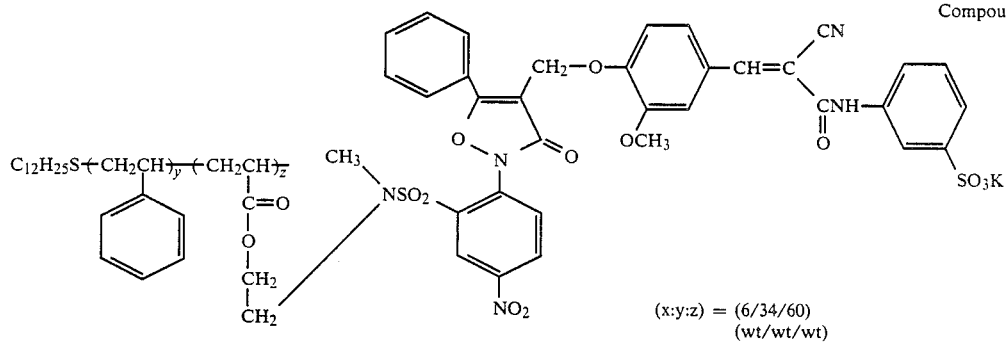

Compound 11

Samples 501 and 502 were subjected to the same photographic processing as employed in Example 2. Thereupon, these samples had the same tendency as observed in Samples 204 to 206.

While the invention has been described in detail and with reference to specific embodiments thereof, it will be apparent to one skilled in the art that various changes and modifications can be made therein without departing from the spirit and scope thereof.

What is claimed is:

1. A silver halide light-sensitive material comprising a support having thereon at least one silver halide emulsion layer, and containing a compound containing a repeating unit, said compound containing a repeating unit being connected at the repeating unit to a compound represented by formula (I) at the position of the PWR or Time moiety:

PWR—(Time)$_t$PUG     (I)

wherein PWR represents a moiety capable of releasing —(Time)$_t$PUG upon reduction, and PUG represents a group which can fulfill a photographically useful function after the release; Time represents a moiety capable of releasing PUG through a reaction subsequent to the release from PWR in the form of —(Time)$_t$PUG; and t represents 0 or 1, said compound represented by formula (I) being a compound represented by formula (II):

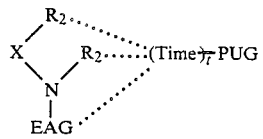

wherein EAG represents an electron accepting group; and N represents a nitrogen atom, and X represents an oxygen atom (—O—), a sulfur atom (—S—), or a nitrogen-containing group (—N(R$_3$)—); R$_1$, R$_2$, and R$_3$ each represents a mere bonding hand, or a group other than a hydrogen atom; R$_1$, R$_2$, R$_3$ and EAG may combine with one another to form a ring; and Time represents a group to release PUG through a reaction which succeeds taking advantage of the N—X bond cleavage as a trigger, t represents 0 or 1, and when t is 0, Time represents a mere bonding hand; and wherein each of the full lines indicates a bond, and the dashed lines indicate that at least one of them is a bond; and PUG has the same meaning as in formula (I).

2. The silver halide light-sensitive material of claim 1, wherein said compound represented by formula (II) is a compound represented by formula (III):

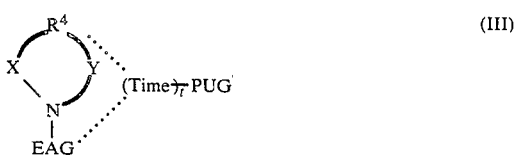

wherein Y represents a divalent linking group; R$_4$ represents atoms which are bonded to X and Y and complete a 5- to 8-membered heterocyclic ring together with the nitrogen atom; and N, X, EAG, Time, t and PUG have the same meanings as in the claim 1, respectively.

3. The silver halide light-sensitive material of claim 1, wherein $R^1$ and $R^3$ each represents a substituted or unsubstituted alkyl group, a substituted or unsubstituted alkenyl group, a substituted or unsubstituted alkynyl group, a substituted or unsubstituted aryl group, a substituted to unsubstituted heterocyclic group, a substituted or unsubstituted acyl group, or a substituted or unsubstituted sulfonyl group; $R^2$ represents a substituted or unsubstituted acyl group or a substituted or unsubstituted sulfonyl group; and X represents an oxygen atom.

4. The silver halide light-sensitive material of claim 2, wherein Y represents

or $-SO_2-$.

5. The silver halide light-sensitive material of claim 2, wherein EAG is represented by formula (A):

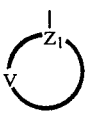

(A)

wherein $Z_1$ represents

or a nitrogen atom; and V represents an atomic group necessary for forming a 3-membered to 8-membered aromatic ring containing members selected from

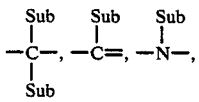

$-N=$, $-O-$, $-S-$ and $-SO_2-$; wherein Sub represents a hydrogen atom or a substituent, plural Sub groups may be the same or different, and at least two Sub groups may be linked to form a 3-membered to 8-membered saturated or unsaturated carbon ring or a 3-membered to 8-membered saturated or unsaturated heterocyclic ring; provided that the sum of the Hammett's sigma constants and Hammett's para constants of said Sub groups is at least +0.50.

6. The silver halide light-sensitive material of claim 1, wherein said compound containing a repeating unit to which the compound represented by formula (II) is connected at the PWR or Time position is a high molecular compound represented by formula (IV):

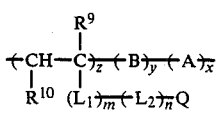

(IV)

wherein $R^9$ represents a hydrogen atom or a substituted or unsubstituted alkyl group containing 1 to 6 carbon atoms; $R^{10}$ represents a hydrogen atom or $-COOR^9$, wherein $R^9$ has the same meaning as above; $L_1$ represents an alkylene group containing 1 to 6 carbon atoms, an arylene group containing 6 to 10 carbon atoms, an arylenealkylene group containing 7 to 11 carbon atoms, $-COO-$, $-OCO-$ or $-CONR^{11}-$, wherein $R^{11}$ represents a hydrogen atom, or a substituted or unsubstituted alkyl group containing 1 to 4 carbon atoms; $L_2$ represents a group connecting $L_1$ to Q; m represents 0 or 1; n represents 0 or 1; Q represents a group formed by eliminating a hydrogen atom from the compound represented by formula (II) at the PWR or Time position, which is attached to $-(L_1)_{\overline{m}}(L_2)_{\overline{n}}$; B represents a monomer unit formed by copolymerization of monomers containing an ethylenically unsaturated group; A represents a monomer unit formed by copolymerization of monomers containing at least two copolymerizable ethylinically unsaturated groups, at least one of which is present in a side chain; and x, y and z each represents a percentage by weight, x ranging from 0 to about 20, y from 0 to about 80, and z from about 20 to 100.

7. The silver halide photographic material of claim 1, wherein said compound containing a repeating unit to which the compound represented by formula (II) is connected is a compound represented by formula (V):

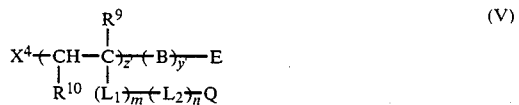

(V)

wherein E represents a monovalent group containing at least 8 carbon atoms; $X^4$ represents a hydrogen atom or a halogen atom; B, $L_1$, $L_2$, Q, $R^9$, $R^{10}$, m, and n have the same meanings as in claim 5 respectively; and y' and z' represent weight percentages of their respective polymerizing components, other than E and $X^4$, the ratio y':z' ranging from 0:100 to about 90:10.

8. The silver halide photographic material of claim 1, wherein said compound containing a repeating unit to which the compound represented by formula (II) is a high molecular compound represented by formula (VI):

(VI)

wherein M represents a divalent group containing a residue formed by eliminating a hydrogen atom from the compound represented by formula (II) at the PWR or Time position; and $L^3$ represents a divalent group which constitutes the main chain of a high molecular compound together with M.

9. The silver halide light-sensitive material of claim 1, wherein said group which can fulfill a photographically useful function is selected from the group consisting of a development inhibitor, a development inhibitor precursor, a development accelerator, a development accelerator precursor, a nucleating agent, a nucleating agent precursor, a coupler, a coupler precursor, a diffusible dye, a diffusible dye precursor, a non-diffusible dye, a non-diffusible dye precursor, a desilvering accelerator, a desilvering accelerator precursor, a desilvering inhibitor, a desilvering inhibitor precursor, a halide, a halide precursor, a silver halide solvent, a silver halide solvent precursor, a redox competitive compound, a redox competitive compound precursor, a developer, a developer precursor, an auxiliary developer, an auxiliary developer precursor, a fixation accelerator, a fixation accelerator precursor, a fixation inhibitor, a fixation inhibitor precursor, a silver image stabilizer, a silver image stabilizer precursor, a toning agent, a toning agent precursor, a processing dependence improver, a processing dependence improver precursor, a halftone improver, a halftone improver precursor, a dye image stabilizer, a dye image stabilizer precursor, a dye, a dye precursor, a surface active agent, a surface active agent precursor, a hardener, a hardener precursor, a desensitizer, a desensitizer precursor, a high contrast imparting agent, a high contrast imparting agent precursor, a chelating agent, a chelating agent precursor, a brightening agent, a brightening agent precursor, an ultraviolet absorbent, an ultraviolet absorbent precursor, a nucleation accelerator, and a nucleation accelerator precursor.

10. The silver halide light-sensitive material of claim 6, wherein the copolymerizable ethylenically unsaturated monomer which is copolymerized to form the monomer unit represented by B is selected from the group consisting of ethylene, propylene, 1-butene, isobutene, styrene, α-methylstyrene, vinyltoluene, a monoethylenically unsaturated ester of an aliphatic acid, an ester of an ethylenically unsaturated monocarboxylic acid, an ester of an ethylenically unsaturated dicarboxylic acid, acrylonitrile, methacrylonitrile, butadiene and isoprene; and said monomer which is copolymerized to form the monomer unit represented by A is selected from the group consisting of divinylbenzene, ethylene glycol dimethacrylate, isopropylene glycol dimethacrylate, neopentyl glycol dimethacrylate, tetramethylene glycol diacrylate and tetramethylene glycol dimethacrylate.

11. The silver halide light-sensitive material of claim 10, wherein said monomer which is copolymerized to form the monomer unit represented by A is divinylbenzene or ethylene glycol dimethacrylate.

12. The silver halide light-sensitive material of claim 7, wherein said monovalent group represented by E is represented by formula (B):

wherein $E^1$ represents an unsubstituted alkyl group, a substituted alkyl group, a substituted aryl group, or a substituted naphthyl group; $Y^1$ represents —O—, —S—, —SO—, or —SO$_2$—; and p is 0 or 1

13. The silver halide light-sensitive material of claim 8, wherein said high molecular compound represented by formula (VI) is selected from the group consisting of a polyamide, a polyurethane, a polyurea, and a polyester.

14. The silver halide light-sensitive material of claim 1, wherein said compound containing a repeating unit to which a compound represented by formula (II) is connected has a number average molecular weight of from about 1,500 to 150,000.

15. The silver halide light-sensitive material of claim 1, wherein said group which can fulfill a photographically useful function is selected from (a) a dye or an ultraviolet absorbent, each present in an amount of from about $10^{-3}$ to $10^3$ g/m$^2$; (b) a development inhibitor present in an amount of from about $10^{-7}$ to $10^{-1}$ mole per mole of said silver halide; (c) a development accelerator or a nucleating agent, each present in an amount of from about $10^{-7}$ to $10^{-2}$ mole per mole of said silver halide; and (d) a silver halide solvent present in an amount of from about $10^{-5}$ to $10^3$ mole per mole of said silver halide.

16. The silver halide light-sensitive material of claim 15, wherein said group which can fulfill a photographically useful function is selected from (a) a dye or an ultraviolet absorbent, each present in an amount from about $10^{-3}$ to 10 g/m$^2$; (b) a development inhibitor present in an amount from about $10^{-3}$ to $10^{-2}$ mole per mole of said silver halide; (c) a development accelerator or a nucleating agent, each present in an amount of from about $10^{-5}$ to $10^{-2}$ mole per mole of said silver halide; and (d) a silver halide solvent present in an amount of from about $10^{-4}$ to 10 mole per mole of said silver halide.

17. The silver halide light-sensitive material of claim 2, wherein X represents an oxygen atom.

18. The silver halide light-sensitive material of claim 2, wherein Y represents

or —SO$_2$—.

19. The silver halide light-sensitive material of claim 2, wherein the

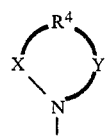

moiety represents

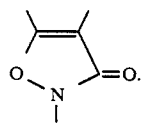

* * * * *